(12) United States Patent
Rodino-Klapac et al.

(10) Patent No.: US 11,358,993 B2
(45) Date of Patent: Jun. 14, 2022

(54) ADENO-ASSOCIATED VIRUS VECTOR DELIVERY OF B-SARCOGLYCAN AND MICRORNA-29 AND THE TREATMENT OF MUSCULAR DYSTROPHY

(71) Applicant: RESEARCH INSTITUTE AT NATIONWIDE CHILDREN'S HOSPITAL, Columbus, OH (US)

(72) Inventors: Louise Rodino-Klapac, E. Groveport, OH (US); Jerry R. Mendell, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 695 days.

(21) Appl. No.: 16/093,027

(22) PCT Filed: Apr. 14, 2017

(86) PCT No.: PCT/US2017/027583
§ 371 (c)(1),
(2) Date: Oct. 11, 2018

(87) PCT Pub. No.: WO2017/180976
PCT Pub. Date: Oct. 19, 2017

(65) Prior Publication Data
US 2019/0202880 A1    Jul. 4, 2019

Related U.S. Application Data

(60) Provisional application No. 62/433,548, filed on Dec. 13, 2016, provisional application No. 62/323,333, filed on Apr. 15, 2016.

(51) Int. Cl.
| | | |
|---|---|---|
| *A61P 21/00* | (2006.01) |
| *C07K 14/47* | (2006.01) |
| *A61K 48/00* | (2006.01) |
| *C07K 14/705* | (2006.01) |
| *C12N 15/86* | (2006.01) |
| *A61P 25/14* | (2006.01) |
| *C12N 15/85* | (2006.01) |

(52) U.S. Cl.
CPC ...... *C07K 14/4716* (2013.01); *A61K 48/0058* (2013.01); *A61K 48/0075* (2013.01); *A61P 21/00* (2018.01); *A61P 25/14* (2018.01); *C07K 14/705* (2013.01); *C12N 15/85* (2013.01); *C12N 15/86* (2013.01); *C12N 2750/14143* (2013.01); *C12N 2750/14145* (2013.01); *C12N 2800/22* (2013.01); *C12N 2830/008* (2013.01)

(58) Field of Classification Search
CPC .. C07K 14/4716; C07K 14/705; C12N 15/85; C12N 15/86; C12N 2750/14143; C12N 2750/14145; C12N 2800/22; C12N 2830/008; A61P 25/14; A61P 21/00; A61K 48/0058; A61K 48/0075
See application file for complete search history.

(56) References Cited

U.S. PATENT DOCUMENTS

| | | | |
|---|---|---|---|
| 5,173,414 A | 12/1992 | Lebkowski et al. |
| 5,658,776 A | 8/1997 | Flotte et al. |
| 5,672,694 A | 9/1997 | Campbell et al. |
| 5,786,211 A | 7/1998 | Johnson |
| 6,258,595 B1 | 7/2001 | Gao et al. |
| 6,566,118 B1 | 5/2003 | Atkinson et al. |
| 7,883,858 B2 | 2/2011 | Hood et al. |
| 9,434,928 B2 | 9/2016 | Mendell et al. |
| 2001/0029040 A1 | 10/2001 | Toyo-Oka |
| 2003/0225260 A1 | 12/2003 | Snyder |
| 2006/0154250 A1 | 7/2006 | Morris et al. |
| 2007/0099251 A1 | 5/2007 | Zhang et al. |
| 2008/0249052 A1 | 10/2008 | Duan et al. |
| 2010/0003218 A1 | 1/2010 | Duan et al. |
| 2010/0075866 A1 | 3/2010 | Hood et al. |
| 2011/0104120 A1 | 5/2011 | Xiao et al. |
| 2011/0294193 A1 | 12/2011 | Amalfitano et al. |
| 2011/0301226 A1 | 12/2011 | Mendell et al. |
| 2012/0087862 A1 | 4/2012 | Hood et al. |
| 2014/0010861 A1 | 1/2014 | Bancel et al. |
| 2014/0234255 A1 | 8/2014 | Lai et al. |

(Continued)

FOREIGN PATENT DOCUMENTS

| | | |
|---|---|---|
| CN | 101896186 A | 11/2010 |
| WO | WO-1995/013392 A1 | 5/1995 |
| WO | WO-1996/017947 A1 | 6/1996 |

(Continued)

OTHER PUBLICATIONS

Pozsgai et al., β-Sarcoglycan gene transfer leads to functional improvement in a model of LGMD2E (S61.002), *Neurology*. 82:Supple. 1-3 (2014).

(Continued)

*Primary Examiner* — Antonio Galisteo Gonzalez
*Assistant Examiner* — Khaleda B Hasan
(74) *Attorney, Agent, or Firm* — Marshall, Gerstein & Borun LLP

(57) ABSTRACT

Described herein are recombinant AAV vectors comprising a polynucleotide sequence comprising β-sarcoglycan and methods of using the recombinant vectors to reduce or prevent fibrosis in a mammalian subject suffering from a muscular dystrophy. Also described herein are combination therapies comprising administering AAV vector(s) expressing β-sarcoglycan and miR-29c to a mammalian subject suffering from a muscular dystrophy.

20 Claims, 27 Drawing Sheets
Specification includes a Sequence Listing.

(56) References Cited

U.S. PATENT DOCUMENTS

2014/0256802 A1 9/2014 Boye et al.
2014/0323956 A1 10/2014 Mendell et al.

FOREIGN PATENT DOCUMENTS

| WO | WO-1997/006243 A1 | 2/1997 |
|---|---|---|
| WO | WO-1997/008298 A1 | 3/1997 |
| WO | WO-1997/009441 A2 | 3/1997 |
| WO | WO-1997/021825 A1 | 6/1997 |
| WO | WO-1998/009657 A2 | 3/1998 |
| WO | WO-1999/011764 A2 | 3/1999 |
| WO | WO-2001/083692 A2 | 11/2001 |
| WO | WO-2002/053703 A2 | 7/2002 |
| WO | WO-2009/054725 A2 | 4/2009 |
| WO | WO-2015/110449 A1 | 7/2015 |
| WO | WO-2015/197232 A1 | 12/2015 |

OTHER PUBLICATIONS

Draviam et al., The β-δ-core of sarcoglycan is essential for deposition at the plasma membrane, *Muscle and Nerve*. 34:691-701 (2006).
Dressman, D., AAV-Mediated gene transfer to models of muscular dystrophy: Insights into assembly of multi-subunit membrane proteins, University of Pittsburgh (1997).
Meadows et al., Micro-RNA-29 Overexpression by adeno-associated virus suppresses fibrosis in mdx:utrn+/- Mice (S61.003), *Neurology*. 82:S61.003 (Abstract) (2014).
Zhang et al., Dual AAV therapy ameliorates exercise-induced muscle injury and functional ischemia in murine models of Duchenne muscular dystrophy, *Hum. Mol. Genet*. 22:3720-9 (2013).
Anderson et al., Nucleic Acid Hybridisation: A Practical Approach, IRL Press Limited, Oxford, England, Ch. 4.
Angelini et al., The clinical spectrum of sarcoglycanopathies. *Neurology*. 52:176-179 (1999).
Araishi et al., Loss of the sarcoglycan complex and sarcospan leads to muscular dystrophy in beta-sarcoglycan-deficient mice, *Hum. Mol. Genet*. 8:1589-1598 (1999).
Barresi et al., Disruption of heart sarcoglycan complex and severe cardiomyopathy caused by beta sarcoglycan mutations, *J. Med. Genet*. 37: 102-107 (2000).
Beastrom et al., $Mdx^{5cv}$ mice manifest more severe muscle dysfunction and diaphragm force deficits than do mdx mice, *Musculoskeletal Pathology*. 179:2464-74 (2011).
Bonnemann et al., Beta-sarcoglycan (A3b) mutations cause autosomal recessive muscular dystrophy with loss of the sarcoglycan complex, *Nat. Genet*. 11:266-273 (1995).
Bonnemann et al., Genomic screening for beta-sarcoglycan gene mutations: missense mutations may cause severe limb-girdle muscular dystrophy type 2E (LGMD 2E), *Hum. Mol. Genet*. 5:1953-1961 (1996).
Chao et al. Several log increase in therapeutic transgene delivery by distinct adeno-associated viral serotype vectors, *Mol. Ther*. 2:619-23 (2000).
Chao et al., Sustained and complete phenotype correction of hemophilia B mice following intramuscular injection of AAV1 serotype vectors, *Mol. Ther*. 4:217-22 (2001).
Chicoine et al., Plasmapheresis eliminates the negative impact of AAV antibodies on micro-dystrophin gene expression following vascular delivery, *Mol Ther*. 22: 338-347 (2014).
Chicoine et al., Vascular delivery of rAAVrh74.MCK.GALGT2 to the gastrocnemius muscle of the rhesus macaque stimulates the expression of dystrophin and laminin alpha2 surrogates, *Mol Ther*. 22:713-724 (2014).
Clark et al., A stable cell line carrying adenovirus-inducible rep and cap genes allows for infectivity titration of adeno-associated virus vectors, *Gene. Ther*. 3:1124-32 (1996).
Clark et al., Highly purified recombinant adeno-associated virus vectors are biologically active and free of detectable helper and wild-type viruses, *Hum. Gene Ther*. 10:1031-1039 (1999).
Clark et al., Recombinant adeno-associated viral vectors mediate long-term transgene expression in muscle, *Hum. Gene Ther*. 8:659-69 (1997).
Cserjesi et al., Myogenin induces the myocyte-specific enhancer binding factor MEF-2 independently of other muscle-specific gene products, *Mol. Cell. Biol*. 11:4854-62 (1991).
De et al., High levels of persistent expression of alphal-antitrypsin mediated by the nonhuman primate serotype rh. 10 adeno-associated virus despite preexisting immunity to common human adeno-associated viruses, *Mol. Ther*. 13:67-76 (2006).
Dressman et al., Delivery of alpha- and beta-sarcoglycan by recombinant adeno-associated virus: efficient rescue of muscle, but differential toxicity, *Hum. Gene. Ther*. 13:1631-1646 (2002).
Durbeej et al., Disruption of the beta-sarcoglycan gene reveals pathogenetic complexity of limb-girdle muscular dystrophy type 2E, *Mol. Cell*. 5:141-151 (2000).
Fanin et al., LGMD2E patients risk developing dilated cardiomyopathy, *Neuromusc. Disord*. 13:303-309 (2003).
Flotte et al., Gene expression from adeno-associated virus vectors in airway epithelial cells, *Am. J. Respir Mol. Biol*. 7: 349-356, 1992.
Gao et al., Clades of Adeno-associated viruses are widely disseminated in human tissues, *J. Virol*. 78:6381-8 (2004).
GenBank Accession No. AF085716.1, Adeno-associated virus 5 DNA binding trs helicase (Rep22) and capsid protein (VP1) genes, complete cds, Feb. 9, 1999.
GenBank Accession No. AX753246.1, Sequence 1 from Patent EP1310571, Jun. 23, 2003.
GenBank Accession No. AX753249.1, Sequence 4 from Patent EP1310571, Jun. 23, 2003.
Genbank Accession No. NC_001401.0, Adeno-associated virus—2, complete genome, Aug. 13, 2018.
Genbank Accession No. NC_001729.1, Adeno-associated virus—3, complete genome, Aug. 13, 2018.
GenBank Accession No. NC_001829.1, Adeno-associated virus—4, complete genome, Aug. 13, 2018.
GenBank Accession No. NC_001862, Adeno-associated virus 6, complete genome, Jan. 12, 2004.
Genbank Accession No. NC_002077.1, Adeno-associated virus—1, complete genome, Aug. 13, 2018.
GenBank Accession No. NM_00232.4, *Homo sapiens* sarcoglycan beta (SGCB), Mrna, Feb. 20, 2019.
Gibertini et al., Fibrosis and inflammation are greater in muscles of beta-sarcoglycan-null mouse than mdx mouse, *Cell Tissue Res*. 356:427-443 (2014).
Grieger et al., Production and characterization of adeno-associated viral vectors, *Nat. Protoc*. 1:1412-1428 (2006).
Hakim et al., The passive mechanical properties of the extensor digitorum longus muscle are compromised in 2- to 20-mo-old mdx mice, *J. Appl. Physiol*. 110: 1656-1663 (2011).
Hermonat et al., Use of adeno-associated virus as a mammalian DNA cloning vector: transduction of neomycin resistance into mammalian tissue culture cells, *Proc. Natl. Acad. Sci. USA*. 81:6466-70 (1984).
Herzog et al., Stable gene transfer and expression of human blood coagulation factor IX after intramuscular injection of recombinant adeno-associated virus, *Proc. Natl. Acad. Sci. USA*. 94:5804-9 (1997).
International Search Report and Written Opinion, PCT/US2017/027636 (dated Jul. 5, 2017).
International Preliminary Report on Patentability, PCT/US2017/027636 (dated Oct. 16, 2018).
Johnson et al., muscle creatine kinase sequence elements regulating skeletal and cardiac muscle expression in transgenic mice, *Mol. Cell. Biol*. 9:3393-99 (1989).
Kessler et al., Gene delivery to skeletal muscle results in sustained expression and systemic delivery of a therapeutic protein, *Proc. Natl. Acad. Sci. USA*. 93:14082-7 (1996).
Kobayashi et al., Sarcolemma-localized nNOS is required to maintain activity after mild exercise, *Nature*. 456:511-5 (2008).

(56) References Cited

OTHER PUBLICATIONS

Laughlin et al., Cloning of infectious adeno-associated virus genomes in bacterial plasmids, *Gene.* 23:65-73 (1983).
Laws et al., Progression of kyphosis in mdx mice, *J. Appl. Physiol.* 97:1970-7 (2004).
Lebkowski et al., Adeno-associated virus: a vector system for efficient introduction and integration of DNA into a variety of mammalian cell types, *Mol. Cell. Biol.* 8:3988-96 (1988).
Lewis et al., Generation of neutralizing activity against human immunodeficiency virus type 1 in serum by antibody gene transfer, *J. Virol.* 76:8769-75 (2002).
Liu et al., Adeno-associated virus-mediated microdystrophin expression protects young mdx muscle from contraction-induced injury, *Mol. Ther.* 11:245-256 (2005).
Mader et al., A steroid-inducible promoter for the controlled overexpression of cloned genes in eukaryotic cells, *Proc. Natl. Acad. Sci. USA.* 90:5603-7 (1993).
Marsic et al., Vector design Tour de Force: integrating combinatorial and rational approaches to derive novel adeno-associated virus variants, *Mol. Ther.* 22:1900-9 (2014).
Matsuda et al., Visualization of dystrophic muscle fibers in mdx mouse by vital staining with Evans blue: evidence of apoptosis in dystrophin-deficient muscle, *J. Biochem.* 118: 959-964 (1995).
McCarty et al., Adeno-associated virus terminal repeat (TR) mutant generates self-complementary vectors to overcome the rate-limiting step to transduction in vivo, *Gene Ther.* 10: 2112-2118 (2003).
McCarty et al., Self-complementary recombinant adeno-associated virus (scAAV) vectors promote efficient transduction independently of DNA synthesis, *Gene Ther.* 8: 1248-1254 (2001).
McLaughlin et al., Adeno-associated virus general transduction vectors: analysis of proviral structures, *J. Virol.* 62:1963-73 (1988).
Melacini et al., Heart involvement in muscular dystrophies due to sarcoglycan gene mutations, *Muscle Nerve.* 22:473-479 (1999).
Mendell et al., A phase 1/2a follistatin gene therapy trial for becker muscular dystrophy, *Mol. Ther.* 23: 192-201 (2015).
Mendell et al., Gene Therapy for Spinal Muscular Atrophy Type 1 Shows Potential to Improve Survival and Motor Functional Outcomes, *Mol. Ther.* 24:S190 (2016).
Moore et al., Limb-girdle muscular dystrophy in the United States, *J. Neuropathol. Exp. Neurol.* 65: 995-1003 (2006).
Moorwood et al., Isometric and eccentric force generation assessment of skeletal muscles isolated from murine models of muscular dystrophies, *Journal of Visualized Experiments.* 71 :e50036 (2013).
Mori et al., Two novel adeno-associated viruses from cynomolgus monkey: pseudotyping characterization of capsid protein, *Virol.* 330:375-83 (2004).
Murphy et al., Long-term correction of obesity and diabetes in genetically obese mice by a single intramuscular injection of recombinant adeno-associated virus encoding mouse leptin, *Proc. Natl. Acad. Sci. USA.* 94:13921-6 (1997).
Muscat et al., Multiple 5'-Flanking regions of the human alpha-skeletal actin gene synergistically modulate muscle-specific expression, *Mol. Cell. Biol.* 7:4089-99 (1987).
Muzyczka, Use of adeno-associated virus as a general transduction vector for mammalian cells, *Curr. Top. Microbiol. Immunol.* 158:97-129 (1992).
Narayanaswami et al., Evidence-based guideline summary: diagnosis and treatment of limb-girdle and distal dystrophies: report of the guideline development subcommittee of the American Academy of Neurology and the practice issues review panel of the American Association of Neuromuscular & Electrodiagnostic Medicine, *Neurology.* 83:1453-1463 (2014).
Paul et al., Increased viral titer through concentration of viral harvests from retroviral packaging lines, *Hum. Gene. Ther.* 4:609-15 (1993).
Perrin et al., An experimental rabies vaccine produced with a new BHK-21 suspension cell culture process: use of serum-free medium and perfusion-reactor system, *Vaccine.* 13:1244-50 (1995).
Pozsgai et al., β-Sarcoglycan gene transfer decreases fibrosis and restores force in LGMD2E mice, *Gene Ther.* 23:57-66 (2016).

Rabinowitz et al., Cross-packaging of a single adeno-associated virus (AAV) type 2 vector genome into multiple AAV serotypes enables transduction with broad specificity, *J. Virol.* 76:791-801 (2002).
Rafael-Fortney et al., Early treatment with lisinopril and spironolactone preserves cardiac and skeletal muscle in duchenne muscular dystrophy mice, *Circulation.* 124:582-8 (2011).
Rodino-Klapac et al., A translational approach for limb vascular delivery of the micro-dystrophin gene without high volume or high pressure for treatment of Duchenne muscular dystrophy, *J. Transl. Med.* 5:45 (2007).
Rodino-Klapac et al., Lack of toxicity of alpha-sarcoglycan overexpression supports clinical gene transfer trial in LGMD2D, *Neurology.* 71: 240-247 (2008).
Rodino-Klapac et al., Persistent expression of FLAG-tagged micro dystrophin in nonhuman primates following intramuscular and vascular delivery, *Mol. Ther.* 18:109-117 (2010).
Sambrook et al., Molecular Cloning: A Laboratory Manual, Cold Spring Harbor Laboratory, Cold Spring Harbor, New York (2nd ed. 1989).
Samulski et al., Cloning of adeno-associated virus into pBR322: rescue of intact virus from the recombinant plasmid in human cells, *Proc. Natl. Acad. Sci. USA.* 79:2077-81 (1982).
Samulski et al., Helper-free stocks of recombinant adeno-associated viruses: normal integration does not require viral gene expression, *J. Virol.* 63:3822-8 (1989).
Sandona et al., Sarcoglycanopathies: molecular pathogenesis and therapeutic prospects, *Exp Rev. Mol. Med.* 11:e28 (2009).
Schnepp et al., Highly purified recombinant adeno-associated virus vectors. Preparation and quantitation, *Methods Mol. Med.* 69:427-43 (2002).
Semenza et al., hypoxia-inducible nuclear factors bind to an enhancer element located 3' to the human erythropoietin gene, *Proc. Natl. Acad. Sci. USA.* 88:5680-4 (1991).
Semplicini et al., Clinical and genetic spectrum in limb-girdle muscular dystrophy type 2E, *Neurology.* 84:1772-81 (2015).
Senapathy et al., Molecular cloning of adeno-associated virus variant genomes and generation of infectious virus by recombination in mammalian cells, *J. Biol. Chem.* 259:4661-6 (1984).
Shield et al., E-box sites and a proximal regulatory region of the muscle creatine kinase gene differentially regulate expression in diverse skeletal muscles and cardiac muscle of transgenic mice, *Mol. Cell. Biol.*16: 5058-5068 (1996).
Srivastava et al., Nucleotide sequence and organization of the adeno-associated virus 2 genome, *J. Virol.* 45:555-64 (1983).
Straub et al., Animal models for muscular dystrophy show different patterns of sarcolemmal disruption, *J. Cell Biol.* 139:375-385 (1997).
Sveen et al., Cardiac involvement in patients with limb-girdle muscular dystrophy type 2 and Becker muscular dystrophy, *Arch. Neurol.* 65:1196-1201 (2008).
Tratschin et al., A human parvovirus, adeno-associated virus, as a eucaryotic vector: transient expression and encapsidation of the procaryotic gene for chloramphenicol acetyltransferase, *Mol. Cell. Biol.* 4:2072-81 (1984).
Tratschin et al., Adeno-associated virus vector for high-frequency integration, expression, and rescue of genes in mammalian cells, *Mol. Cell. Biol.* 5:3251-60 (1985).
Voikar et al., Long-term indicidual housing in C57BL/6J and DBA/2 mice: assessment of behavioral consequences, *Genes, Brain and Behavior.* 4:240-52 (2005).
Wang et al., Construction and analysis of compact muscle-specific promoters for AAV vectors, *Gene Ther.* 15:1489-1499 (2008).
Wein et al., Translation from a DMD exon 5 IRES results in a functional dystrophin isoform that attenuates dystrophinopathy in humans and mice, *Nat. Med.* 20: 992-1000 (2014).
Weintraub et al., The myoD gene family: nodal point during specification of the muscle cell lineage, *Science.* 251:761-766 (1991).
Wong-Kisiel et al., Two siblings with limb-girdle muscular dystrophy type 2E responsive to deflazacort, *Neuromusc. Disord.* 20:122-124 (2010).

(56) References Cited

OTHER PUBLICATIONS

Xiao et al., Efficient long-term gene transfer into muscle tissue of immunocompetent mice by adeno-associated virus vector, *J. Virol.* 70:8098-108 (1996).
Pozsgai et al., 172. Pre-Clinical Efficacy Study of Beta-Sarcoglycan Gene Transfer, Molec. Ther., 21(1):s68 (2013).
Sun et al., Correction of Multiple Striated Muscles in Murine Pompe Disease Through Adeno-Associated Virus-mediated Gene Therapy, Mol. Ther., 16(8):1366-71 (2008).
Zanotti et al., Opposing roles of miR-21 and miR-29 in the progression of fibrosis in Duchenne muscular dystrophy., Biochem. Biophys. Acta., 1852:1451-4 (2015).
Genbank Accession No. NP_000233.1, Beta Sarcoglyan (43kD dystrophin-associated glycoprotein) *Homo Sapiens*, Mar. 19, 1999.
Meadows et al., Reducing Skeletal Muscle Fibrosis with AAV-Delivered miR-29 (P04.089), Neurol., 1 Supplement, (2012).

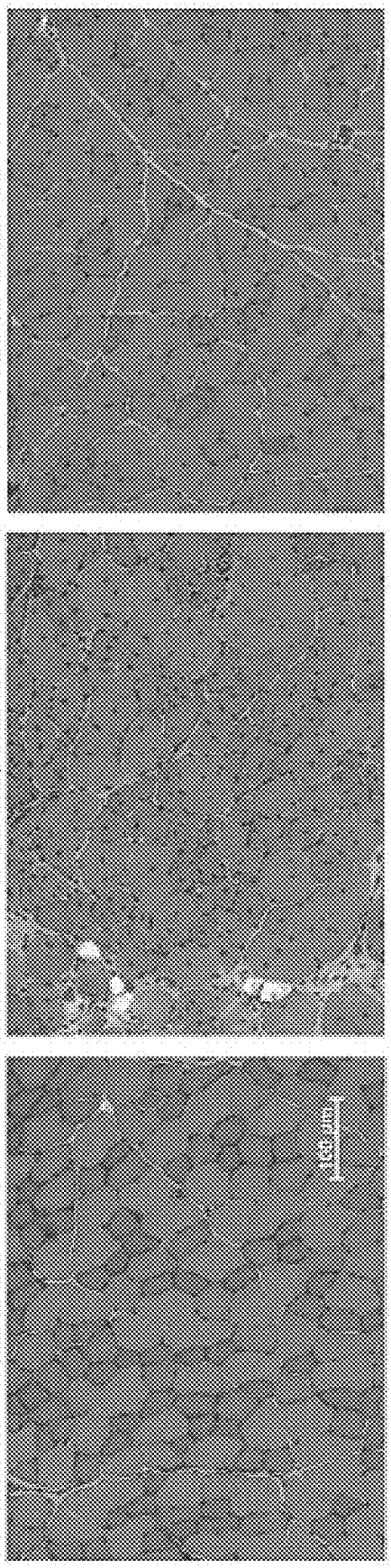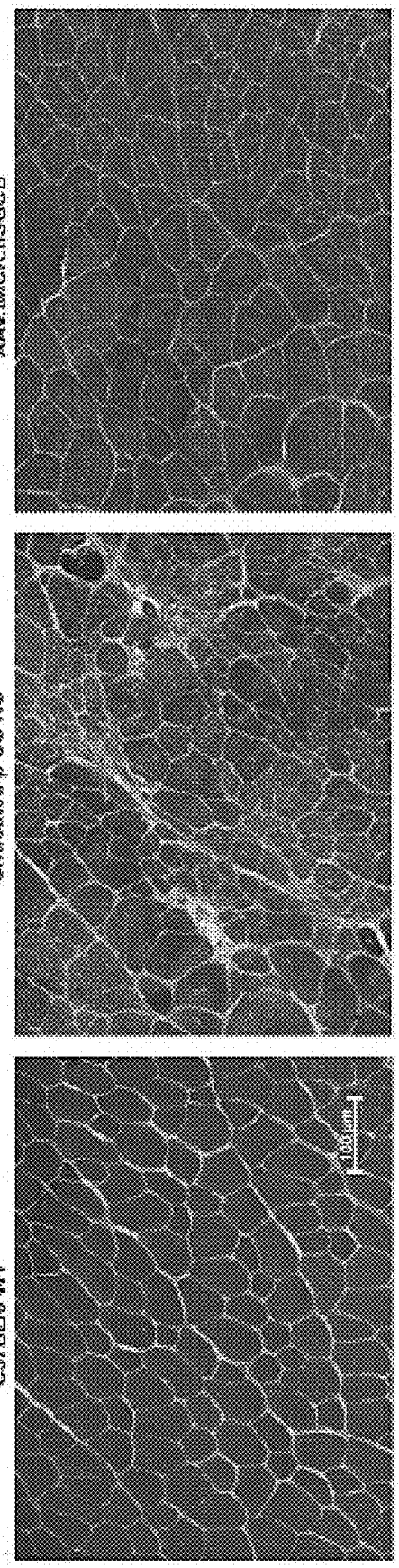
Figure 2A
Figure 2B

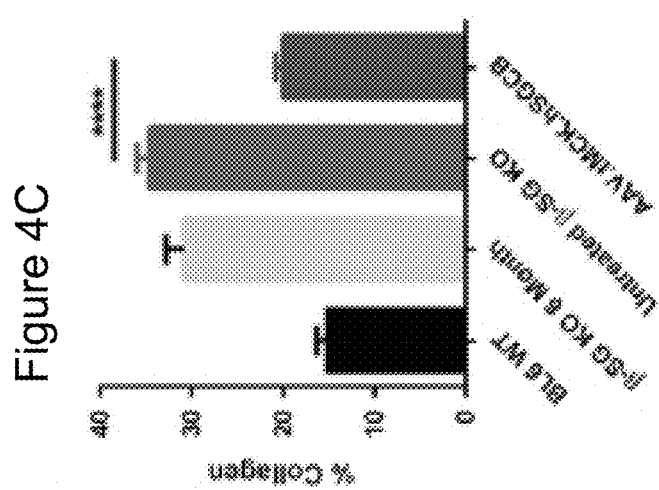
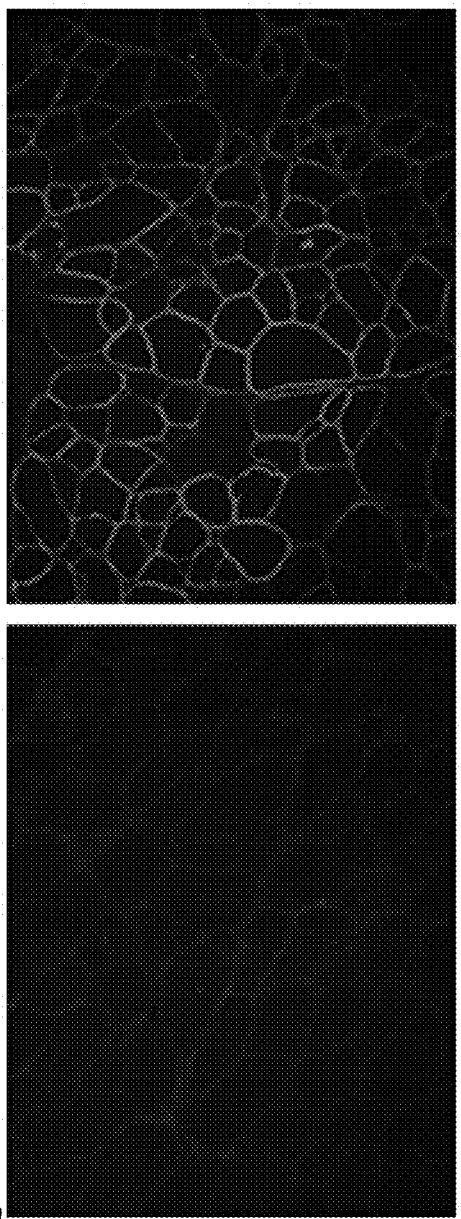
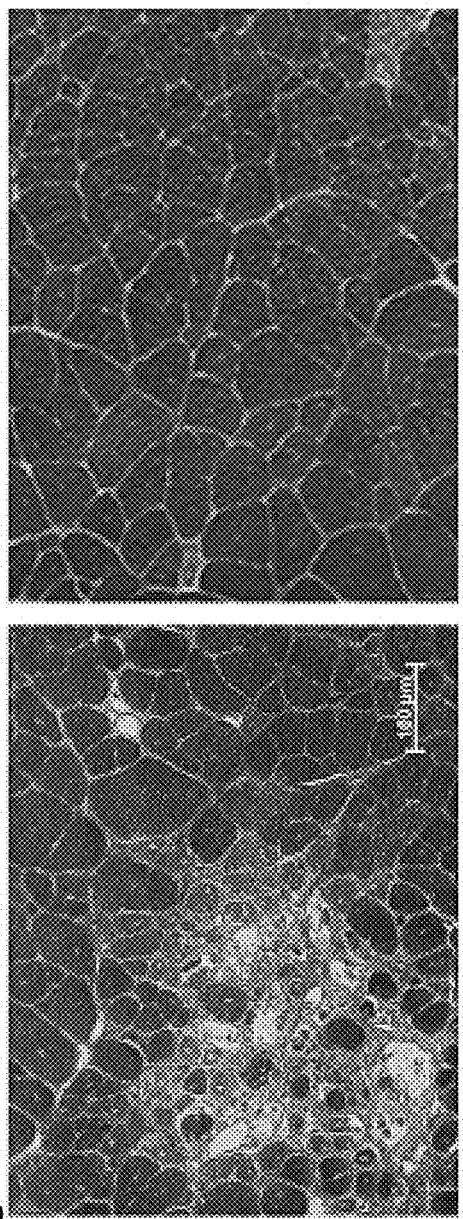

Figure 5A
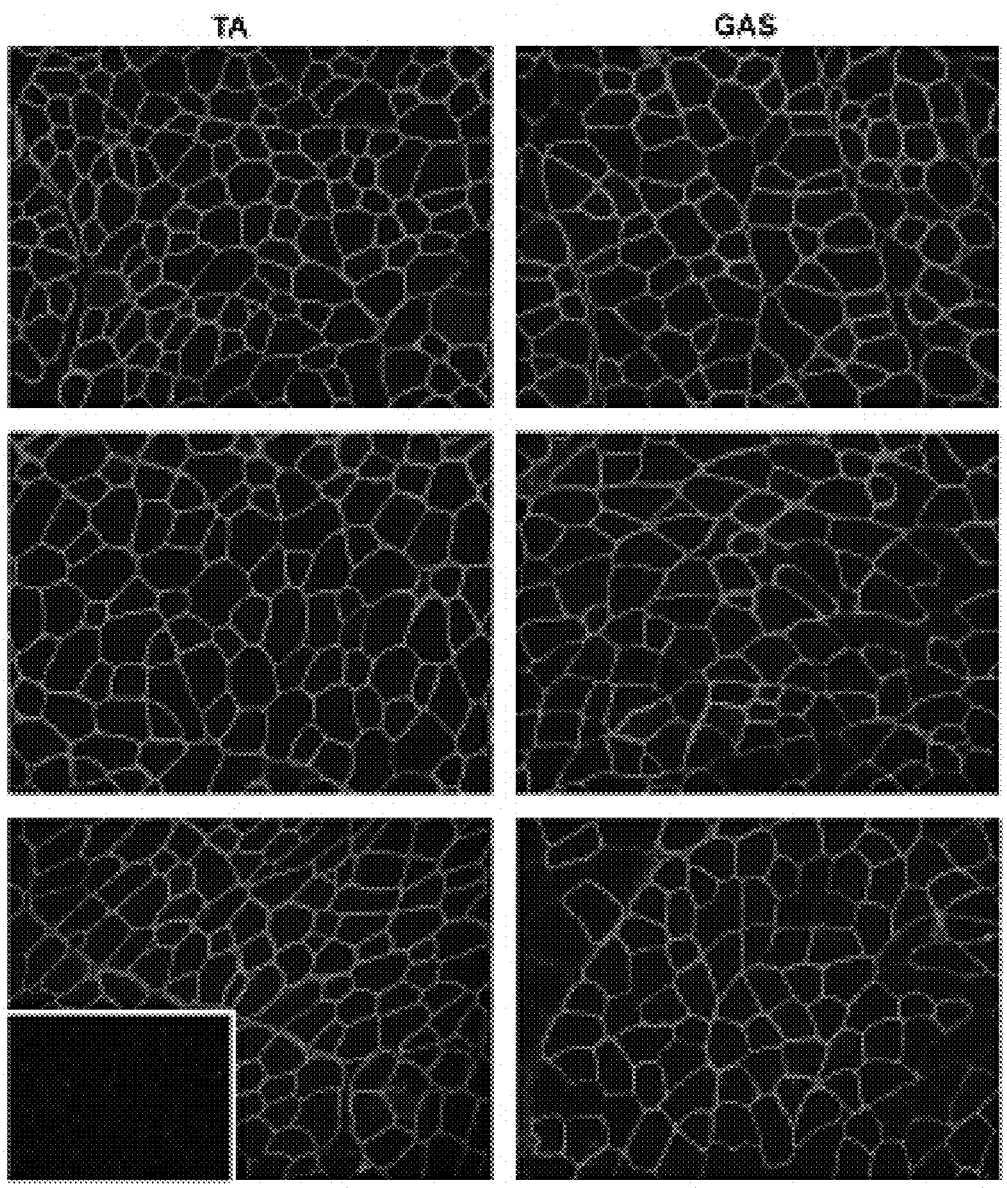
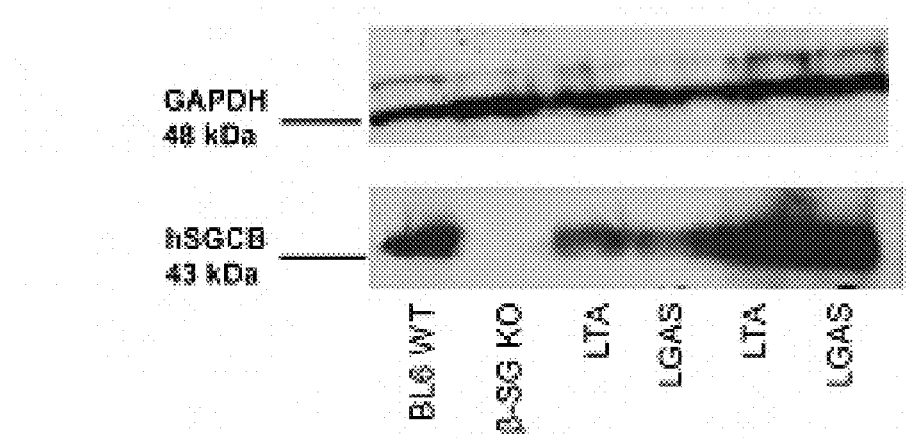

scAAVrh.74.MHCK7.hSGCB scAAV.MHCK7.hSGCB cassette

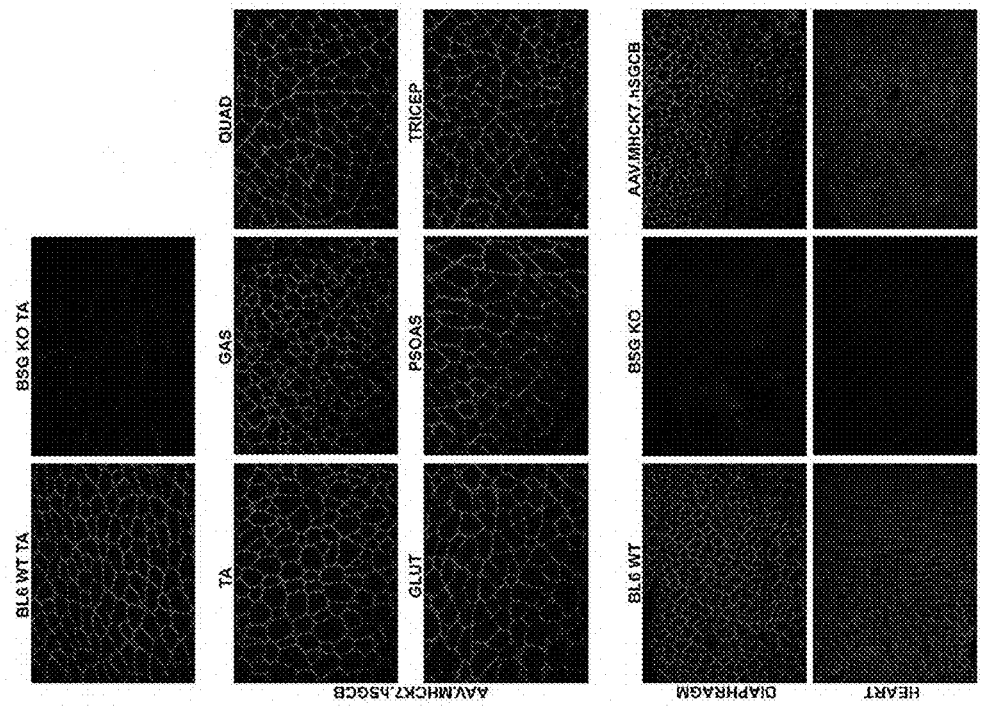
Figure 12B
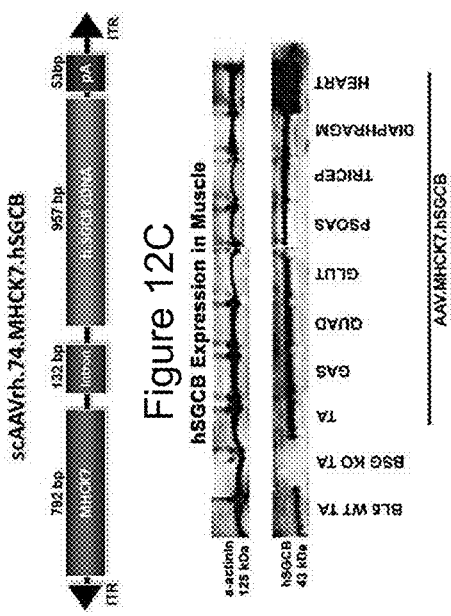
Figure 12A
Figure 12C
Figure 12D

Figure 16 scAAVrh.74.CMV.miR29c

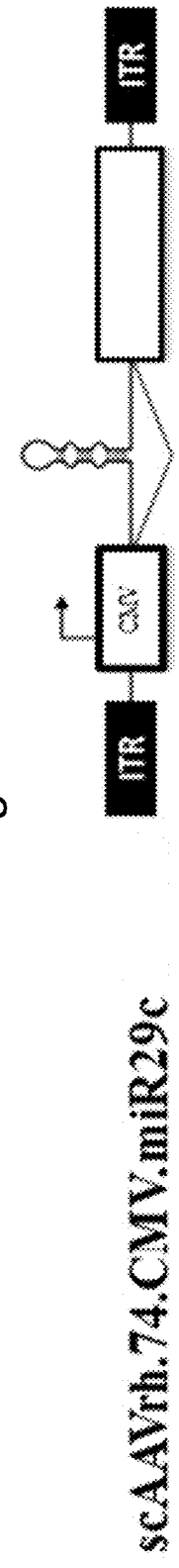

SEQ ID NO: 9: miR-29C IN A miR-30 BACKBONE

GGCCGGCCtgtttgaatgaggcttcagtacttttacagaatCGTTGCCTGCACATCTTGGAAACACTTGCTGGGATTAC
TTCTTCAGGTTAACCCAACAGAAGGCTCGAGAAGGTATATGCTTGACAGTGAGCGCAACC
GATTCAAATGGTGCTAGAGCTAGACCACAGATGTCTAGCACCATTGAAATCGGTTATGCCTA
CTGCCCTCGGAATTCAAGGGGCTACTTTAGGAGCAATTATCTGTTGTTACTAAAACTGAATACCTT
GCTATCTCTTTGATACATTGGGCCGGCC Figure 18
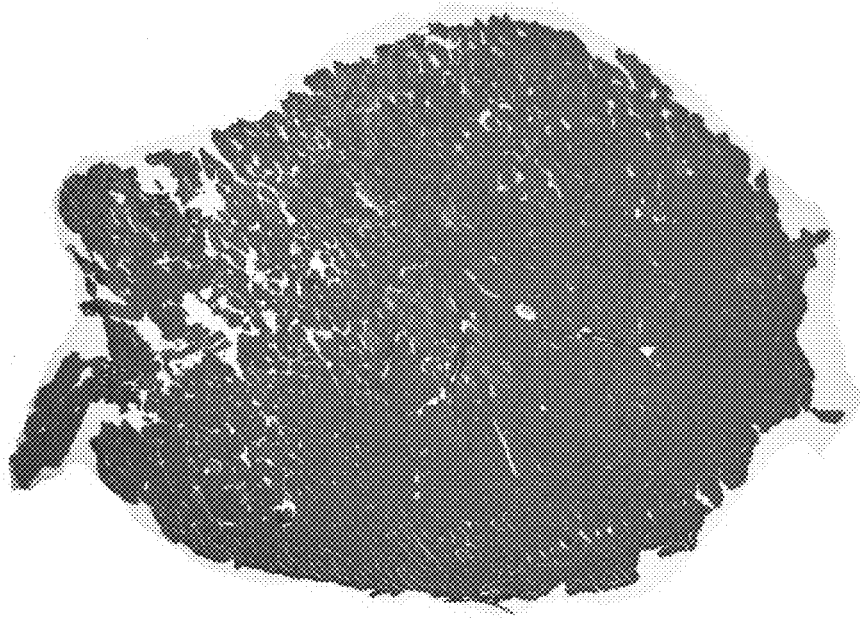
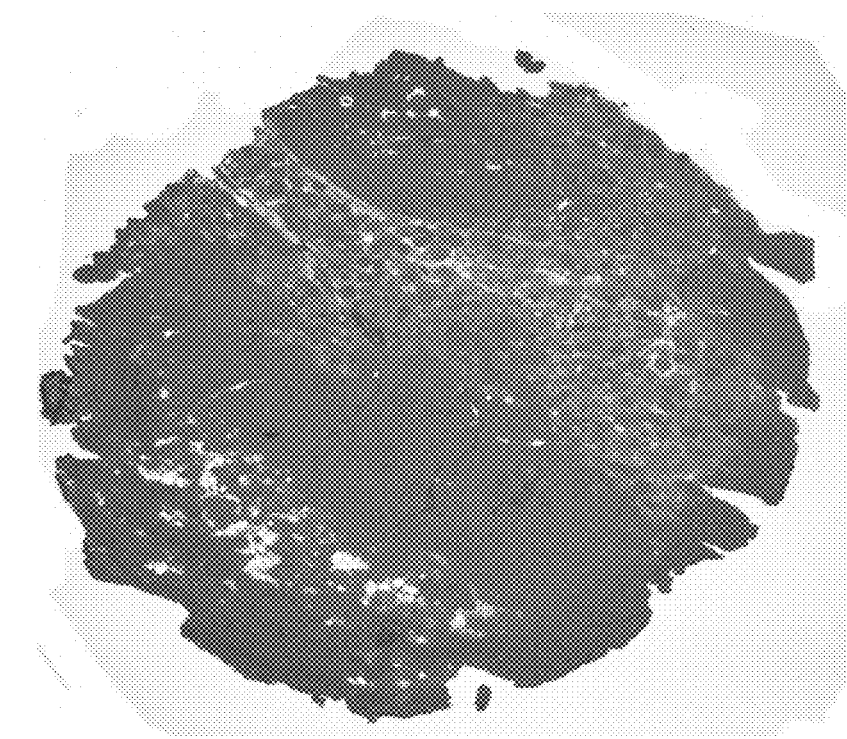

ADENO-ASSOCIATED VIRUS VECTOR DELIVERY OF B-SARCOGLYCAN AND MICRORNA-29 AND THE TREATMENT OF MUSCULAR DYSTROPHY

This application claims priority benefit of U.S. Provisional Application No. 62/323,333 filed Apr. 15, 2016 and U.S. Provisional Application No. 62/433,548, filed Dec. 13, 2016, both of which are incorporated by reference herein in its entirety.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 50622A_Seqlisting.txt; Size: 21,466 bytes, created: Apr. 13, 2017.

FIELD OF THE INVENTION

Described herein are therapy vectors such as AAV vectors expressing β-sarcoglycan and method of using these vectors to reduce and prevent fibrosis in subjects suffering from a muscular dystrophy. The invention also provides for combination gene therapy methods comprising the administration of a first AAV vector expressing β-sarcoglycan and a second AAV vector expressing miR-29 to reduce and prevent fibrosis in patients suffering from muscular dystrophy.

BACKGROUND

Limb-girdle muscular dystrophy (LGMD) type 2E (LGMD2E) is an autosomal recessive disorder resulting from mutations in the gene encoding β-sarcoglycan (SGCB), causing loss of functional protein.(1) LGMD2E represents a relatively common and severe form of LGMD in the United States with worldwide reports of incidence of 1/200,000-1/350,000.(2) The absence of β-sarcoglycan leads to a progressive dystrophy with chronic muscle fiber loss, inflammation, fat replacement and fibrosis, all resulting in deteriorating muscle strength and function. (3,4) As a complex, the sarcoglycans (α-, β, γ-, δ-), ranging in size between 35 and 50 kD,(5) are all transmembrane proteins that provide stability to the sarcolemma offering protection from mechanical stress during muscle activity.(3) Loss of β-sarcoglycan in LGMD2E usually results in varying degrees of concomitant loss of other sarcoglycan proteins contributing to the fragility of the muscle membrane leading to loss of myofibers.1 Although the range of clinical phenotype of LGMD2E varies, diagnosis typically occurs before age 10 and with loss of ambulation occurring by mid to late teens.(1,6,7) Patients present with elevated serum creatine kinase (CK), proximal muscle weakness, difficulty arising from the floor and progressive loss of ambulation. Cardiac involvement occurs in as many as fifty percent of cases.

Adeno-associated virus (AAV) is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in see U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics.

An emerging form of therapy for LGMD2E is viral-mediated gene delivery to restore wild-type protein to affected muscle resulting in restoration of muscle function. Considering that a subset of patients can develop cardiomyopathy, (8, 9, 10, 13) this would have to be considered in the long-term care of these patients. In previous reports, the sgcb-null mouse was well characterized. Araishi et al. (3) developed the β-sarcoglycan-deficient mouse with accompanying loss of all of the sarcoglycans as well as sarcospan, with at least minor preservation of merosin, the dystroglycans and dystrophin, reproducing the clinical picture seen in LGMD2E. The histological changes in this animal model were also a prototype for the clinical counterpart, including the prominence of skeletal muscle fibrosis.(14) Dressman et al. (25) injected the transverse abdominal muscle using rAAV2.CMV.SGCB. Expression persisted for 21 months and muscle fibers were protected from recurrent necrosis. The use of self-complementary AAV to enhance transgene expression,16 a muscle-specific promoter to better target skeletal muscle (20, 26) and the optimization of a human β-sarcoglycan gene (hSGCB) has also been described.

Functional improvement in patients suffering from LGMD and other muscular dystrophies require both gene restoration and reduction of fibrosis. There is a need for methods of reducing fibrosis that may be paired with gene restoration methods for more effective treatments of LGMD and other muscular dystrophies.

SUMMARY

Described herein are gene therapy vectors, e.g. AAV, expressing the β-sarcoglycan gene and methods of delivering β-sarcoglycan to the muscle to reduce and/or prevent fibrosis; and/or to increase muscular force, and/or to treat a β-sarcoglycanopathy in a mammalian subject suffering from muscular dystrophy.

In addition, the invention provides for combination therapies and approaches using gene therapy vectors to deliver β-sarcoglycan to address the gene defect observed in LGMD2E and gene therapy vectors delivering miR-29 to further suppress fibrosis.

In one aspect, described herein is a recombinant AAV vector comprising a polynucleotide sequence encoding β-sarcoglycan. In some embodiments, the polynucleotide sequence encoding β-sarcoglycan comprises a sequence e.g. at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence set forth in SEQ ID NO: 1 and encodes protein that retains β-sarcoglycan activity. In some embodiments, the polynucleotide sequence encoding β-sarcoglycan comprises the nucleotide sequence set forth in SEQ ID NO: 1. In some embodiments, the polynucleotide sequence encoding β-sarcoglycan consists the nucleotide sequence set forth in SEQ ID NO: 1.

In another aspect, a recombinant AAV vector described herein comprises a polynucleotide sequence encoding β-sarcoglycan that is at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the amino acid sequence of SEQ ID NO: 2, and the protein retains β-sarcoglycan activity.

In another aspect, described herein is a recombinant AAV vector comprising a polynucleotide sequence encoding functional β-sarcoglycan that comprises a nucleotide sequence that hybridizes under stringent conditions to the nucleic acid sequence of SEQ ID NO: 1, or a complement thereof.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO4, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

In another aspect, the recombinant AAV vectors described herein may be operably linked to a muscle-specific control element. For example the muscle-specific control element is human skeletal actin gene element, cardiac actin gene element, myocyte-specific enhancer binding factor (MEF) element, muscle creatine kinase (MCK), tMCK (truncated MCK), myosin heavy chain (MHC) control element, MHCK7 (a hybrid version of MHC and MCK), C5-12 (synthetic promoter), murine creatine kinase enhancer element, skeletal fast-twitch troponin C gene element, slow-twitch cardiac troponin C gene element, the slow-twitch troponin I gene element, hypoxia response element (HRE), steroid-inducible element or glucocorticoid response element (GRE).

In some embodiments, the muscle-specific promoter is MHCK7 (SEQ ID NO: 4). An exemplary rAAV described herein is pAAV.MHCK7.hSCGB which comprises the nucleotide sequence of SEQ ID NO: 3; wherein the MCHK7 promoter spans nucleotides 130-921, a SV40 chimeric intron spans nucleotides 931-1078, the β-sarcoglycan sequence spans nucleotides 1091-2047 and the poly A spans nucleotides 2054-2106.

In some embodiments, the muscle-specific promoter is tMCK (SEQ ID NO: 6). An exemplary rAAV described herein is pAAV.tMCK.hSCGB which comprises the nucleotide sequence of SEQ ID NO: 5; wherein the tMCK promoter spans nucleotides 141-854, an SV40 chimeric intron spans nucleotides 886-1018, the β-sarcoglycan sequence spans nucleotides 1058-2014 and the poly A spans nucleotides 2021-2073.

The AAV can be any serotype, for example AAV1, AAV2, AAV3, AAV4, AAV5, AAV6, AAV7, AAV8, AAV9, AAV-10, AAV-11, AAV-12, AAV-13 and AAV rh.74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

Compositions comprising any of the rAAV vectors described herein are also contemplated.

Methods of producing a recombinant AAV vector particle comprising culturing a cell that has been transfected with any recombinant AAV vector described herein and recovering recombinant AAV particles from the supernatant of the transfected cells are also provided. Viral particles comprising any of the recombinant AAV vectors described herein are also contemplated Methods of reducing fibrosis in a mammalian subject in need thereof is also provided. In this regard, the method comprises administering a therapeutically effective amount of an AAV vector described herein (or composition comprising an AAV vector described herein) to the mammalian subject. In some embodiments, the mammalian subject suffers from muscular dystrophy. In some embodiments, administration of an AAV vector described herein (or composition comprising an AAV vector described herein) reduces fibrosis in skeletal muscle or in cardiac muscle of the subject. These methods may further comprise the step of administering a second recombinant AAV vector comprising a polynucleotide sequence comprising miR-29c.

The term "muscular dystrophy" as used herein refers to a disorder in which strength and muscle bulk gradually decline. Non-limiting examples of muscular dystrophy diseases may include Becker muscular dystrophy, tibial muscular dystrophy, Duchenne muscular dystrophy, Emery-Dreifuss muscular dystrophy, facioscapulohumeral muscular dystrophy, sarcoglycanopathies, congenital muscular dystrophy such as congenital muscular dystrophy due to partial LAMA2 deficiency, merosin-deficient congenital muscular dystrophy, type 1D congenital muscular dystrophy, Fukuyama congenital muscular dystrophy, limb-girdle type 1A muscular dystrophy, limb-girdle type 2A muscular dystrophy, limb-girdle type 2B muscular dystrophy, limb-girdle type 2C muscular dystrophy, limb-girdle type 2D muscular dystrophy, limb-girdle type 2E muscular dystrophy, limb-girdle type 2F muscular dystrophy, limb-girdle type 2G muscular dystrophy, limb-girdle type 2H muscular dystrophy, limb-girdle type 2I muscular dystrophy, limb-girdle type 2I muscular dystrophy, limb-girdle type 2J muscular dystrophy, limb-girdle type 2K muscular dystrophy, limb-girdle type IC muscular dystrophy, rigid spine muscular dystrophy with epidermolysis bullosa simplex, oculopharyngeal muscular dystrophy, Ullrich congenital muscular dystrophy, and Ullrich scleroatonic muscular dystrophy. In some embodiments, the subject is suffering from limb-girdle muscular dystrophy. In some embodiments, the subject us suffering from limb-girdle muscular dystrophy type 2E (LGMD2E).

The term "fibrosis" as used herein refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include collagen, e.g. collagen 1, collagen 2 or collagen 3, and fibronectin.

In another aspect, described herein is a method of increasing muscular force and/or muscle mass in a mammalian subject comprising administering a therapeutically effective amount of an AAV vector described herein (or composition comprising an AAV vector described herein) to the mammalian subject.

In any of the methods of the invention, the subject may be suffering from muscular dystrophy such as limb-girdle muscular dystrophy or any other dystrophin-associated muscular dystrophy.

Also provided is a method of treating muscular dystrophy in a mammalian subject comprising administering a therapeutically effective amount of an AAV vector described herein (or composition comprising an AAV vector described herein) to the mammalian subject. In some embodiments, the muscular dystrophy is limb-girdle muscular dystrophy. Any of the methods described herein may further comprise the step of administering a second recombinant AAV vector comprising a polynucleotide sequence comprising miR-29c.

Combination therapies are also contemplated. In this regard, any of the foregoing methods described here may further comprise administering a second recombinant AAV vector comprising a polynucleotide sequence comprising miR-29c. In some embodiments, the polynucleotide comprising miR-29c is operably linked operably linked to a muscle-specific control element. For example the muscle-specific control element is human skeletal actin gene element, cardiac actin gene element, myocyte-specific enhancer binding factor (MEF) element, muscle creatine kinase (MCK), tMCK (truncated MCK), myosin heavy chain (MHC) control element, MHCK7 (a hybrid version of MHC and MCK), C5-12 (synthetic promoter), murine creatine kinase enhancer element, skeletal fast-twitch troponin C gene element, slow-twitch cardiac troponin C gene element, the slow-twitch troponin I gene element, hypoxia-responsive element (HRE), steroid-inducible element or glucocorticoid response element (GRE). In some embodiments, the second recombinant vector comprises a polynucleotide sequence set forth in SEQ ID NO: 9 or SEQ ID NO: 8, as described in U.S. Provisional Application No. 62/323,163 (the disclosure of which is incorporated herein by reference in its entirety).

In combination therapy methods described herein in which both an rAAV vector expressing β-sarcoglycan and an rAAV vector expressing miR-29c are administered to the mammalian subject, the rAAV vectors may be administered concurrently, or administered consecutively with the rAAV vector expressing β-sarcoglycan being administered immediately before or after the rAAV expressing miR-29c. Alternatively, the AAV vector expressing β-sarcoglycan is administered within about 1-24 hours (e.g., 1, 2, 3, 4, 5, 6, 7, 8, 9, 10, 11, 12, 13, 14, 15, 16, 17, 18, 19, 20, 21, 22, 23 or 24 hours) after administering the rAAV expressing miR-29 or the methods of the invention are carried out wherein the AAV vector expressing the β-sarcoglycan is administered within about 1-24 hours (e.g., 1, 2, 3, 4, 5, 6, 7, 8, 9, 10, 11, 12, 13, 14, 15, 16, 17, 18, 19, 20, 21, 22, 23 or 24 hours) before administering the rAAV expressing miR-29. In some embodiments, the AAV vector expressing β-sarcoglycan is administered within about 1-5 hours (e.g., 1, 2, 3, 4 or 5 hours) after administering the rAAV expressing miR-29 or the methods of the invention are carried out wherein the AAV vector expressing the β-sarcoglycan is administered within about 1-5 hours (e.g., 1, 2, 3, 4 or 5 hours) before administering the rAAV expressing miR-29c.

In any of the methods of the invention, the rAAV is administered by intramuscular injection or intravenous injection. In addition, in any of the method of the invention, the rAAV is administered systemically, such as parental administration by injection, infusion or implantation.

The compositions of the invention are formulated for intramuscular injection or intravenous injection. In addition, the compositions of the invention are formulated for systemic administration, such as parental administration by injection, infusion or implantation.

In addition, any of the compositions formulated for administration to a subject suffering from muscular dystrophy (such as limb-girdle muscular dystrophy or any other dystrophin-associated muscular dystrophy). In some embodiments, the composition may further comprise a second recombinant AAV vector comprising a polynucleotide sequence set forth in SEQ ID NO: 9 or SEQ ID NO: 8.

In any of the uses of the invention, the medicament is formulated for intramuscular injection or intravenous injection. In addition, in any of the uses of the invention, the medicament is formulated for systemic administration, such as parental administration by injection, infusion or implantation. In addition, any of the medicaments may be prepared for administration to a subject suffering from muscular dystrophy (such as limb-girdle muscular dystrophy or any other dystrophin associated muscular dystrophy). In some embodiments, the medicament may further comprise a second recombinant AAV vector comprising a polynucleotide sequence set forth in SEQ ID NO: 9 or SEQ ID NO: 8.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention.

BRIEF DESCRIPTION OF THE FIGURES

FIGS. 2A-2E shows the histological analysis of β-SG-deficient treated skeletal muscle. scAAVrh.74.hSGCB treatment normalizes histological parameters of sgcb$^{-/-}$ mice. Hematoxylin & Eosin staining and Picrosirius Red staining were performed on TA muscle from sgcb$^{-/-}$ mice along with normal control C57/BL6 mice and scAAVrh.74.hSGCB-treated mice followed by quantification of histological parameters and % collagen staining. (a) H&E staining shows the presence of centrally nucleated fibers, inflammatory cells and large fiber diameter distribution in β-SG-deficient muscle and an improvement in histopathology following gene transfer. (b) Pircrosirius Red staining shows a decrease in red collagen staining in treated muscle. (c) Quantification of centrally nucleated fibers showing a decrease following treatment (P<0.0005, one-way ANOVA) and (d) representation of fiber size distribution and increase in average fiber size of TA muscle from C57/BL6 controls and sgcb$^{-/-}$ mice compared with treated mice (P<0.0001, one-way ANOVA). (e) Quantification of % collagen in TA muscle from C57/BL6 controls and sgcb$^{-/-}$ mice compared with sgcb$^{-/-}$ treated mice (P<0.0001, one-way ANOVA). 100 μm scale bar shown for x20 images. *P<0.001; **P<0.0001.

FIGS. 4A-4C shows the results of the analysis of aged mice treated intramuscularly with scAAVrh.74.tMCK.hSGCB. (a) Immunofluorescence staining of TA muscle from 6-month-old treated sgcb$^{-/-}$ mice 12 weeks post injection (n=5, 5 male) shows sarcolemmal expression of the SGCB transgene at levels averaging 80% in injected mice compared with untreated (n=4, 4 male). (b) Picrosirius red staining of the treated and untreated TA muscle. (c) Quantitation of collagen present in the Picrosirius red stained tissue shows a significant reduction in the amount of collagen following treatment with rAAVrh.74.tMCK.hSGCB (P<0.0001, one-way ANOVA). 100 μm scale bar shown for x20 images. ****P<0.0001.

FIGS. 5A-5C show the results of vascular delivery of scAAVrh.74.hSGCB. Four (n=5, 5 male) and five (n=4, 2 male, 2 female) weeks β-SG-deficient mice were treated with vector via the femoral artery to deliver the vector to the lower limb muscles. At a dose of $5\times10^{11}$ vg, β-SG expression was 90.6±2.8% in the TA and 91.8±4.7% in the GAS of treated mice accompanied by improvements in histopathology that resulted in significant improvement in specific force compared with untreated animals even following an injury paradigm. (a) β-SG protein expression from three representative mice. Muscle from a β-SG KO untreated mouse is shown for comparison in the inset (lower right). ×20 Images are shown. Expression in treated muscles confirmed via western blot and gamma-tubulin is shown as a loading control. (b) Histopathology is significantly improved following high dose treatment. Upper panels-treated TA and gastrocnemius muscles. Bottom panels-untreated β-SG-deficient control muscle. 100 μm scale bar shown for ×20 images. (c) Percentage of specific force retained in EDL muscle following 10 cycles of eccentric contraction-induced injury. Treatment with $5\times10^{11}$ vg of AAVrh.74.hSGCB led to significant improvement in force that was equivalent to WT (normal) control muscle (P<0.05, one-way ANOVA). *P<0.05.

FIG. 12A-D depicts restoration of SGCB expression following intravenous delivery of scAAVrh.74.MHCK7.hSGCB. (A) scAAVrh.74.MHCK7.hSGCB cassette. (b) Immunofluorescence imaging 6 months post-injection of skeletal muscles, diaphragm, and heart from sgcb$^{-/-}$ mice intravenously injected with 1e12 vg total dose scAAVrh.74.MHCK7.hSGCB. Representative images of skeletal muscles displaying an average of 98.13±0.31% transduction. 20× images are shown. Representative images of heart tissue displaying high levels of hSGCB transgene expression. 10× images are shown. (c) Western blotting of all muscles from one treated sgcb$^{-/-}$ mouse confirming hSGCB transgene expression. (d) Western blotting for hSGCB expression in hearts of five sgcb$^{-/-}$ treated mice with densitometry quantification showing overexpression of hSGCB up to 72.0% of BL6 WT levels.

FIG. 16 provides a schematic of rAAV vector scAACrh.74.CMV.miR29c and the nucleotide sequence of the miR-29c in a natural miR-30 backbone.

FIG. 18 provides representative images of scanned full sections of untreated and AAVrh.74.CMV.miR29C treated tibialis anterior muscles stained with Sirius Red which stains for collagen 1 and 3. Quantification is shown in FIG. 17.

DETAILED DESCRIPTION

Figure 1A:
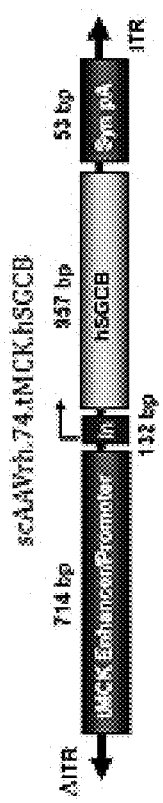
FIGS. 1A-1D demonstrate that AAV mediated β-sarcoglycan expression restores dystrophin-associated proteins and protects membrane integrity. (a) Self-complementary AAV vector containing the codon-optimized human β-sarcoglycan gene (hSGCB) driven by the muscle-specific tMCK promoter. The cassette also contains a chimeric intron to augment processing and polyadenylation signal for stability. (b) Immunofluorescence staining with anti-β-SG antibody shows high levels of sarcolemmal staining of the SGCB transgene in 5-week-old mice both 6 and 12 weeks post injection. x20 images shown. Percentage of fibers expressing beta-sarcoglycan per TA muscle averaged 88.4±4.2% after 6 weeks (n=9, 4 male, 5 female) and 76.5±5.8% after 12 weeks (n=6, 4 male, 2 female). Protein expression confirmed in the western blot with gamma-tubulin blot shown for a loading control. (c) AAV delivery of β-sarcoglycan leads to restoration of other members of the sarcoglycan complex; α-sarcoglycan, dystrophin. x20 images. (d) scAAVrh.74.hSGCB protects sgcb$^{-/-}$ membranes from damage. Image showing a large area of Evans blue-positive fibers (red) juxtaposed to a cluster of β-sarcoglycan-positive fibers that have been protected from Evans blue dye incorporation. x40 image is shown.

The present disclosure is based on the discovery that administration of an AAV vector comprising a polynucleotide expressing β-sarcoglycan results in a reduction or complete reversal of muscle fibrosis in a limb-girdle muscular dystrophy animal model. As demonstrated in the Examples, administration of the AAV vector described herein resulted in the reversal of dystrophic features including fewer degenerating fibers, reduced inflammation and improved functional recovery by protection against eccentric contraction with increased force generation.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV

Recombinant AAV genomes of the invention comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). As noted in the Background section above, the nucleotide sequences of the genomes of various AAV serotypes are known in the art. To promote skeletal muscle specific expression, AAV1, AAV5, AAV6, AAV8 or AAV9 may be used.

DNA plasmids of the invention comprise rAAV genomes. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. Embodiments include, but are not limited to, the rAAV named pAAV.MHCK7.hSCGB which comprises the polynucleotide sequence set forth in SEQ ID NO: 3; and pAAV.tMCK.hSCGB which comprises the polynucleotide sequence set forth in SEQ ID NO: 5.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the invention contemplates compositions comprising rAAV of the present invention. Compositions described herein comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-formig counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is muscular dystrophy, such as limb-girdle muscular dystrophy Combination therapies are also contemplated by the invention. Combination as used herein includes both simultaneous treatment or sequential treatments. Combinations of methods of the invention with standard medical treatments (e.g., corticosteroids) are specifically contemplated, as are combinations with novel therapies.

A therapeutically effective amount of the rAAV vector is a dose of rAAV ranging from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e13 vg/kg to about 1e14 vg/kg, or about 1e13 vg/kg to about 2e14 vg/kg, or 1e13 vg/kg to about 3e14 vg/kg, or about 1e13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg. The invention also comprises compositions comprising these ranges of rAAV vector.

For example, a therapeutically effective amount of rAAV vector is a dose of 1e13 vg/kg, about 2e13 vg/kg, about 3e13 vg/kg, about 4e13 vg/kg, about 5e13 vg/kg, about 6e13 vg/kg, about 7e13 vg/kg, about 8e13 vg/kg, about 9e13 vg/kg, about 1e14 vg/kg, about 2e14 vg/kg, about 3e14 vg/kg, about 4e14 vg/kg and 5e14 vg/kg. The invention also comprises compositions comprising these doses of rAAV vector.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the β-sarcoglycan.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of β-sarcoglycan. The present invention thus provides methods of administering/delivering rAAV which express β-sarcoglycan to a mammalian subject, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., Science, 251: 761-766 (1991)], the myocyte-specific enhancer binding factor MEF-2 [Cserjesi and Olson, Mol Cell Biol 11: 4854-4862 (1991)], control elements derived from the human skeletal actin gene [Muscat et al., Mol Cell Biol, 7: 4089-4099 (1987)], the cardiac actin gene, muscle creatine kinase sequence elements [See Johnson et al., Mol Cell Biol, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., Proc Natl Acad Sci USA, 88: 5680-5684 (1991)), steroid-inducible elements and promoters including the glucocorticoid response element (GRE) (See Mader and White, Proc. Natl. Acad. Sci. USA 90: 5603-5607 (1993)), and other control elements.

Muscle tissue is an attractive target for in vivo DNA delivery, because it is not a vital organ and is easy to access. The invention contemplates sustained expression of miR-NAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of a polynucleotide of interest (e.g., a polynucleotide sequence encoding β-sarcoglycan) to a recipient cell either in vivo or in vitro, via a replication-deficient rAAV described resulting in expression of β-sarcoglycan by the recipient cell.

Thus, also described herein are methods of administering an effective dose (or doses, administered essentially simultaneously or doses given at intervals) of rAAV that encode β-sarcoglycan to a mammalian subject in need thereof.

All publications and patents mentioned herein are hereby incorporated by reference in their entirety as if each individual publication or patent was specifically and individually indicated to be incorporated by reference. In case of conflict, the present application, including any definitions herein, will control.

The invention is further described in the following Examples, which do not limit the scope of the invention described in the claims.

EXAMPLES

Materials and Methods

Animal models—All procedures were approved by The Research Institute at Nationwide Children's Hospital Institutional Animal Care and Use Committee (protocol AR12-00040). B6.129-Sgcb$^{tm1Kcam/1J}$ heterozygous mice were purchased from the Jackson Laboratory (Bar Harbor, Me., USA; Strain #006832). Sgcb$^{-/-}$ mice were generated by breeding heterozygous mice. KO mice were bred and maintained as homozygous animals in standardized conditions in the Animal Resources Core at the Research Institute at Nationwide Children's Hospital. Mice were maintained on Teklad Global Rodent Diet (3.8z5 fiber, 18.8% protein, 5% fat chow) with a 12:12-h dark:light cycle. Identification of SGCB$^{-/-}$ mice was performed by genotyping using PCR. All animals were housed in standard mouse cages with food and water ad libitum.

Beta-sarcoglycan gene construction. The full-length human beta-sarcoglycan cDNA (GenBank Accession No. NM_0034994.3) was codon optimized and synthesized by GenScript Inc, Piscataway, N.J., USA. Codon optimization through GenScript uses an algorithm that takes into account parameters that include transcription, mRNA processing and stability, translation and protein folding to design a cDNA sequence that results in maximum expression in muscle tissue (www.genscript.com).

For the pAAV.tMCK.hSGCB construct, the cDNA was then cloned into a plasmid containing AAV2 ITRs and the cassette included a consensus Kozak sequence (CCACC), an SV40 chimeric intron and a synthetic polyadenylation site (53 bp). The recombinant tMCK promoter was a gift from Dr Xiao Xiao (University of North Carolina). It is a modification of the previously described CK6 promoter27 and includes a modification in the enhancer upstream of the promoter region containing transcription factor binding sites. The enhancer is composed of two E-boxes (right and left). The tMCK promoter modification includes a mutation converting the left E-box to a right E-box (2R modification) and a 6-bp insertion (S5 modification). The pAAV.tMCK.hSGCB vector was constructed by ligation of 1040 bp KpnI/XbaI fragment from pUC57-BSG (Genscript Inc.) into the KpnI/XbaI sites of pAAV. tMCK.hSGCA.26

The pAAV.MHCK7.hSGCB vector was constructed by removing the tMCK promoter and SV40 chimeric intron with NotI/KpnI sites and inserting a PCR amplified fragment containing the MHCK7 promoter and identical SV40 chimeric intron with NotI/KpnI sites. MHCK7 is an MCK based promoter which utilizes a 206-bp enhancer taken from ~1.2 kb 5' of the transcription start site within the endogenous muscle creatine kinase gene with a proximal promoter (enh358MCK, 584-bp)[3,12]. The MHCK7 promoter itself contains this modified CK7 cassette from the MCK family of genes ligated to a 188-bp α-MyHC (α-myosin heavy chain) enhancer 5' of the CK portion to enhance cardiac expression[12]. The creatine kinase portion of the promoter (CK) is 96% identical between tMCK and MHCK7. Finally, the pAAV.MHCK7.hSGCB vector was constructed by ligation of the 960 bp NotI/KpnI MHCK7+Intron fragment from pAAV.MHCK7.DYSF5'DV44 into the NotI/KpnI sites of pAAV.tMCK.hSGCB (Pozgai et al., Gene Ther. 23: 57-66, 2016)

rAAV production. A modified cross-packaging approach, previously reported by Rodino-Klapac et al. (J. Trans. Med. 5:45, 2007), was used to produce the rAAV vector. Here, a triple transfection method with CaPO$_4$ precipitation in HEK293 cells allows for AAV2 ITRs to be packaged into a different AAV capsid serotype. (28,29) The production plasmids were (i) pAAV.tMCK.hSGCB or pAAV.MHCK7.hSGCB, (ii) rep2-caprh.74 modified AAV helper plasmids encoding cap serotype 8-like isolate rh.74 and (iii) an adenovirus type 5 helper plasmid (pAdhelper) expressing adenovirus E2A, E4 ORF6 and VA I/II RNA genes. Vectors were purified and encapsidated vg titer (utilizing a Prism 7500 Taqman detector system; PE Applied Biosystems, Carlsbad, Calif., USA) was determined as previously described. 30 The primer and fluorescent probe targeted the tMCK promoter and were as follows: tMCK forward primer, 5'-ACC CGA GAT GCC TGG TTA TAA TT-3' (SEQ ID NO: 10); tMCK reverse primer, 5'-TCC ATG GTG TAC AGA GCC TAA GAC-3' (SEQ ID NO: 11); and tMCK probe, 5'-FAM-CTG CTG CCT GAG CCT GAG CGG TTA C-TAMRA-3' (SEQ ID NO: 12). The primer and fluorescent probe targeted the MHCK7 promoter and were as follows: MHCK7 forward primer, 5'-CCA ACA CCT GCT GCC TCT AAA-3' (SEQ ID NO: 16); MHCK7 reverse primer, 5'-GTC CCC CAC AGC CTT GTT C-3' (SEQ ID NO: 17); and MHCK7 probe, 5'-FAM-TGG ATC CCC-Zen-TGC ATG CGA AGA TC-3IABKFQ-3' (SEQ ID NO: 18).

Intramuscular Gene delivery. For intramuscular injection, mice were anesthetized and maintained under 1-4% isoflurane (in $O^2$). The anterior compartment of the lower left limb of 4- to 6-week-old SGCB$^{-/-}$ mice was cleaned with 95% EtOH then the transverse abdominal (TA) muscle was injected with $3\times10^{11}$ vg of scAAVrh.74.tMCK.hSGCB diluted in saline in a 30-µl volume using a 30 gauge ultra-fine insulin syringe. The contralateral muscle was left untreated to serve as a control. TA muscle from both limbs was removed at either 6 (n=9, 4 male, 5 female) or 12 (n=6, 4 male, 2 female) weeks post injection to assess gene transfer efficiency. In experiments involving 6-month-old mice (n =5, 5 male), treatment consisted of intramuscular injection into the left TA with $3\times10^{11}$ vg of scAAVrh.74.tMCK.hSCGB. For isolated limb perfusion experiments, sgcb$^{-/-}$ mice were perfused at 4 (n=5, 5 male) and 5 (n=4, 2 male, 2 female) weeks of age with $5>10^{11}$ vg of scAAVrh.74.tMCK.hSCBB by injection into the femoral artery as previously described.19 Animals were euthanized and muscles were analyzed 8 weeks post gene transfer.

Systemic Gene Delivery: Systemic delivery was achieved through injection of vector into the tail vein of sgcb$^{-/-}$ mice. Mice were injected with $1\times10^{12}$ vg of scAAVrh.74.MHCK7.hSGCB diluted in saline in a 212 µL volume using a 30 gauge ultra-fine insulin syringe. Mice were restrained in a holding tube placing the tail back through tail slot to warm it up in order dilate the blood vessels for ease of injection. After locating the artery down the center line of the tail, the injection was performed in one of the purple/blue lateral veins that run alongside the tail artery. All treated mice were injected at 4-5 weeks of age and euthanized 6-months post-injection.

EDL force generation and protection from eccentric contractions. A physiological analysis of the EDL muscles from mice treated by isolated perfusion (ILP) was performed. The EDL muscle from both lower hind limbs of treated mice was dissected at the tendons and subjected to a physiology protocol to assess function that was previously described by our laboratory and others (19,31) with some adaptations. During the eccentric contraction protocol, a 5% stretch-re-lengthening procedure executed between 500 and 700 ms (5% stretch over 100 ms, followed by return to optimal length in 100 ms). Following the tetanus and eccentric contraction protocol, the muscle was removed, wet-weighed, mounted on chuck using gum tragacanth, and then frozen in methyl-butane cooled in liquid nitrogen.

TA force generation and protection from eccentric contractions. A protocol to assess functional outcomes in the TA muscle was performed on muscles extracted from mice treated by IM injection. This TA procedure is outlined in several previous studies.(32,33) After the eccentric contractions, the mice were then euthanized and the TA muscle was dissected out, weighed and frozen for analysis. Analysis of the data was performed blindly but not randomly.

Immunofluorescence. Cryostat sections (12 µm) were incubated with a monoclonal human beta-sarcoglycan primary antibody (Leica Biosystems, New Castle, UK; Cat. No. NCL-L-b-SARC) at a dilution of 1:50 in a block buffer (1×TBS, 10% Goat Serum, 0.1% Tween) for 1 h at room temperature in a wet chamber. Sections were then washed with TBS three times, each for 20 min and re-blocked for 30 min. AlexaFluor 594 conjugated goat anti-mouse secondary IgG1 antibody (Life Technologies, Grand Island, N.Y., USA; Cat. No. A21125) was applied at a 1:250 dilution for 45 min. Sections were washed in TBS three times for 20 min and mounted with Vectashield mounting medium (Vector Laboratories, Burlingame, Calif., USA). Four random ×20 images covering the four different quadrants of the muscle section were taken using a Zeiss AxioCam MRCS camera. Percentage of fibers positive for beta-sarcoglycan staining (450% of muscle membrane staining intensity) was determined for each image and averaged for each muscle.

Western blot analysis. Tissue sections from the left treated TA muscle and the right contralateral TA muscle (20-20 micron thick) were collected into a micro-centrifuge and homogenized with 100 µl homogenization buffer (125 mM Tris-HCl, 4% SDS, 4 M urea) in the presence of 1 protease inhibitor cocktail tablet (Roche, Indianapolis, Ind., USA). After homogenization, the samples were centrifuged at 10,000 rpm for 10 min at 4° C. Protein was quantified on NanoDrop (Thermo Scientific, Waltham, Mass., USA). Protein samples (20 µg) were electrophoresed on a 3-8% polyacrylamide Tris-acetate gel (NuPage, Invitrogen, Carlsbad, Calif., USA) for 1 h 5 min at 150 V and then transferred onto a PVDF membrane (Amersham Biosciences, Piscataway, N.J., USA) for 1 h 15 min at 35 V. The membrane was blocked in 5% non-fat dry milk in TBST for 1 h, and then incubated with a rabbit polyclonal human beta-sarcoglycan antibody (Novus Biologicals, Littleton, Colo., USA; Cat. No. NBP-1-90300 1:100 or 1:250 dilution) and a 1:5000 of a monoclonal mouse gamma-tubulin antibody (Sigma-Aldrich, St Louis, Mo., USA; Cat. No. T6557) or a 1:5000 dilution of a mouse monoclonal mouse α-actinin antibody (Sigma-Aldrich, St Louis, Mo., USA; Cat. No. A7811). A 1:500 dilution of a rabbit polyclonal mouse cardiac troponin I antibody (Abcam, Cambridge, Mass.; Cat. No. ab47003) and a 1:1000 dilution of a rabbit monoclonal mouse vinculin antibody (Invitrogen, Frederick, Md.; Cat. No. 70062) were used. Anti-mouse (Millipore, Billerica, Mass., USA; Cat. No. AP308P) and anti-rabbit (Life Technologies; Cat. No. 656120) secondary-HRP antibodies were used for ECL immunodetection.

EBD assay. A dose of $3\times10^{10}$ vg of scAAVrh.74.tMCK.hSGCB was delivered to 4-week-old sgcb$^{-/-}$ mice to the left TA through an intramuscular injection. Four weeks post injection, mice were injected in the intraperitoneal cavity on the right side at 5 µl/g body weight of a filter sterilized 10 mg/ml EBD in 1× phosphate buffer solution. Mice were then killed 24 h post injection and tissues were harvested and sectioned. Sections were fixed in cold acetone for 10 min and then the immunofluorescence protocol was used to stain for human beta-sarcoglycan.

Morphometric analysis. Muscle fiber diameters and percentage of myofibers with centrally located nuclei were determined from TA and GAS muscles stained with hematoxylin and eosin (H&E). Four random ×20 images per section per animal were taken with a Zeiss AxioCam MRCS camera. Centrally nucleated fibers were quantified using the NIH ImageJ software (Bethesda, Md., USA). Fiber diameters were measured as the shortest diameter through the muscle fiber using Zeiss Axiovision LE4 software (Carl Zeiss Microscopy, Munich, Germany).

Biodistribution qPCR analysis. Taqman quantitative PCR was performed to quantify the number of vector genome copies present in targeted and untargeted contralateral muscle as well as non-targeted organs as previously described.(18,30) A vector-specific primer probe set was used to amplify a sequence of the intronic region directly downstream from the tMCK promoter that is unique and located within the scAAVrh.74.tMCK.hSGCB transgene cassette. The following primers and probe were used in this study: tMCK and MHCK7 intron Forward Primer 5'-GTG AGG CAC TGG GCA GGT AA-3' (SEQ ID NO: 13); tMCK and MHCK7 intron Reverse Primer 5'-ACC TGT GGA GAG AAA GGC AAA G-3' (SEQ ID NO: 14); and tMCK and MHCK7 intron Probe 5'-6FAM-ATC AAG GTT ACA AGA CAG-GTT TAA GGA GAC CAA TAG AAA-tamra-3' (IDT) (SEQ ID NO: 15). Copy number is reported as vector genomes per microgram of genomic DNA.

Immunohistochemistry for immune cell staining. Immunohistochemistry was used to identify immune cells. Frozen tissue sections on Fisherbrand Superfrost charged microscope slides were incubated with rat anti-mouse monoclonal antibodies using an anti-rat Ig HRP Detection kit (BD Pharmagen, San Jose, Calif., USA; Cat: 551013): CD3 (Cat: 555273), CD4 (Cat: 550280), CD8 (Cat: 550281) and Mac-3 for macrophages (Cat: 550292). All primary antibodies were diluted at 1:20 with phosphate-buffered saline. Positive immune staining was visualized using DAB chromagen diluted in DAB buffer with Streptavidin-HRP peroxidase ectastain ABC Peroxidase. Ten random ×40 images were taken for each muscle and each corresponding stain. The number of mono-nuclear cells was counted and expressed as total number per $mm^2$.

Picrosirius red stain and collagen quantification. Frozen sections placed onto Fisherbrand Superfrost charged microscope slides were fixed in 10% Neutral Buffered Formalin for 5 min, then rinsed in distilled water. Slides were then incubated in Solution A (Phosphomolydbic acid) from the Picrosirius Red Stain Kit (Polysciences Inc., Warrington, Pa., USA; Catalog #24901) for 2 min. After a thorough rinse in distilled water, the slides were placed in Solution B (Direct Red 80/2 4 6-Trinitrophenol) for 15 min, followed by an additional rinse in distilled water and then incubation in Solution C (0.1 N hydrochloride acid) for 2 min. Slides were counterstained for 2.5 min with 1% Fast Green in 1% Glacial Acetic Acid from Poly Scientific (Catalog #S2114) using a 1:10 dilution in DI water. Finally, the slides were rinsed again in distilled water, dehydrated in graded ethanol, cleared in xylene and mounted with coverslips using Cytoseal 60 media from Thermo-Scientific (Waltham, Mass., USA; Cat #8310). Images were taken using the AxioVision 4.9.1 software (Carl Zeiss Microscopy). For analysis of Sirius red staining and % collagen quantification, the contrast between the red and the green colors was enhanced using Adobe Photoshop. The color deconvolution plugin in the ImageJ software program was selected and the RGB color deconvolution option was used. The Red image includes all connective tissue from the Sirius Red stain. The Green image includes all muscle from the Fast Green counterstain. Only the Red image and the original image were used. A threshold was then applied to the images to obtain black and white images with areas positive for collagen in black and negative areas in white. Using the measure function, the area of collagen was calculated. The total tissue area was then determined by converting the originally image to '8-bit' and adjusting the threshold to 254, which will be one unit below completely saturating the image. The total tissue area was then measured as done previously and total area was recorded. The percentage of collagen was then calculated by dividing the area of collagen by the total tissue area. The mean percentage for each individual was then calculated.

Diaphragm Tetanic Contraction for Functional Assessment: Mice were euthanized and the diaphragm was dissected with rib attachments and central tendon intact, and placed in K-H buffer as previously described by Beastrom et al. (*Am. J. Pathol.* 179: 2464-74, 2011), Rafael-Forney et al. (*Circulation* 124: 582-8, 2011 and Moorwood et al. (*J. Visualized Experiments* 71:e50036, [year?]) A 2-4 mm wide section of diaphragm was isolated. Diaphragm strips were tied firmly with braided surgical silk (6/0; Surgical Specialties, Reading, Pa.) at the central tendon, and sutured through a portion of rib bone affixed to the distal end of the strip. Each muscle was transferred to a water bath filled with oxygenated K-H solution that was maintained at 37° C. The muscles were aligned horizontally and tied directly between a fixed pin and a dual-mode force transducer-servomotor (305C; Aurora Scientific, Aurora, Ontario, Canada). Two platinum plate electrodes were positioned in the organ bath so as to flank the length of the muscle.The muscle was stretched to optimal length for measurement of twitch contractions, and then allowed to rest for 10 minutes before initiation of the tetanic protocol. Once the muscle is stabilized, the muscle is set to an optimal length of 1 g and is subjected to a warm-up which consists of three 1 Hz twitches every 30 seconds followed by three 150 Hz twitches every minute. After a 3 min rest period, the diaphragm is stimulated at 20, 50, 80, 120, 150, 180 Hz, allowing a 2 min rest period between each stimulus, each with a duration of 250 ms to determine maximum tetanic force. Muscle length and weight was measured. The force was normalized for muscle weight and length.

Cardiac Magnetic Resonance Imaging: Cardiac function was analyzed using a 9.4T horizontal-bore magnetic resonance imaging (MRI) system and mouse volume coil (Bruker BioSpin, Billerica, Mass., USA). Mice were anaesthetized with 2.5% isofluorane mixed with carbogen (1 L/min) for 3 minutes prior to placement on the imaging bed. Upon placement of mice in imaging aparatus and initiation of imaging, isoflurane/carbogen mixture was dropped to 1.5% for the remainder of the study. EKG and respiration were monitored using an MRI-compatible system (Model 1025, Small Animal Instruments, Stonybrook, N.Y., USA). Gated cardiac short-axis FLASH cine T1-weighted images were acquired over the entire left ventricle (LV) of the mouse (TR=8 ms; TE=2.8 ms; □=18o; matrix=256×256; FOV=3.0×3.0 cm; slice thickness=1 mm, nslices=7, up to 20 frames per cardiac cycle). For image analysis, the end-diastolic and end-systolic timepoint of each short-axis image were identified and the endocardial and epicardial cardiac boundaries were manually traced. The papillary muscles were excluded from the endocardial boundary of the LV. From these measured areas, end-diastolic volume (EDV), end-systolic volume (ESV), stroke volume (SV), cardiac output (CO), ejection fraction (EF), and average LV mass were calculated.

Immunofluorescence: Cryostat sections (12 μm) from the tibialis anterior (TA), gastrocnemius (GAS), quadriceps (QUAD), psoas major (PSOAS), gluteal (GLUT), triceps (TRI), and diaphragm muscles along with the heart were subjected to immunofluorescence staining for the hSGCB transgene via our previously used protocol as described in Pozgai et al., Gene Therap. 23: 57-66, 2016. Sections were incubated with a mouse monoclonal human beta-sarcoglycan primary antibody (Leica Biosystems, New Castle, UK;

Cat. No. NCL-L-b-SARC) at a dilution of 1:100. Four random 20× images covering the four different quadrants of the muscle section were taken using a Zeiss AxioCam MRCS camera. Percentage of fibers positive for beta-sarcoglycan staining (>50% of muscle membrane staining) was determined for each image and averaged for each muscle.

Morphometric Analysis: Hematoxylin and eosin (H&E) staining was performed on 12 µm thick cryosections of muscle from 7 month old C57BL6 WT mice (n=5), sgcb$^{-/-}$ mice (n=5), and rAAV.MHCK7.hSGCB 6 month treated sgcb$^{-/-}$ mice (n=5) for analysis. The percentage of myofibers with central nuclei was determined in the TA, GAS, QUAD, PSOAS, GLUT, TRI, and diaphragm muscles. Additionally, muscle fiber diameters were measured in the GAS, PSOAS, and TRI muscles. Four random 20× images per muscle per animal were taken with a Zeiss AxioCam MRCS camera. Centrally nucleated fibers were quantified using the NIH ImageJ software and fiber diameters were measured using Zeiss Axiovision LE4 software.

X-Ray Images: Whole body x-rays were performed on anesthetized 7 month old C57BL6 WT mice (n=6), untreated sgcb$^{-/-}$ mice (n=6), and rAAV.MHCK7.hSGCB 6 month treated sgcb$^{-/-}$ mice (n=6) using the Faxitron MX-20 digital x-ray system at 26 kV for 3 secs (Faxitron X-Ray Corp, Lincolnshire, USA).

Laser Monitoring of Open Field Cage Activity: An open-field activity chamber was used to determine overall activity of experimental mice. Mice at 7 months old from the C57BL6 WT (n=6) and untreated sgcb$^{-/-}$ (n=6) control groups along with the rAAV.MHCK7.hSGCB 6 month treated sgcb$^{-/-}$ mice (n=6) were subjected to analysis following a previously described protocol (Kobayashi et al., Nature 456: 511-5, 2008, Beastrom et al., Am. J. Pahol. 179: 2464-74, 2011) with several modifications. All mice were tested at the same time of day in the early morning near then end of the night cycle when mice are most active. All mice were tested in an isolated room, under dim light and with the same handler each time. To reduce anxiety and keep behavioral variables at a minimum, which could potentially affect normal activity of the mice and consequently the results of the assay, the mice tested were not individually housed (Voikar et al., Genes Brain Behav. 4: 240-52, 2005). Mice were activity monitored using the Photobeam Activity System (San Diego Instruments, San Diego, Calif.). This system uses a grid of invisible infrared light beams that traverse the animal chamber front to back and left to right to monitor the position and movement of the mouse within an X-Y-Z plane. Activity was recorded for 1 hour cycles at 5-minute intervals. Mice were acclimatized to the activity test room for an initial 1 hour session several days prior to beginning data acquisition. Mice were tested in individual chambers in sets of 4. Testing equipment was cleaned between each use to reduce mouse reactionary behavioral variables that could alter our results. Data collected was converted to a Microsoft Excel worksheet and all calculations were done within the Excel program. Individual beam breaks for movement in the X and Y planes were added up for each mouse to represent total ambulation, and beam breaks in the Z plane were added up to obtain vertical activity within the 1 hour time interval.

Example 1 scAAVrh.74.tMCK.hSGCB Construction and Vector Potency

The transgene cassette containing a codon-optimized full-length human SCGB cDNA as shown in FIG. 1A was constructed. The cassette includes a consensus Kozak sequence (CCACC), an SV40 chimeric intron, a synthetic polyadenylation site, and the muscle-specific tMCK promoter (20) used to drive expression of the cassette. The cassette was packaged into a self-complementary (sc) AAVrh.74 vector that is 93% homologous to AAV8. AAVrh.74 has been shown in mice and non-human primates to be safe and effective, particularly in crossing the vascular barrier when delivered to muscle through the circulation.(17, 18, 21) Vector potency was established by intramuscular injection into the left TA muscle in the Sgcb-null mouse. Delivery of 3×10$^{10}$ vg transduced 70.5±2.5% of muscle fibers and 1×10$^{11}$ vg transduced 89.0±4.0% of muscle fibers, 3 weeks post gene transfer.

Example 2

Intramuscular Delivery of scAAVrh.74.tMCK.hSGCB

Figure 1B:
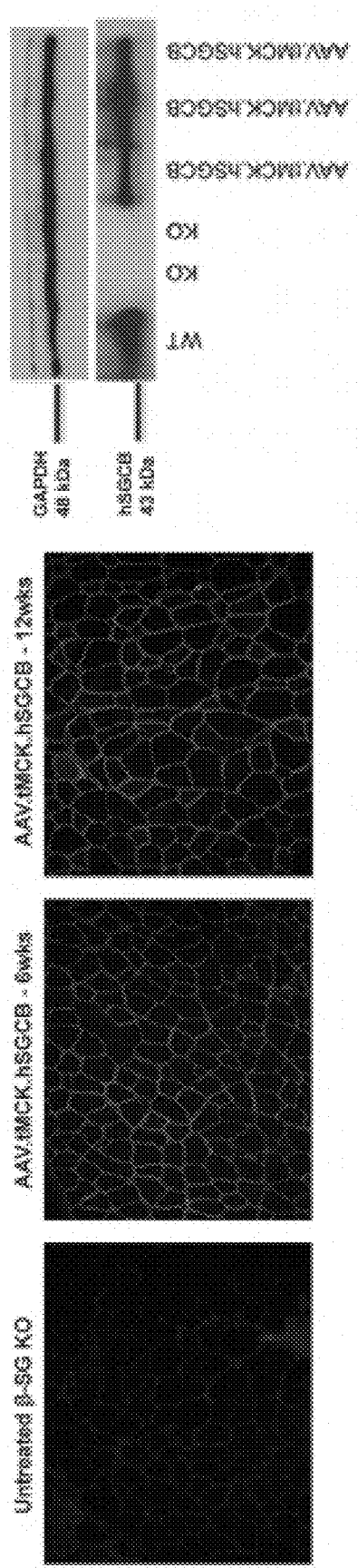
Figure 1C:
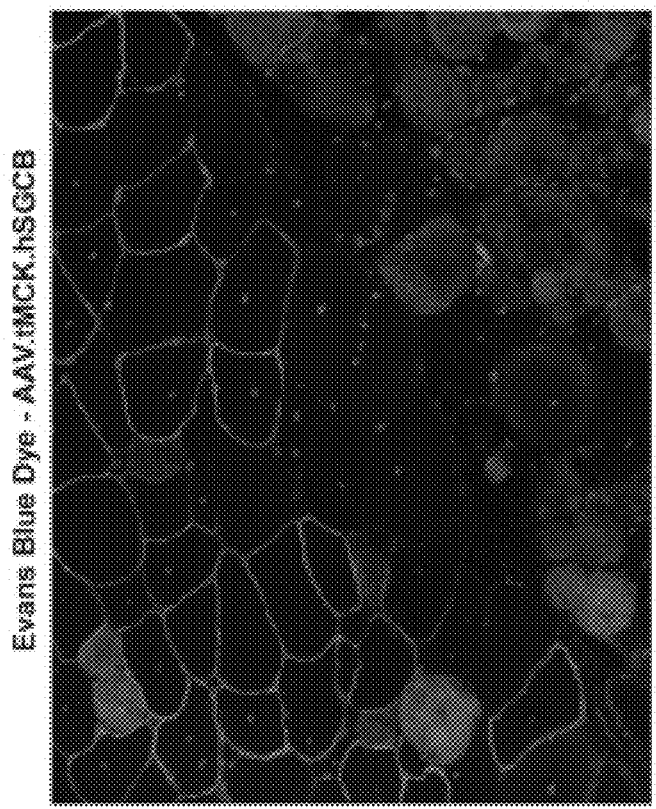
Figure 1D:
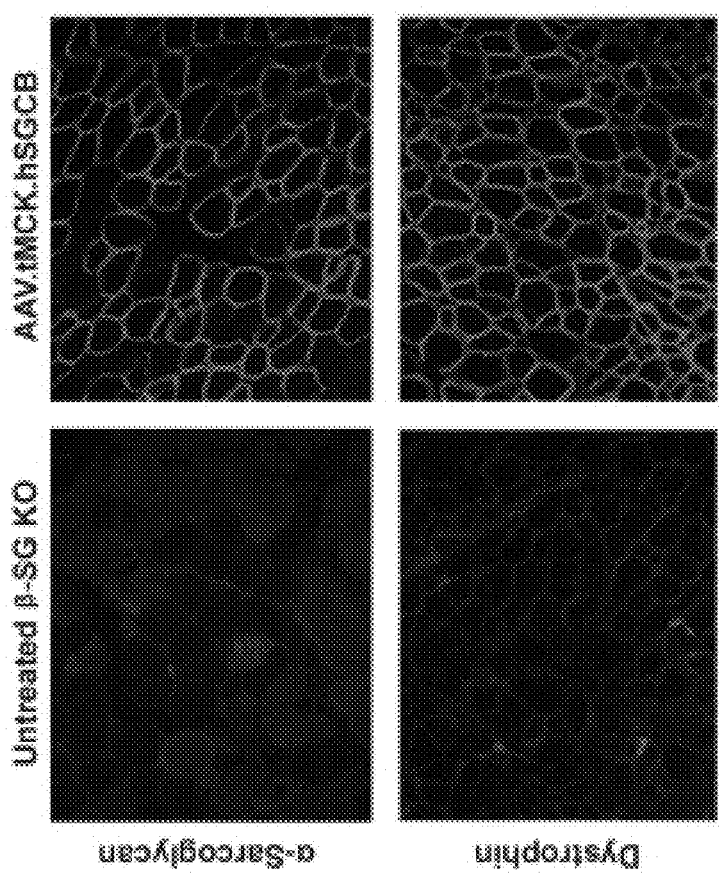
Figure 2C:
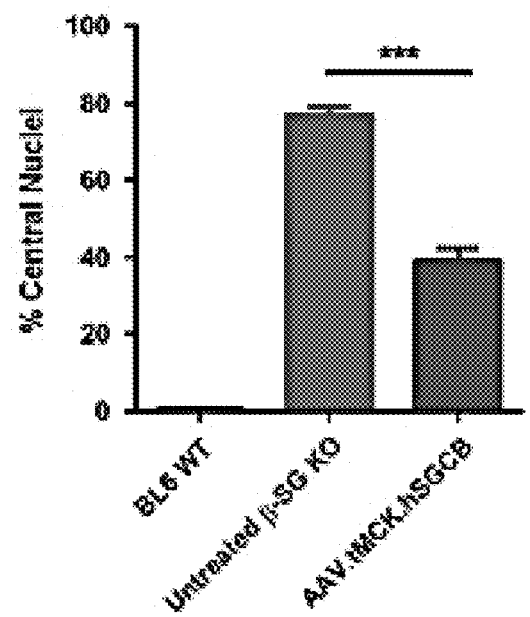
Figure 2D:
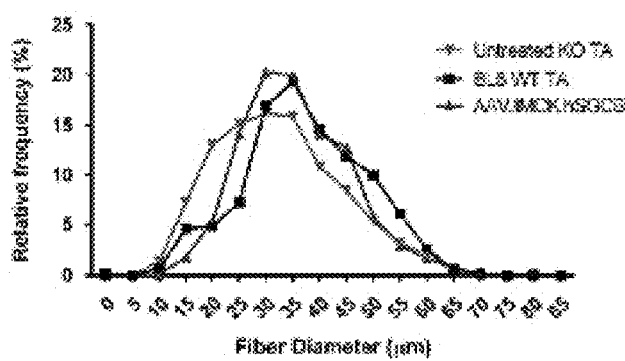

Following vector potency, studies were extended to analyze the efficacy of therapy 6 and 12 weeks post gene transfer. As a result of the high levels of expression following the short 3-week potency study, a dose of 3×10$^{10}$ vg total was selected for subsequent studies to use the lowest effective dose. Five-week-old sgcb$^{-/-}$ mice were treated with 3×10$^{10}$ vg of scAAVrh.74.tMCK.hSCGB intramuscularly to the left transverse abdominal (TA) and β-sarcoglycan expression was demonstrated using immunofluorescence in 88.4±4.2% of muscle fibers 6 weeks post injection (n=9), and in 76.5±5.8% of muscle fibers 12 weeks post injection (n=6), and expression was confirmed via western blotting (FIG. 1B). β-Sarcoglycan expression was accompanied by restoration of components of the dystrophin-associated protein complex (α-sarcoglycan and dystrophin) (FIG. 1C). Using Evans blue dye (EBD) as a marker for membrane permeability (22, 23) we found all fibers expressing exogenous β-sarcoglycan were protected from leakage and EBD inclusion (FIG. 1D). Muscle from sgcb$^{-/-}$ mice exhibit a severe muscular dystrophy with centrally nucleated fibers, frequent muscle fiber necrosis, fibrotic tissue and significant fiber size variability represented by both atrophic and hypertrophic fibers. (3, 4) As seen in FIG. 2A, hematoxylin & eosin staining shows an overall improvement in the dystrophic phenotype of diseased muscle including a reduction in central nuclei (sgcb$^{-/-}$ untreated—76.8±2.3% vs AAV.h-SCGB treated—38.86±3.5%; P<0.0001) (FIG. 2C). Normalization of fiber size distribution, with an increase in the average fiber diameter following treatment was also observed (sgcb$^{-/-}$ untreated—32.6±0.31 µm vs AAV.hSGCB treated—35.56±0.22 µm; P<0.0001) (FIG. 2D).

The histopathological hallmark of the scgb$^{-/-}$ mouse is fibrosis characterized by widespread replacement of muscle tissue primarily with collagens along with other extracellular matrix components such as fibronectin, elastin, laminin and decorin.(14) This replacement of muscle tissue by connective tissue challenges the potential value of gene replacement and may limit the degree of improvement. (24) To test this, mice treated for 12 weeks were assayed for reduction in fibrosis. The TA muscle was specifically assessed since its inherent degree of fibrosis was established in the KO model and because it represents a potential target following vascular ILP gene delivery. Picrosirius red staining for collagen, types I and III, of TA muscles showed a significant reduction (52.74%) in the amount of collagen present within scAAVrh.74.tMCK.hSGCB-treated muscle compared with untreated sgcb$^{-/-}$ mouse muscle (20.7±0.57% vs 43.8±2.3%, AAV.hSGCB treated vs sgcb$^{-/-}$ untreated, respectively; P<0.0001) (FIGS. 2b and e). Untreated sgcb$^{-/-}$ muscle from 5-week-old mice at the age of injection had 24.05±1.5% collagen deposition, indicating there was a slight (14.0%) reduction in the amount of collagen following the 12 weeks of treatment.

Example 3

Figure 3A:
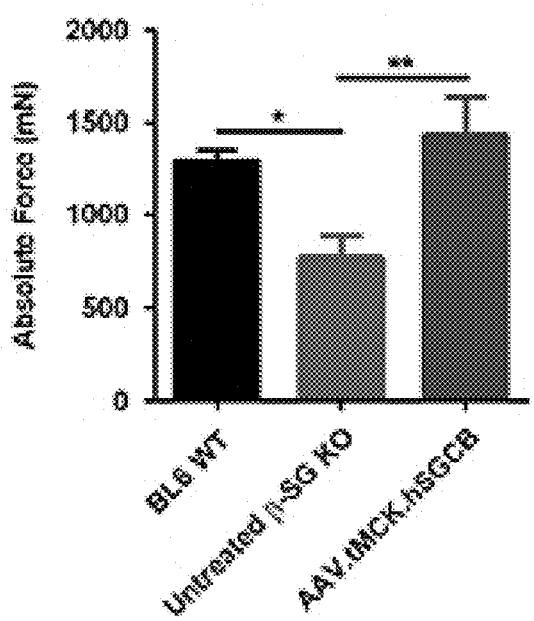
FIGS. 3A-3C shows that scAAVrh.74.hSGCB intramuscular delivery corrects tetanic force and resistance to contraction-induced injury. The TA muscle of sgcb$^{-/-}$ mice treated with 3×10$^{10}$ vg of scAAVrh.74.hSGCB via an IM injection was harvested 6 weeks post gene transfer, and subjected to a protocol to assess tetanic force and an eccentric contraction protocol to assess resistance to contraction-induced injury. (a) AAVrh.74.hSGCB-treated TA's demonstrated significant improvement in both absolute tetanic force (P<0.01, paired t-test) and (b) normalized specific force (P<0.05, paired t-test), which was not different from wild-type force (C57/BL6). (c) AAVrh.74.hSGCB treated TA's exhibited significant improvement in resistance to contraction-induced injury compared with untreated sgcb$^{-/-}$ controls (P<0.01, two-way ANOVA). Force retention following 10 contractions is shown. *P<0.05; **P<0.01.
Figure 3B:
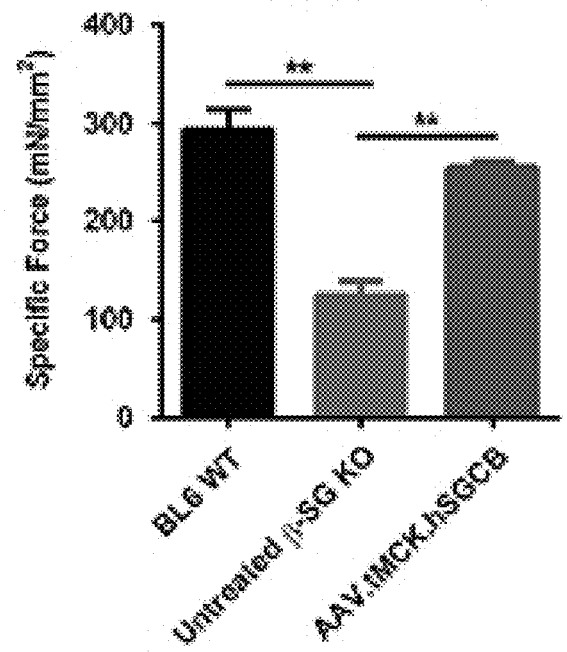
Figure 3C:
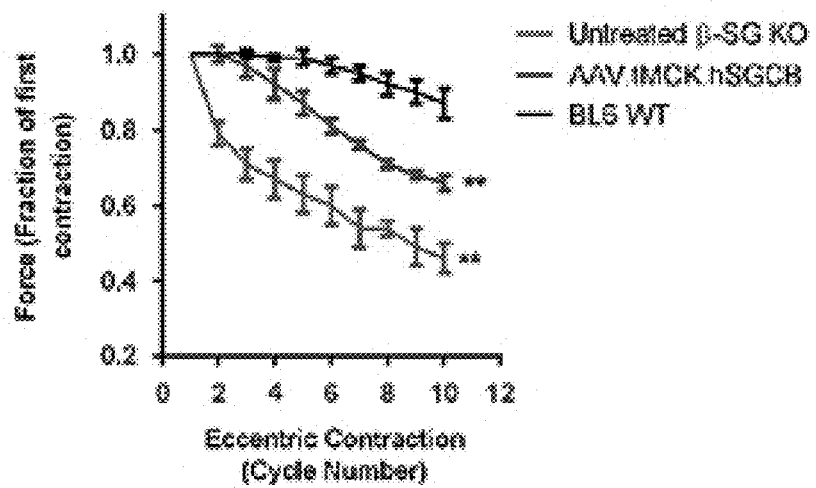

Functional Correction in Skeletal Muscle Following scAAVrh.74.tMCK.hSGCB Gene Transfer To determine whether hSGCB gene transfer can improve muscle function, we assessed the functional properties of the TA muscle from sgcb$^{-/-}$ mice treated with scAAVrh.74.tMCK.hSCGB. Following intramuscular delivery of 3×10$^{10}$ vg of scAAVrh.74.tMCK.hSCGB to the TA of 4-week-old sgcb$^{-/-}$ mice, 6 weeks post treatment the TA muscles were subjected to in situ force measurements (n=4). Treated muscles were compared with untreated contralateral muscles and those from C57BL/6 WT mice. scAAVrh.74.tMCK.hSCGB-treated muscle showed significant improvement in both absolute tetanic force and normalized specific force (FIGS. 3A and B). Treated muscles had an average absolute force of 1436.9±199.5 mN compared with 770.9±118.3 mN for untreated sgcb$^{-/-}$ controls (P<0.01). Similarly, treated TA muscles produced an average specific force of 254.01±6.9 mN/mm$^2$ and untreated muscles produced 124.2±13.9 mN/mm$^2$ of force (P<0.01). Finally, muscles treated with scAAVrh.74.tMCK.hSCGB showed greater resistance to contraction-induced injury compared with the untreated control muscles (FIG. 3C). Treated TA muscles lost 34.0±5.1% of force from that produced after the first contraction whereas untreated diseased muscle lost 54.1±3.8% (P<0.01) of force following the eccentric contraction protocol. These data show that hSGCB gene transfer does provide a functional benefit to diseased muscle deficient for β-sarcoglycan.

Example 4

Treatment of Aged Muscle with scAAVrh.74.tMCK.hSGCB

Studies of disease progression in this mouse model of LGMD2E have shown that although the most severe tissue remodeling in muscle occurs between 6 and 20 weeks, the histopathology of the muscle continues to worsen with age, resembling the disease progression in patients.(3, 4, 14) Consequently, to mimic a clinical setting where treatment would occur at an older age with more advanced muscle deterioration and endomysial fibrosis, we treated 6-month-old sgcb$^{-/-}$ mice (n=5) intramuscularly in the TA with 3×10$^{10}$ vg of scAAVrh.74.tMCK.hSCGB. Following 12 weeks of treatment, at 9 months of age, 80.1±4.8% of muscle fibers were transduced (FIG. 4A). Picrosirius red stain for collagen types I and III showed a 42.2% reduction in the amount of collagen present in treated mice compared with untreated sgcb$^{-/-}$ mouse muscle (AAV.hSGCB treated—20.0±0.80% vs sgcb$^{-/-}$ untreated—34.6±1.4%, P<0.0001) (FIGS. 4B and C). At the age of treatment, 6-month-old sgcb$^{-/-}$ mice have 30.8±2.0% collagen deposition (n=4, 4 male); thus, these results indicate that scAAVrh.74.tMCK.hSCGB treatment not only prevents, but also has the potential to reverse existing fibrosis.

Example 5

ILP of scAAVrh.74.tMCK.hSGCB in sgcb −/− Mice

Figure 5B:
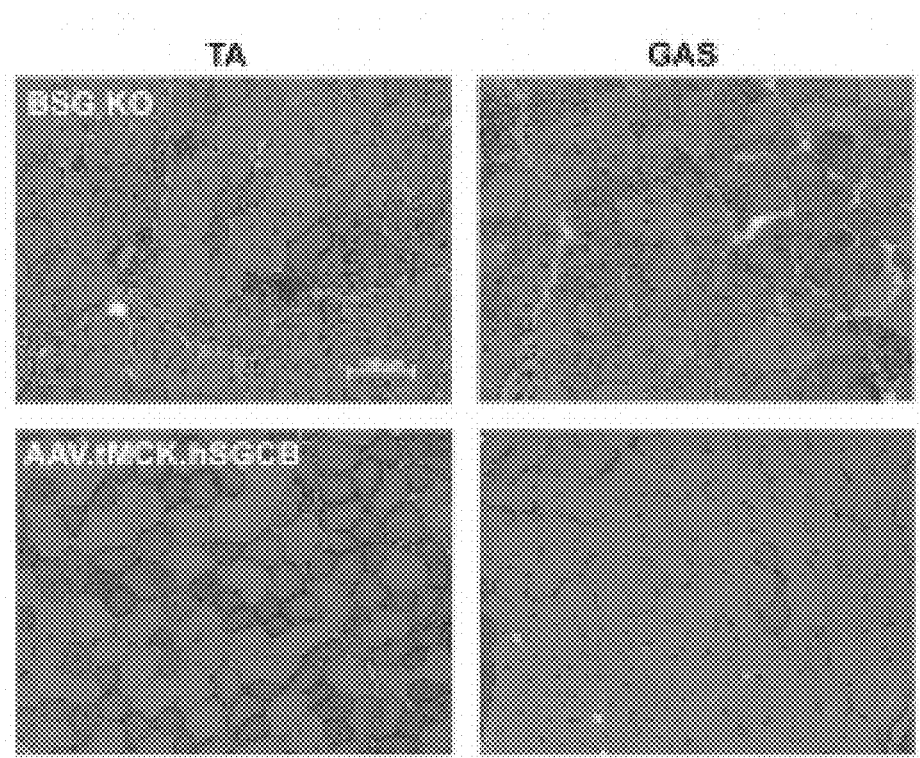
Figure 5C:
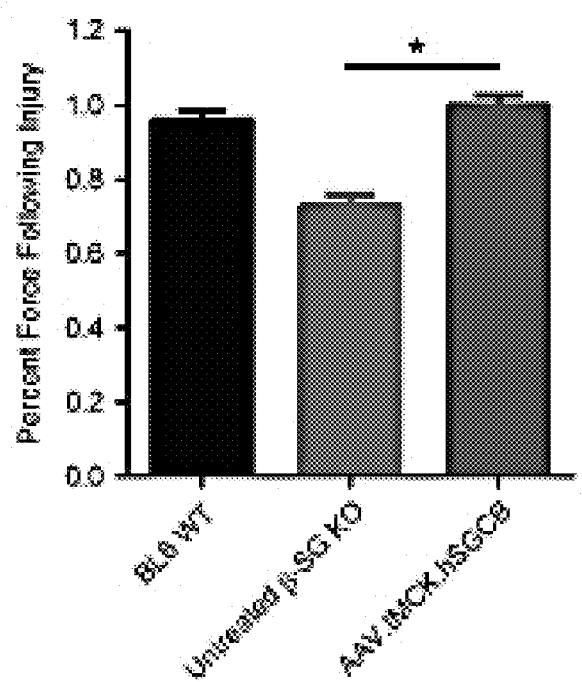

The ability to target multiple muscles in one limb allows for a more clinically relevant delivery method for translation to LGMD2E patients. Delivery of 5×10$^{11}$ vg of scAAVrh.74.tMCK.hSGCB by ILP in 4- to 6-week-old sgcb$^{-/-}$ mice (n=9, 7 male, 2 female) was analyzed 2 months post gene transfer. β-Sarcoglycan expression reached 91.8±4.7% of fibers in the gastrocnemius (GAS) muscle and 90.6±2.8% in TA (FIG. 5A). ILP delivery of scAAVrh.74.tMCK.hSGCB resulted in significant protection from eccentric contraction-induced injury (P<0.05), that was not different from WT, compared with untreated contralateral muscles (FIG. 5C). Vascular delivery also restored muscle histopathological parameters (FIG. 5B). Central nuclei were decreased in the TA (sgcb$^{-/-}$ untreated—76.9±2.8% vs AAV.hSGCB treated—23.2±5.7%, P<0.001) and GAS (sgcb$^{-/-}$ untreated—78.2±2.4% vs AAV.hSGCB treated—16.8±6.6%, P<0.001). Gene transfer also led to an increase in the average fiber size in the TA (sgcb$^{-/-}$ untreated—30.53±0.52 μm vs AAV.hSGCB treated—41.9±0.46 μm; P<0.0001) and GAS (sgcb$^{-/-}$ untreated—38.9±0.37 μm vs AAV.hSGCB treated—33.3±0.44 μm; P<0.0001), with normalization of fiber diameter distribution. a substantial decrease (~60%) in the number of CD3 cells, CD4 cells and macrophages (Table 1) was observed.

TABLE 1

Immune response in scAAVrh.74.tMCK.hSGCB ILP-treated mice

| Cell type | Treated Left TA cells/mm$^2$ | Untreated Right TA cell/mm$^2$ | Uninjected SGCB−/− TA cells/mm$^2$ |
|---|---|---|---|
| CD3 | 15.6 ± 3.2 | 37.85 ± 6.2 | 29.8 ± 1.7 |
| CD4 | 20.9 ± 4.7 | 58.1 ± 2.9 | 49.0 ± 0.8 |
| CD8 | 6.2 ± 1.8 | 12.7 ± 2.4 | 15.5 ± 5.8 |
| Macrophage | 28.2 ± 5.0 | 75.2 ± 5.6 | 100.2 ± 5.9 |

Abbreviations: ANOVA, analysis of variance; ILP, isolated-limp perfusion; SGCB, β-sarcoglycan; TA, tibialis anterior. Quantification of immune cells present in uninjected SGCB−/− mice, and scAAVrh.74.tMCK.hSGCB treated and untreated muscle. Data shown are following ILP delivery of virus and represent the mean number of cells/mm$^2$ ± s.e.m., n = 8 per group. A one-way ANOVA was used to compare values from the three different cohorts. Levels of immune cells were decreased with a statistically significant difference (P < 0.01) between the treated left TA and untreated right TA and/or the treated left TA and uninjected TA in all stains except for CD8.

Figure 6A:
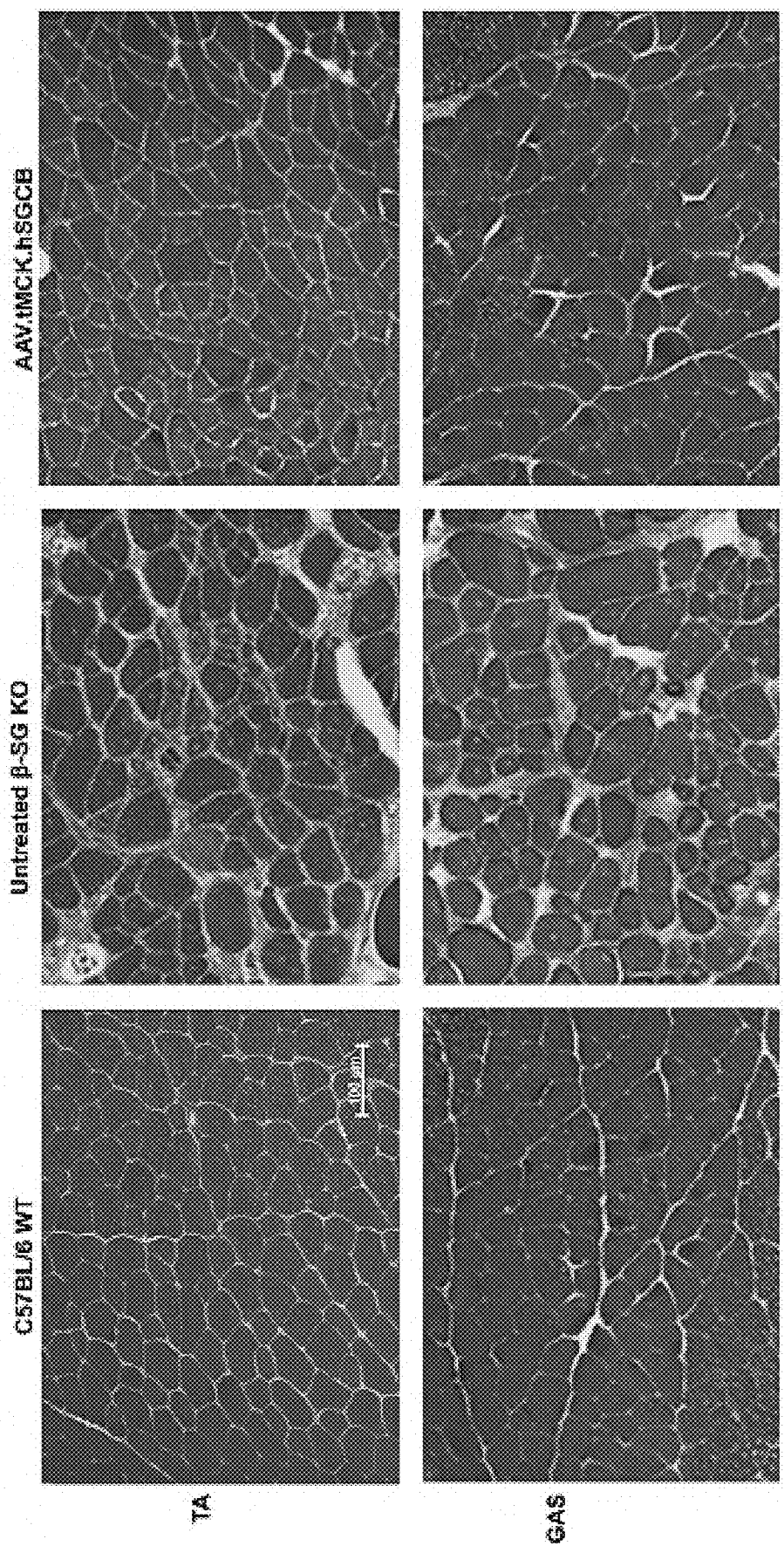
FIGS. 6A-6B show reduction of fibrosis in ILP-treated β-SG KO mice. (a) Picrosirius red staining shows reduced fibrosis in treated mice indicated by a decrease in collagen deposition compared with untreated sgcb$^{-/-}$ mice. (b) Quantification of collagen levels in the TA and GAS muscles from BL6 WT, untreated sgcb$^{-/-}$ mice, and treated mice confirm reduction in collagen levels in treated mice (P<0.001, one-way ANOVA). 100 μm scale bar shown for ×20 images. ***P<0.001.

Picrosirius red staining of TA and GAS muscles also showed a significant reduction in the amount of collagen compared with untreated sgcb$^{-/-}$ muscle following vascular delivery (FIG. 6a). Collagen levels in the TA were reduced to 21.6±1.3% in treated muscle compared with 40.2±1.5% in untreated sgcb$^{-/-}$ mice at the age of end point (P<0.0001). As indicated previously, sgcb$^{-/-}$ mice at the age of injection presented with 24.1±1.5% collagen in TA muscle, indicating again a slight reduction (10.0%) in collagen deposition following 8 weeks of treatment. Similarly, staining of the GAS muscle showed that treated mice had 22.9±0.99% collagen compared with 37.9±1.3% in untreated sgcb$^{-/-}$ mice at the end point (P<0.0001). Qualitative PCR was performed to detect collagen transcript levels in muscle, which correlate with the results of the Sirius red staining. Taken together, these data show that AAV-mediated delivery of human β-sarcoglycan reduces muscle fibrosis, improves muscle function and reverses dystrophic pathology of sgcb$^{-/-}$ diseased muscle.

Example 6

Safety and Biodistribution of rAAVrh.74.tMCK.hSGCB

Figure 7B:
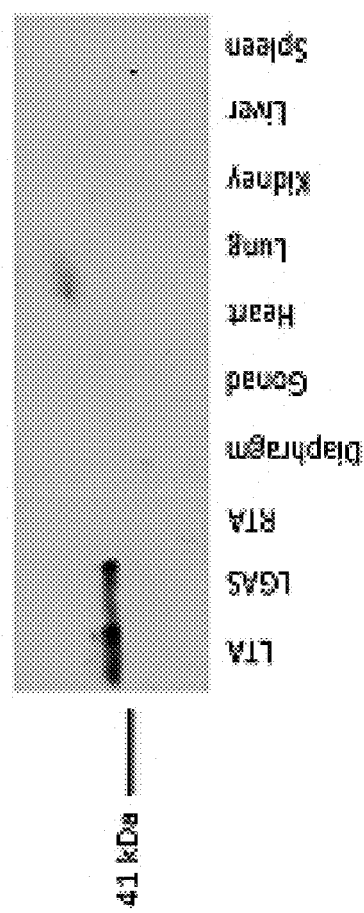
FIGS. 7A and 7B show vector biodistribution and protein expression. (a) Histogram of average distribution of vector in harvested tissues from ILP-treated mice given in copies of transcript per microgram of DNA added to qPCR. Left limb was treated. (b) No protein expression via western blot seen in off target organs.
Figure 7A:
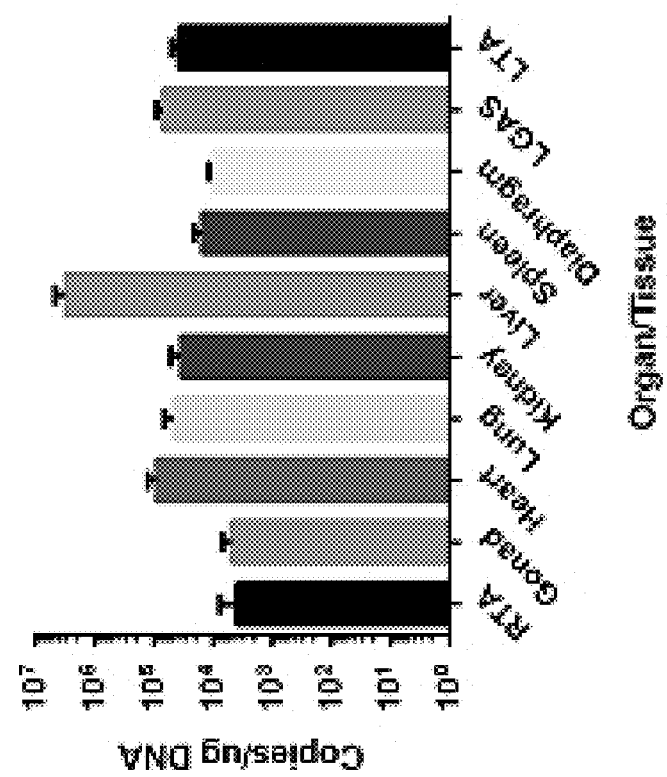

Initially, normal WT mice injected with $3 \times 10^{10}$ vg of scAAVrh.74.tMCK.hSGCB intramuscularly into the TA showed no signs of toxicity by H&E stain indicating no adverse effects due to the virus. Following the ILP vascular delivery of $5 \times 10^{11}$ vg total dose of scAAVrh.74.tMCK.hSGCB as described in the previous section, the safety was assessed in a small group of mice in this cohort (n=4). First, targeted muscles with significant gene expression were analyzed, as well as off target organs including heart, lung, liver, kidney, spleen, gonads and diaphragm histologically. Paraffin sections were formally reviewed by a veterinary pathologist and there was no evidence of toxicity in any organ noted (data not shown). Protein expression and vector biodistribution were also assessed in all of the above tissues and organs with western blotting and qPCR, respectively. Vector genome copies were detected in all organs tested; however, no protein expression was detected in any sample other than treated muscle (FIG. 7). Finally, an analysis of wet weights of treated and untreated muscle shows no significant difference or trend when comparing the average weights from either cohort (data not shown). These data provide evidence that the muscle-specific tMCK promoter restricted expression to skeletal muscle and the vector is non-toxic.

Example 7

Figure 8A:
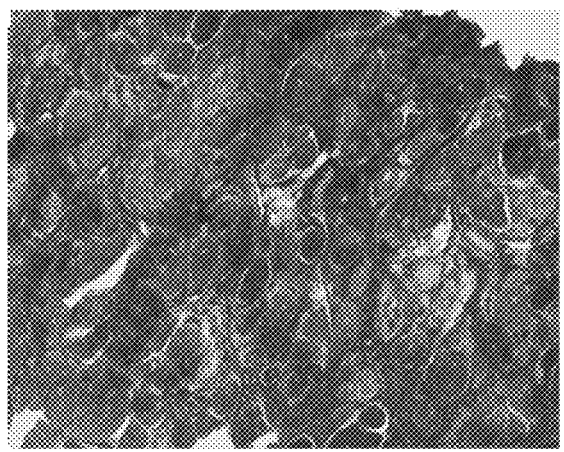
FIG. 8A-D provide histological and functional deficits in sgcb$^{-/-}$ mice at 7 months of age. Trichome staining in the diaphragm (A) and heart (C) of sgcb$^{-/-}$ mice shows extensive fibrosis (red). The force output from the diaphragm is significantly reduced in the diaphragm (B) and the cardiac ejection fraction is also reduced in sgcb$^{-/-}$ mice (D).
Figure 8B:
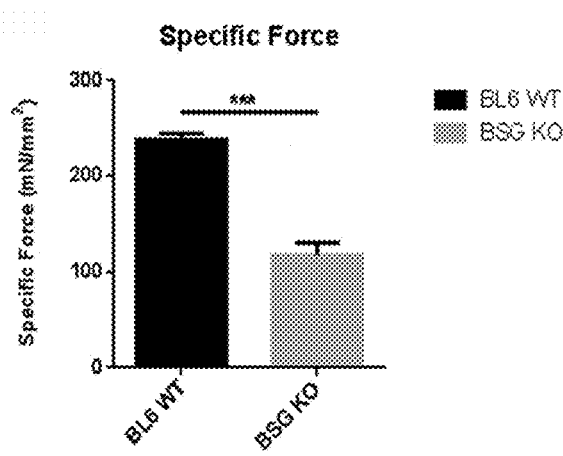
Figure 8C:
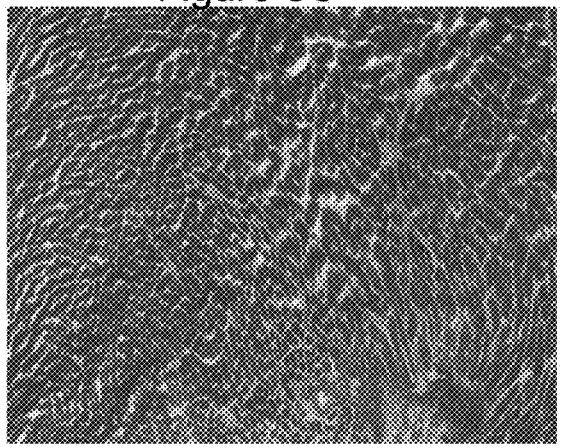
Figure 8D:
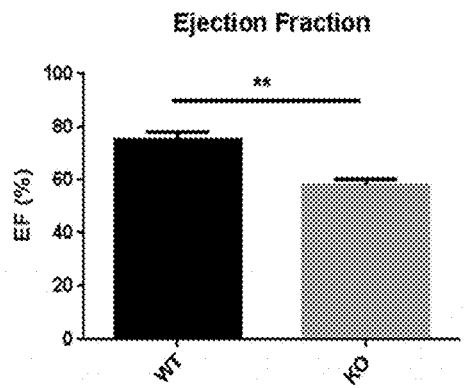

Histological and Functional Deficits in the Heart and Diaphragm of SGCB−/− Mice WT and 7 month old SGCB−/− mice (n=6 per strain) that were untreated were analyzed by cardiac MRI and diaphragm physiology to look for deficits. Following these analyses the animals were sacrificed and evaluated for histopathology (FIG. 8). Trichrome staining showed extensive fibrosis (red staining) in both the diaphragm (FIG. 8A) and heart (FIG. 8C). This was accompanied by functional deficits of specific force in the diaphragm (116.24 mN/mm² SGCB−/− vs. 236.67 mN/mm² WT, FIG. 8B) and significant deficit in ejection fraction measured by MRI (WT, 78% vs. SGCB−/− 65%, FIG. 8D).

Example 8 scAAVrh.74.MHCK7.hSGCB Construction and Vector Potency

Figure 9:
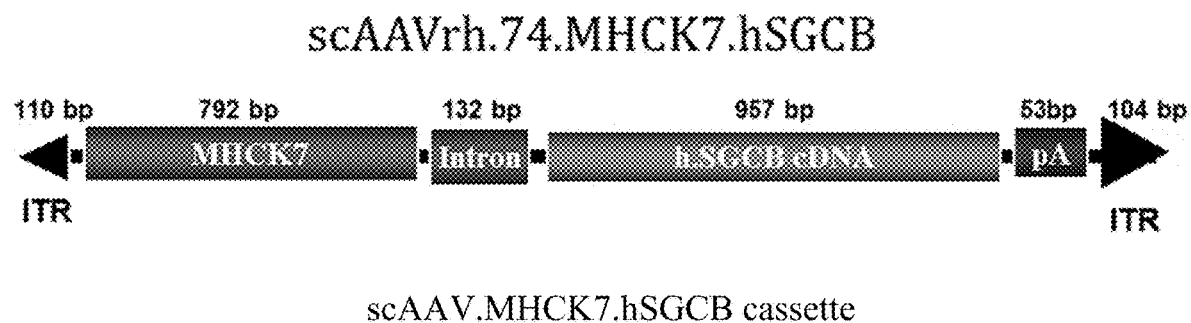
FIG. 9 provides a schematic of therapeutic β-sarcoglycan transgene cassette. Self-complementary AAV vector containing the codon-optimized human β-sarcoglycan gene (hSGCB). A muscle specific MHCK7 promoter drives expression. The cassette also contains a chimeric intron to augment processing and polyadenylation signal for stability.

The transgene cassette containing a codon-optimized full-length human SCGB cDNA as shown in FIG. 9A was constructed. The cassette includes a consensus Kozak sequence (CCACC), an SV40 chimeric intron, a synthetic polyadenylation site, and the muscle-specific MHCK7 used to drive expression of the cassette. This is an MCK based promoter which utilizes a 206-bp enhancer taken from ~1.2 kb 5' of the transcription start site within the endogenous muscle creatine kinase gene with a proximal promoter (enh358MCK, 584-bp)[3,12]. The cassette was packaged into a self-complementary (sc) AAVrh.74 vector that is 93% homologous to AAV8. AAVrh.74 has been shown in mice and non-human primates to be safe and effective, particularly in crossing the vascular barrier when delivered to muscle through the circulation.(17, 18, 21) Vector potency was established by intramuscular injection into the left TA muscle in the Sgcb-null mouse. Delivery of $3 \times 10^{10}$ vg transduced >90% of muscle fibers 4 weeks post gene transfer.

Example 9

Systemic Delivery of scAAV.MHCK7.hSGCB

Figure 10:
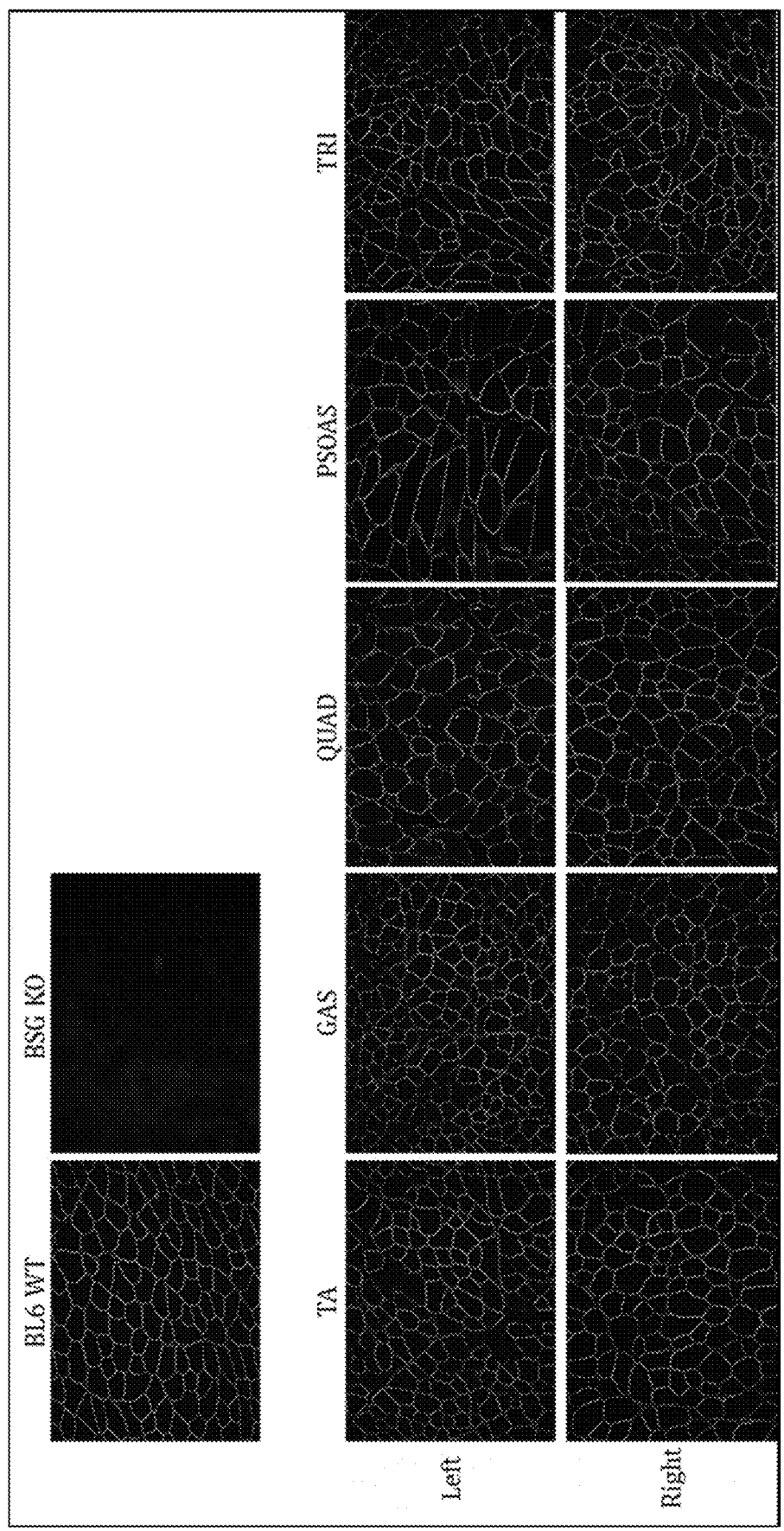
FIG. 10 provides immunofluorescence staining for β-sarcoglycan in various skeletal muscles demonstrates robust expression with rare negative fibers after 1, 4, or 6 months of treatment (1 month shown).

We delivered vector through a tail vein injection to 14 SGCB−/− mice at a dose of $1 \times 10^{12}$ vg total dose ($5 > 10^{13}$ vg/kg) to assess transgene expression and efficacy of our vector when delivered systemically at a long-term time point of 6 months. Mice were injected at 4 weeks of age and a full necropsy was performed at 6 months post-injection (1 mouse was taken down at 1 month and 2 mice were taken down at 4 months as intermediate assessments for expression). All skeletal muscles discussed above along with the diaphragm and heart were extracted for analysis. Organs were also removed for toxicology and biodistribution analysis. Immunofluorescence staining for human beta-sarcoglycan was used to determine hSGCB transgene expression in 5 limb muscles, both left and right, in additional to the diaphragm and heart of 6 of the KO mice given a systemic injection of hSGCB vector. These muscles included the TA, gastrocnemius (GAS), quadriceps (QUAD), gluteal (GLUT) (not shown), psoas major (PSOAS), and triceps (TRI) (FIG. 10). A qualitative analysis of heart tissue was also used to assess the relative level of transgene expression in cardiac muscle upon delivery.

Figure 11:
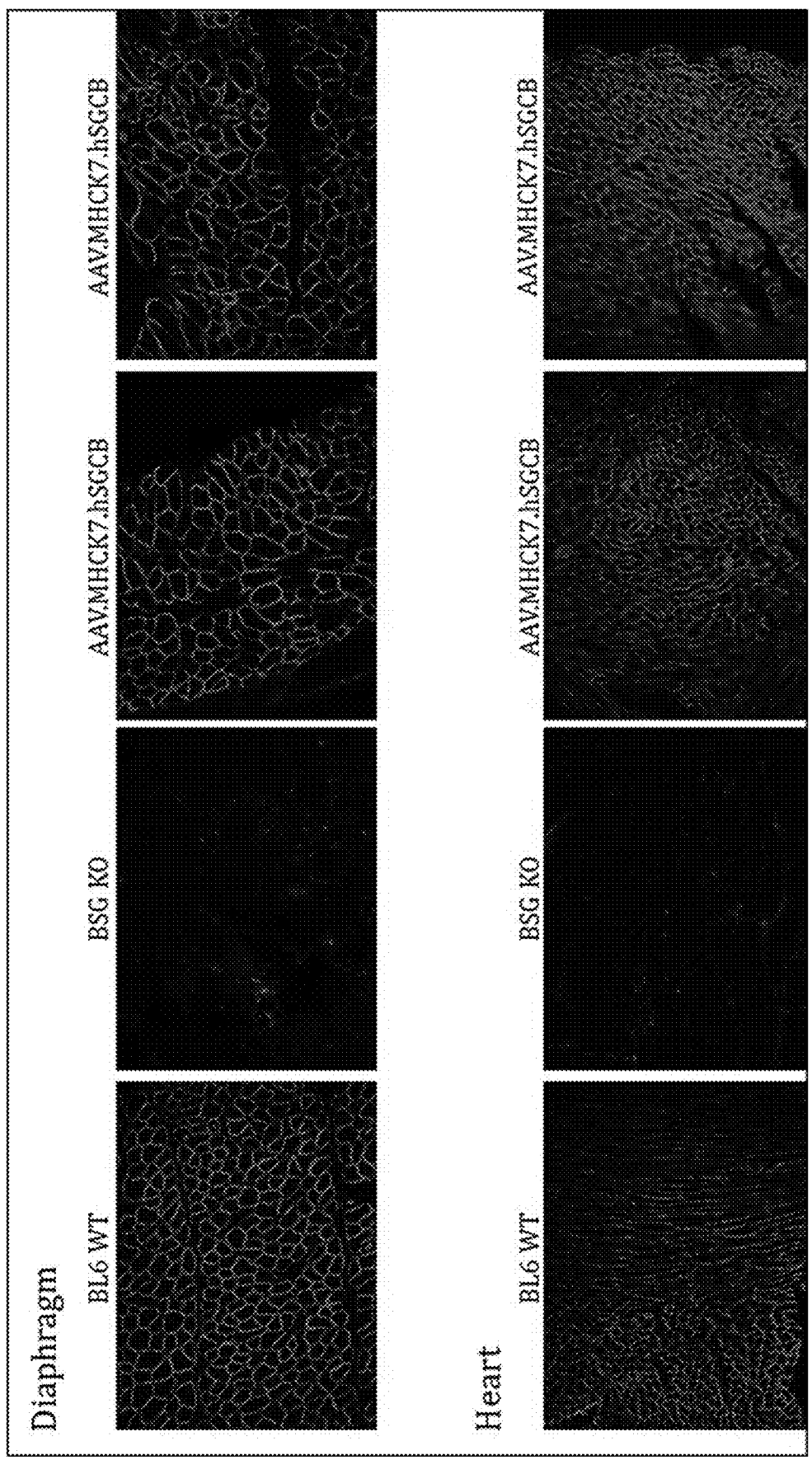
FIG. 11 provides immunofluorescence staining for β-sarcoglycan in diaphragm and heart demonstrates robust expression with rare negative fibers after 1, 4, or 6 months of treatment (1 month shown).

Four 20× images were taken of each muscle and the percent of hSGCB positive fibers was determined for each image resulting in the average percent transduction for each muscle from each mouse. The results shown in FIG. 10 and FIG. 11 demonstrate >98% transduction in all muscles analyzed including the diaphragm and heart. Mice deficient for β-sarcoglycan were completely absent of the protein when analyzed by immunofluorescence. The therapeutic dose of $1 \times 10^{12}$ vg total dose resulted in an average of 97.96±0.36% (±SEM) vector transduction across all skeletal muscles including the diaphragm, and approximately 95% or greater in cardiac muscle (data not shown).

Example 10

Long-Term Systemic Delivery of scAAVrh.74.MHCK7.hSGCB in SGCB−/− Mice

To build upon the results of the one-month potency assay described in Example 9, longer-term (6-month duration) systemic delivery of the β-sarcoglycan transgene cassette to sgcb−/− mice was investigated. Four-to-five week old sgcb−/− mice were treated with $1 \times 10^{12}$ vg total dose scAAVrh.74.MHCK7.hSGCB intravenously in the tail vein (n=5). Mice were necropsied 6 months post-injection and hSGCB transgene expression was demonstrated using immunofluorescence in six skeletal muscles, both left and right, in addition to the diaphragm and heart of all treated mice. Skeletal muscles analyzed included the TA, GAS, QUAD, gluteal (GLUT), PSOAS, and TRI. Average hSGCB expression resulting from systemic delivery in treated mice was 98.13±0.31% (±SEM) across all skeletal muscles including the diaphragm, with expression in the heart exceeding >95%. Representative images are shown in FIG. 12b. The expression levels in each individual muscle type averaged from all treated mice are shown in Table 2. Western blotting in FIG. 12c confirms transgene expression in all muscles. The expression values in Table 2 are presented for various muscles as the average of left and right muscles from systemically injected mice (n=5). Values indicated as AVG ±SEM. In addition, quantification of hSGCB transgene expression in hearts from treated mice via western blotting and densitometry indicate overexpression of hSGCB up to 72.0% above BL6 WT levels of expression (FIG. 12d), correlating to the high levels quantified in skeletal muscle.

TABLE 2

β-sarcoglycan Immunofluorescence Expression

| Muscle | Delivery Route | Dose (vg Total Dose) | Endpoint (Months) | % Fibers Expressing SGCB |
|---|---|---|---|---|
| TA | IV | 1e12 | 6 | 98.88 ± 0.55 |
| GAS | IV | 1e12 | 6 | 98.24 ± 0.82 |
| QD | IV | 1e12 | 6 | 99.32 ± 0.19 |
| GLUT | IV | 1e12 | 6 | 97.50 ± 0.39 |
| PSOAS | IV | 1e12 | 6 | 98.75 ± 0.23 |
| TRI | IV | 1e12 | 6 | 97.21 ± 1.35 |
| Diaphragm | IV | 1e12 | 6 | 97.00 ± 1.26 |
| Heart | IV | 1e12 | 6 | ≥95% |

Figure 13A:
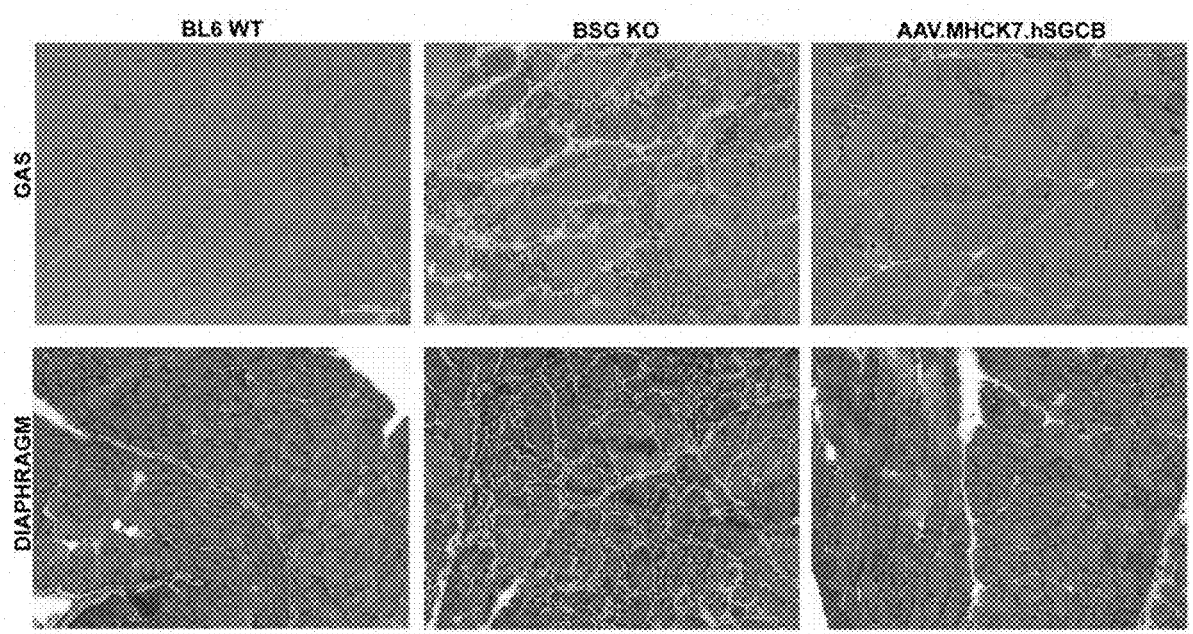
FIG. 13A-D depicts the effect of systemic treatment with scAAVrh74.MHCK7.hSGCB on muscle pathology. (a) H&E stain of diaphragm and QUAD muscle from C57BL/6 WT, sgcb$^{-/-}$, and scAAVrh.74.MHCK7.hSGCB treated mice showing normalized histopathology. (b) Quantification of reduction in centrally nucleated fibers in sgcb$^{-/-}$ treated muscle compared to untreated sgcb$^{-/-}$ muscle (TA, GAS, GLUT, diaphragm, p<0.0001) (QUAD, PSOAS, TRI, p<0.05). (c) Normalization of fiber distribution in GAS, PSOAS, and TRI, and (d) increase in average fiber size in treated muscles compared to untreated sgcb$^{-/-}$ muscles (p<0.001) (ONE-WAY ANOVA) (n=5 per group).
Figure 13B:
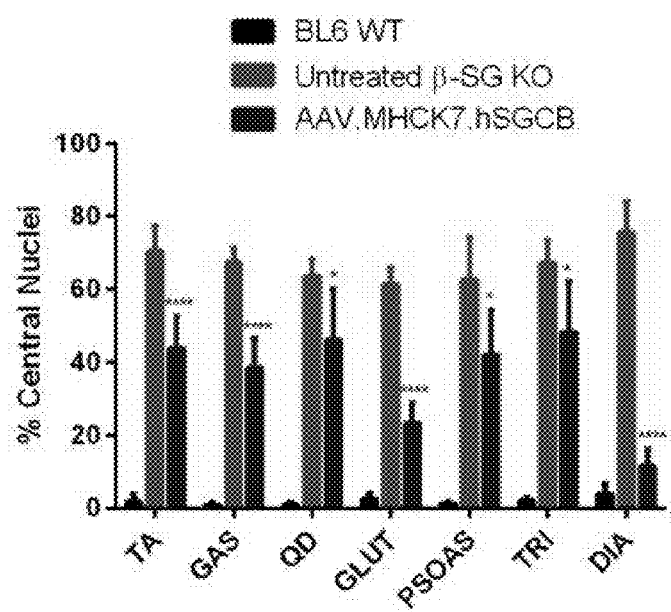
Figure 13C:
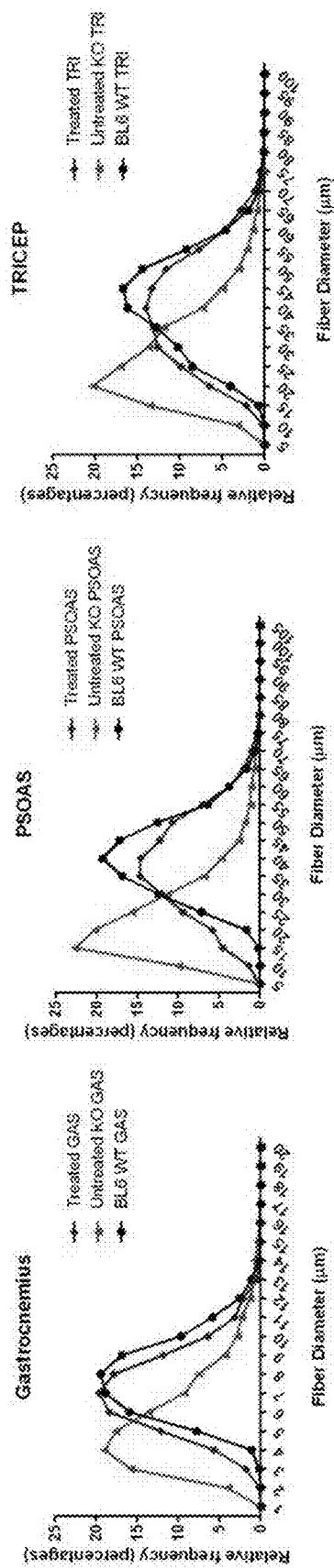
Figure 13D:
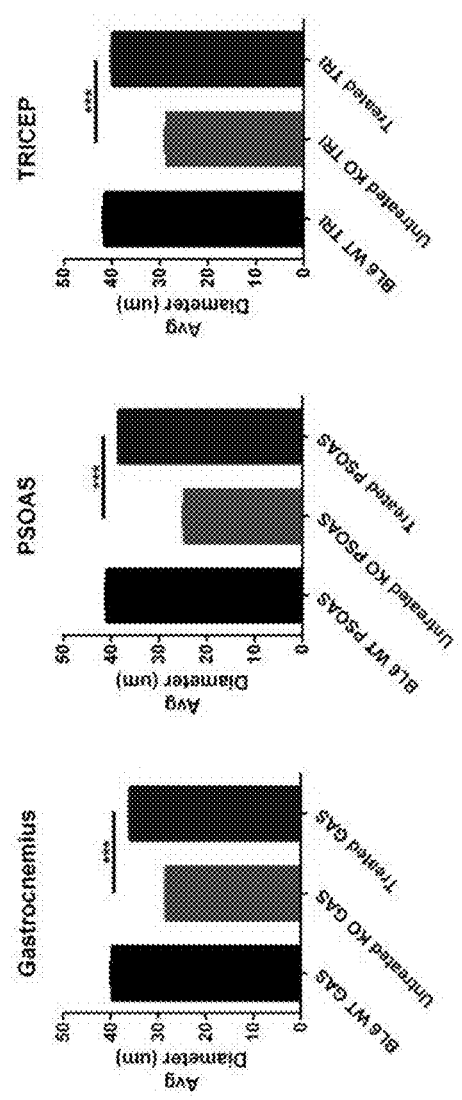

An important characteristic of sgcb$^{-/-}$ muscle described in previous reports (Araishi et al, Hum. Mol. Genet 8: 1589-98, 1999, Durbeej et al., Mol. Cell. 5:141-51, 2000) and illustrated by the hematoxylin & eosin staining of the GAS and diaphragm in FIG. 13a is severe dystrophic pathology including central nucleation, necrosis, inflammatory infiltration, and fibrosis. Gene transfer significantly improved this pathology, alleviating many of these dystrophic features (FIG. 13a). Quantification of histological parameters showed a significant reduction in central nucleation in the various skeletal muscles analyzed as a result of gene transfer (FIG. 13b). With the expected low levels of central nucleation in BL6 WT mice across all muscles averaging 1.89±0.39%, as note here, taking into account all muscles analyzed, an average of 66.85±1.86% central nuclei in untreated sgcb$^{-/-}$ mice compared to 36.30±5.16% in AAV.MHCK7.hSGCB treated sgcb$^{-/-}$ muscle ($p<0.0001$) Table 3 below provides central nuclei counts and fiber diameters given for various muscles as the average (±SEM) of left and right muscles from BL6 WT, sgcb$^{-/-}$, and systemically injected mice (n=5 per group). Of note, the most significant wave of degeneration/regeneration occurs at 3 weeks in sgcb$^{-/-}$ muscle indicated by centrally placed nuclei. Animals were treated following this insult and therefore a complete reversal of centralized nuclei was not anticipated. A more in depth analysis of muscle histopathology revealed a normalization of fiber size distribution accompanied by an increase in average fiber diameter in diseased mice treated with vector compared with untreated sgcb$^{-/-}$ mice in all three muscles examined (GAS: sgcb$^{-/-}$ untreated ~28.37±0.23 µm vs. AAV.hSGCB treated ~36.04±0.17 µm; $p<0.0001$) (PSOAS: sgcb-/- untreated—24.75±0.23 µm vs. AAV.hSGCB treated—38.43±0.28 µm; $p<0.0001$) (TRI: sgcb$^{-/-}$ untreated—28±0.31 µm vs. AAV.hSGCB treated—35.56±0.22 µm; $p<0.0001$) (FIGS. 13c, 13d, Table 3).

TABLE 3

Analysis of Percent Central Nucleation

| Animal Group | Dose (vg Total Dose) | Muscle | % Central Nuclei (Avg ± SEM) | Combined Avg % CN (±SEM) | Fiber Diameter µm (Avg ± SEM) |
|---|---|---|---|---|---|
| C57BL6 WT | N/A | TA | 1.78 ± 0.86 | 1.89 ± 0.39 | N/A |
|  |  | GAS | 0.83 ± 0.41 |  | 39.69 ± 0.18 |
|  |  | QD | 0.98 ± 0.31 |  | N/A |
|  |  | GLUT | 2.50 ± 0.68 |  | N/A |
|  |  | PSOAS | 1.26 ± 0.28 |  | 40.96 ± 0.22 |
|  |  | TRI | 2.13 ± 0.36 |  | 41.53 ± 0.24 |
|  |  | DIA | 3.75 ± 1.30 |  | N/A |
| Sgcb$^{-/-}$ | N/A | TA | 70.45 ± 3.04 | 66.85 ± 1.86 | N/A |
|  |  | GAS | 67.26 ± 1.81 |  | 28.37 ± 0.23 |
|  |  | QD | 63.57 ± 2.09 |  | N/A |
|  |  | GLUT | 61.34 ± 2.05 |  | N/A |
|  |  | PSOAS | 62.73 ± 5.20 |  | 24.75 ± 0.22 |
|  |  | TRI | 67.11 ± 2.83 |  | 28.74 ± 0.22 |
|  |  | DIA | 75.47 ± 3.79 |  | N/A |
| AAV.MHCK7.hSGCB Treated | 1.00E+12 | TA | 43.85 ± 3.89 | 36.30 ± 5.16 | N/A |
|  |  | GAS | 38.71 ± 3.50 |  | 36.04 ± 0.18 |
|  |  | QD | 46.10 ± 6.26 |  | N/A |
|  |  | GLUT | 42.11 ± 5.48 |  | N/A |
|  |  | PSOAS | 21.00 ± 4.69 |  | 38.43 ± 0.28 |
|  |  | TRI | 48.39 ± 6.20 |  | 39.92 ± 0.27 |
|  |  | DIA | 11.59 ± 2.08 |  | N/A |

Figure 14A:
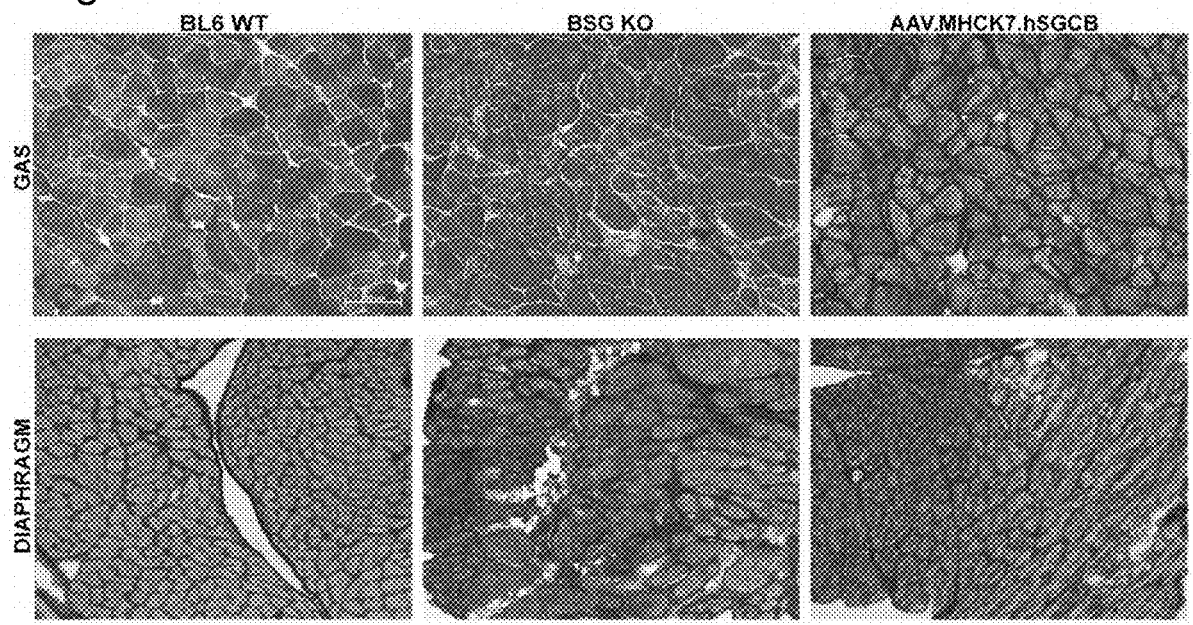
FIGS. 14A and 14B depict reduced collagen deposition in intravenous treated β-SG KO mice. (a) Picrosirius red staining showed reduced fibrosis in treated mice indicated by a decrease in collagen deposition compared to untreated sgcb$^{-/-}$ mice in diaphragm and GAS. (b) Quantification of collagen levels in the diaphragm and GAS muscles from C57BL/6 WT mice (n=4), untreated sgcb$^{-/-}$ mice (n=4), and treated sgcb$^{-/-}$ mice (n=5) confirm reduction in collagen levels in both treated muscles (p<0.0001, ONE-WAY ANOVA). 100 μm scale bar shown for 20× images.
Figure 14B:
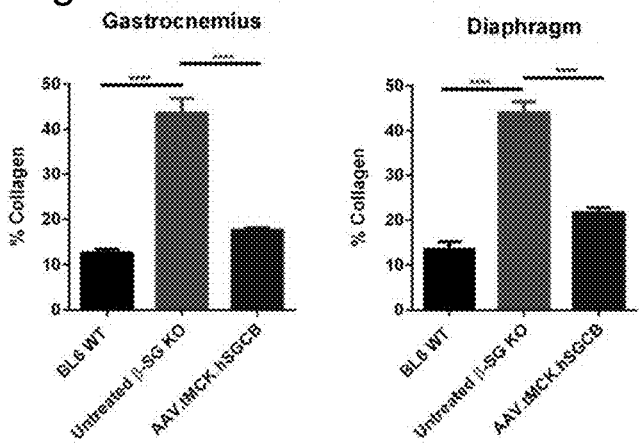

Due to the significant role fibrosis plays in the pathogenesis of LGMD2E and effectiveness of therapies, it was critical to demonstrate the same efficacy in reducing fibrosis. That was saw with localized β-sarcoglycan gene transfer. now following systemic delivery of scAAVrh.74.MHCK7.hSGCB. Using the Picrosirius red stain for collagen types I and III, we analyzed the levels of collagen in the gastrocnemius and diaphragm muscles was analyzed in 7 month old BL6 WT mice (n=4), untreated sgcb$^{-/-}$ mice (n=4), and treated sgcb$^{-/-}$ mice (n=5) 6 months post-injection. Treated muscles displayed significantly less collagen deposition compared to untreated sgcb$^{-/-}$ muscles (FIG. 14a). Vector transduced GAS muscle contained 17.55±0.59% collagen compared to 43.55±3.33% collagen in untreated sgcb-/- GAS muscles (p<0.0001). Furthermore, treated diaphragm muscle exhibited 21.67±1.09% collagen compared to 44.05±2.39% in untreated sgcb-/- muscle (p<0.0001) (FIG. 14b) demonstrating the ability of hSGCB gene transfer to mitigate the fibrotic component of the LGMD2E phenotype.

Example 11

Restoration of Diaphragm Function Following Systemic Delivery

Figure 15:
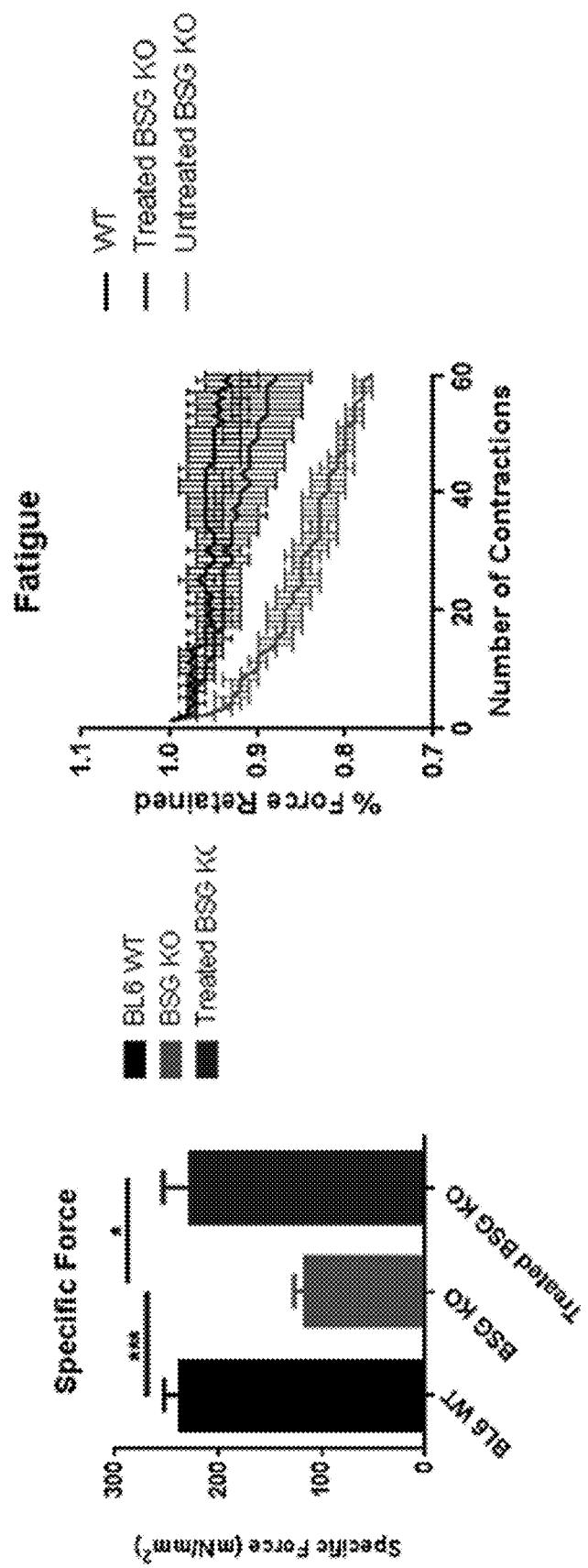
FIG. 15 demonstrates delivery of scAAVrh.74.MHCK7.hSGCB via the tail vein of sgcb$^{-/-}$ mice completely restores force in the diaphragm following 6 months of treatment (IV administration (1e12 vg)). Diaphragm muscle strips were harvested from treated and control sgcb$^{-/-}$ mice and WT mice and subjected to force measurements, treatment restored force to WT levels.

To determine whether hSGCB gene transfer can improve muscle function, we assessed the functional properties of the diaphragm muscle from SGCB$^{-/-}$ mice treated with scAAVrh.74.MHCK7.hSCGB (see Griffin et al. for methods). A functional deficit in diaphragms of SGCB-/- mice was first established. KO diaphragms demonstrated a 50.9% reduced specific force output (116.24 mN/mm$^2$) compared to BL6 WT mice (116.24 mN/mm$^2$ vs. 236.67 mN/mm$^2$) and greater loss of force following a rigorous fatigue protocol (23% loss in SGCB$^{-/-}$; 7% loss in BL6 WT). Tail vein delivery of scAAVrh.74.MHCK7.hSGCB resulting in nearly 100% hSGCB expression in the diaphragm lead to restoration of diaphragm function with specific force output improved to 226.07 mN/mm$^2$ and a greater resistance to fatigue with only a 12% loss of force (n=5) (FIG. 15).

Example 12

Delivery of scAAVrh.74.CMV.miR29C Reduces Fibrosis in SGCB-/- Mice

Figure 2E:
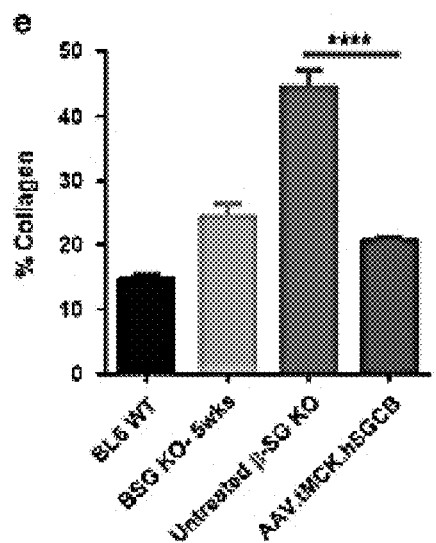
Figure 6B:
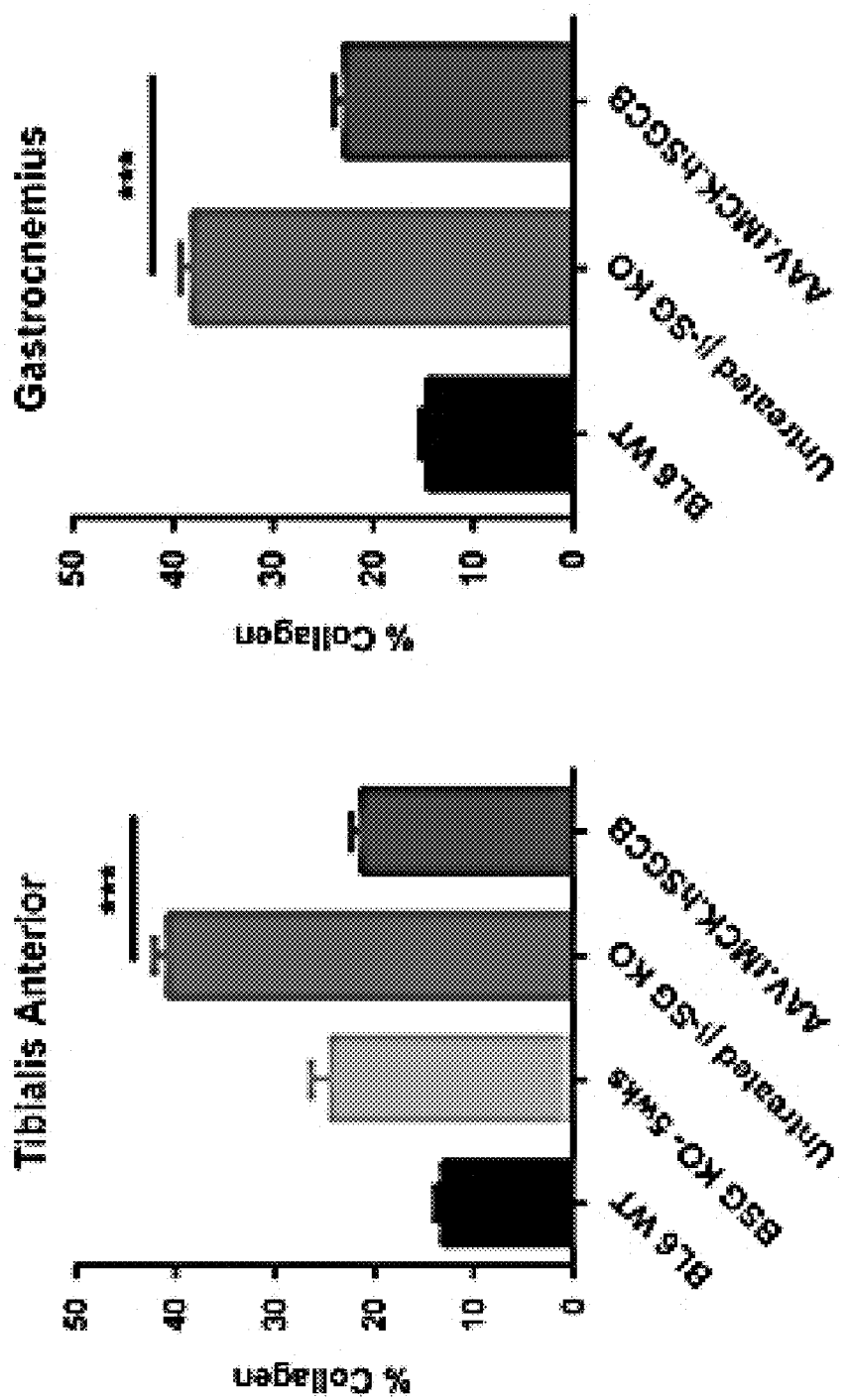
Figure 17:
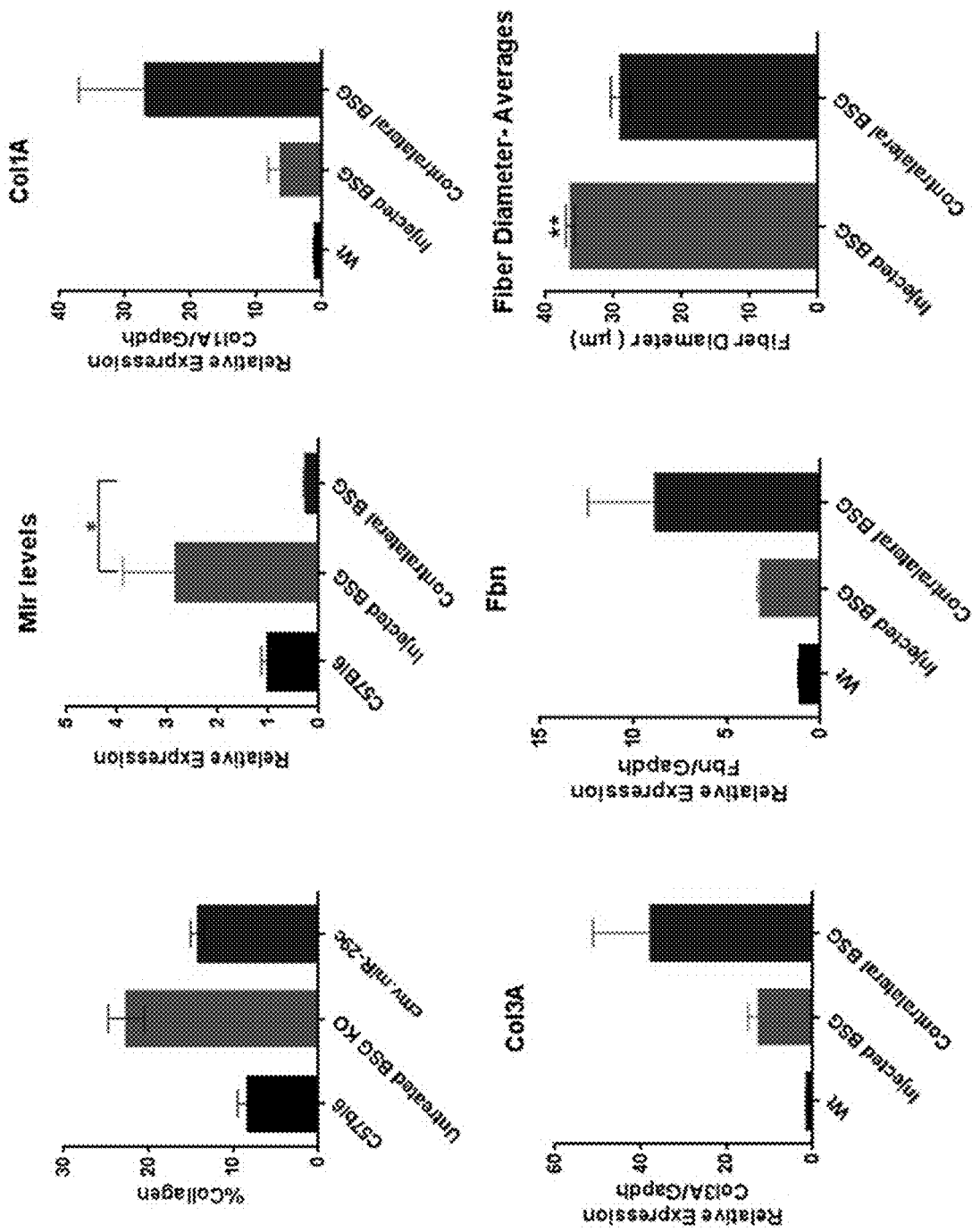
FIG. 17 demonstrates that following 3 months of treatment with AAVrh.74.CMV.miR29C, TA muscles were harvested from treated and control sgcb$^{-/-}$ mice and WT mice and analyzed for fibrosis (collagen levels) (n=5 per group). Using sirius red staining and quantification, collagen levels were reduced following treatment (see FIG. 18). Results indicated that transcript levels of Col1A, Col3A, and Fbn were normalized and muscle fiber size was increased.

The extensive fibrosis we identified in both skeletal muscle (FIGS. 2, 4, and 6) as well as the heart and diaphragm (FIG. 8) demonstrated a need to treat collagen deposition (fibrosis) in LGMD2E. We previously found that miR-29c was most severely reduced (of miR-29a, b, c) in Duchenne muscular dystrophy. He hypothesized that miR-29c would also be reduced in Beta-sarcoglycan deficient mice (a mouse model for LGMD2E). We proved this to be true (FIG. 15). MiR-29c levels were decreased, fibrosis (collagen) levels were increased, and three components of fibrosis (Co1A, Col3A, and Fbn) were increased at the RNA level. To test whether we could prevent fibrosis with miR-29c, The gene therapy vector scrAAVrh.74.CMV.miR29c (3 ×1011 vgs) was injected into the tibialis anterior muscle of 4 week old sgcb$^{-/-}$ mice (n=5). The scrAAVrh.74.CMV.miR29c is shown in FIG. 16 and described in U.S. Provisional Application No. 62/323,163, the disclosure of which is incorporated herein by reference in its entirety. Following 2 months of treatment with AAVrh.74.CMV.miR29C, TA muscles were harvested from treated and control SGCB/sgcb$^{-/-}$ mice and WT mice and analyzed for fibrosis (collagen levels) (n=5 per group). Using sirius red staining and quantification, collagen levels were reduced following treatment (see FIG. 17). Transcript levels of Col1A, Col3A, and Fbn were normalized and muscle fiber size was increased. Representative images of scanned full sections of untreated and AAVrh.74.CMV.miR29C treated tibialis anterior muscles stained with Sirius Red which stains for collagen 1 and 3 are shown in FIG. 18. This demonstrates proof of principle that scAAVrh.74.CMV.miR29C reduces fibrosis in sgcb$^{-/-}$ mice and could be used in combination with gene replacement with scAAVrh.74.tMCK.hSGCB or scAAVrh.74.MHCK7.hSGCB.

Example 13

Figure 19A:
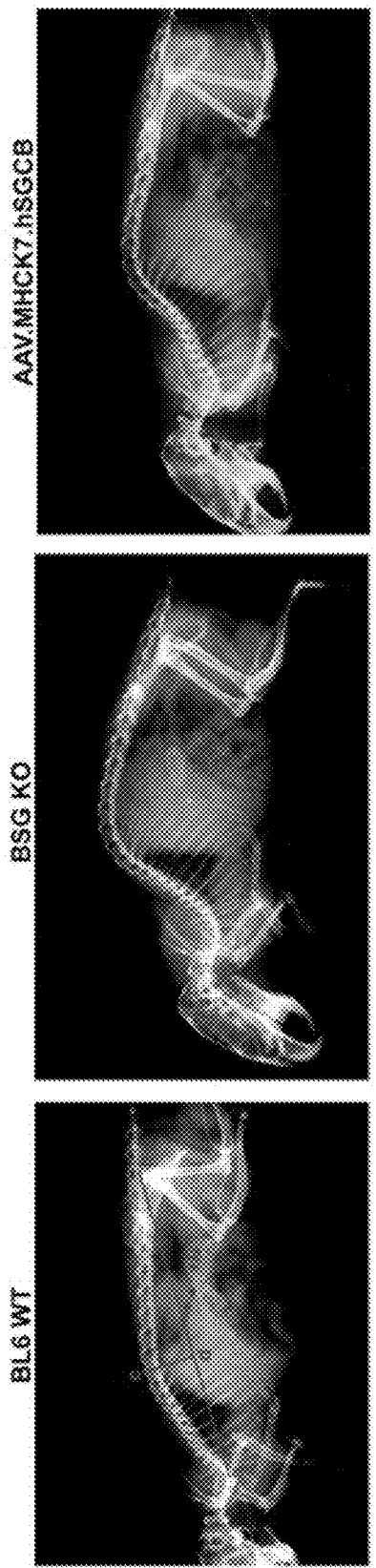
FIGS. 19A and 19B demonstrate correction of kyphoscoliosis in thoracic spine. (a) Kyphoscoliosis in sgcb$^{-/-}$ mice as evidenced by X-ray radiography. (b) The Kyphotic Index (KI) score of sgcb$^{-/-}$ mice (3.69) is low compared to C57BL/6 WT (6.01) (p<0.01), but increases upon treatment with scAAVrh.74.MHCK7.hSGCB (5.39) (p<0.05 compared to sgcb$^{-/-}$) (ONE-WAY ANOVA) (n=6 per group).
Figure 19B:
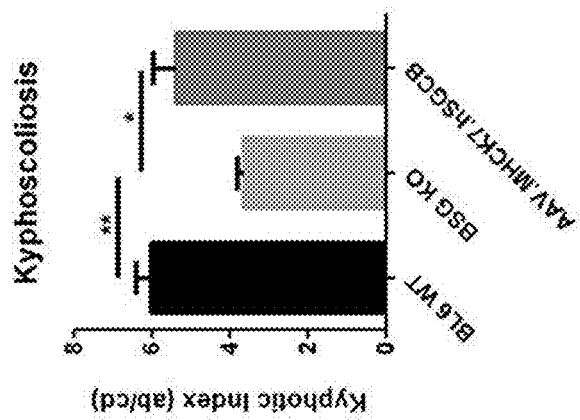

Intravenous Gene Transfer to SGCB-/- Mice Reduces Kyphoscoliosis of Thoracic Spine Degeneration of torso muscles due to the worsening histopathology in patients suffering from LGMD2E patients can be attributed to kyphosis. Kyphoscoliosis of the thoracic spine due to weakening of muscles supporting the spinal column can result in the diaphragm being pushed forward, further compromising lung capacity and diaphragm function. As a result of the severity of the phenotype in the sgcb$^{-/-}$ mouse with the gross anatomical appearance of kyphoscoliosis, full body x-ray radiography was used to determine the degree of kyphosis in 7-month old BL6 WT mice (n=6), sgcb$^{-/-}$ mice (n=6), and treated sgcb-1-mice 6 months post-injection (n=6). The kyphotic index (KI) score determines a quantitative value for the level of kyphoscoliosis (Laws et al. J. Appl. Physiol. 97: 1970-7, 2004). As depicted in the WT panel in FIG. 19a, the KI score is a ratio of length from forelimb to hindlimb compared to the length of the midline to the apex of the curvature in the spine. While sgcb$^{-/-}$ mice present with a severely curved spine and lower KI score of 3.64±0.16 (n=6), BL6 WT mice have a significantly straighter spine resulting in a higher KI score of 6.01±0.41 (n=6) (p<0.01) (FIG. 19b). Treated sgcb$^{-/-}$ mice exhibit a significant reduction in the degree of kyphosis in the spine with an increase in the KI score to 5.39±0.58 (n=6) (p<0.05) (FIG. 19b). These data indicated that intravenous delivery of scAAVrh.74.MHCK7.hSGCB is beneficial for the overall integrity of the spine and can alleviate the kyphosis and joint contractures present in the disease. This data demonstrated the alleviation of kyphosis and increased physical activity in sgcb$^{-/-}$ mice following systemic delivery of the rAAV vector of the invention. This data is additional evidence that the gene therapy of the invention improves the quality of life for LGMD2E patients.

Example 14

Assessment of Cardiomyopathy

Figure 20A:
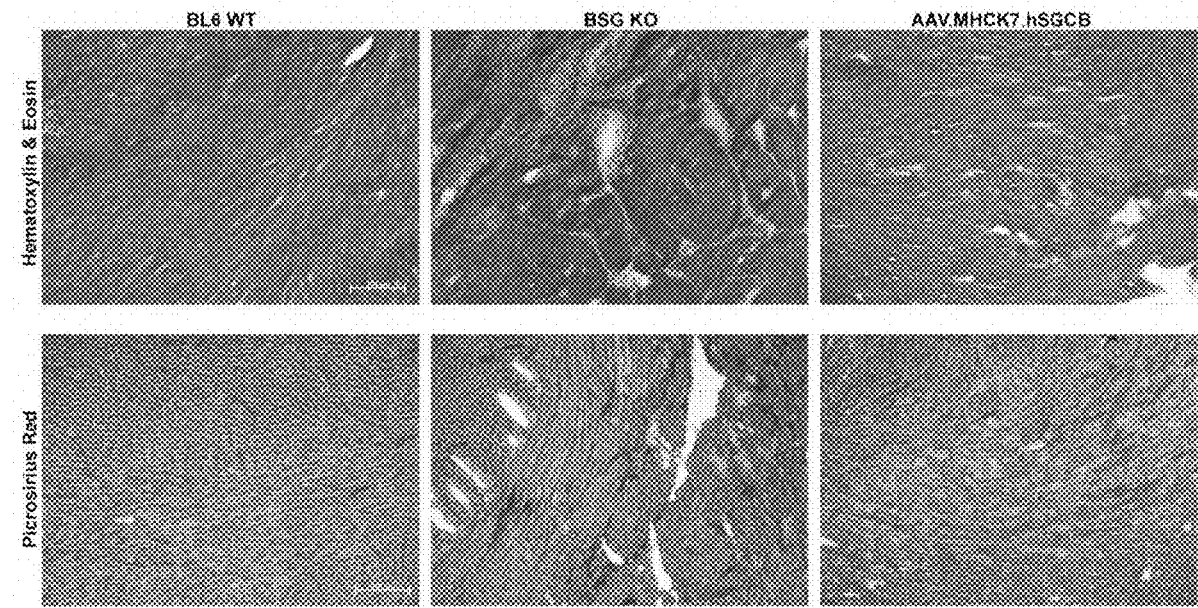
FIG. 20A-D provide the assessment of cardiomyopathy in heart muscle. (a) H&E and picrosirius red stains of 7 month old BL6 WT, sgcb$^{-/-}$, and AAV.MHCK7.hSGCB treated sgcb$^{-/-}$ hearts 6 months post-treatment indicating myocardial degeneration in untreated sgcb$^{-/-}$ muscle and improvement following treatment. (b) Cardiac MRI analysis showing reduction in sgcb$^{-/-}$ hearts in stroke volume (p<0.01), cardiac output, and ejection fraction (p<0.05) (ONE-WAY ANOVA) and improvements 6 months after treatment (n=6 per group). (c) Western blotting of two C57BL/6 WT hearts, two sgcb$^{-/-}$ hearts, and five AAV.MHCK7.hSGCB treated sgcb$^{-/-}$ hearts showing decreased cardiac troponin I levels in diseased mice. (d) Densitometry quantification showing reduction of cardiac troponin I (cTrpI) to 60.38% of BL6 WT levels and an overexpression of up to 135.8% of BL6 WT levels.
Figure 20B:
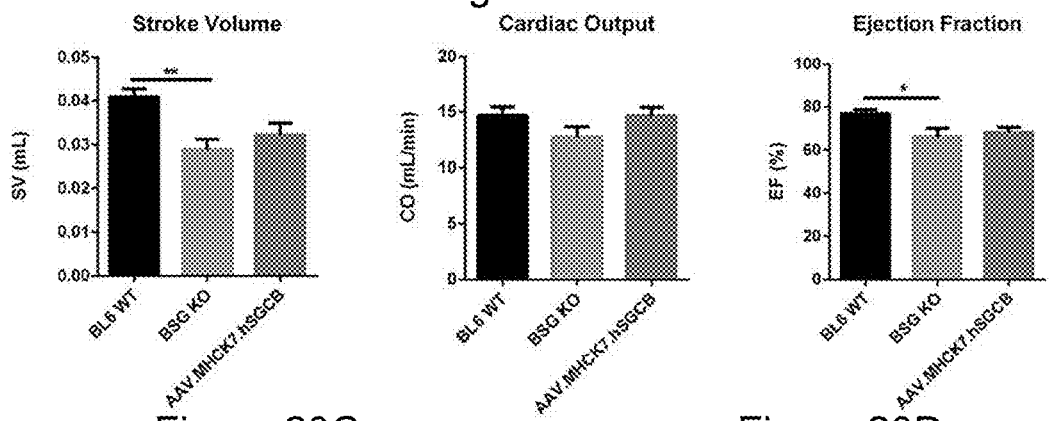
Figure 20C:
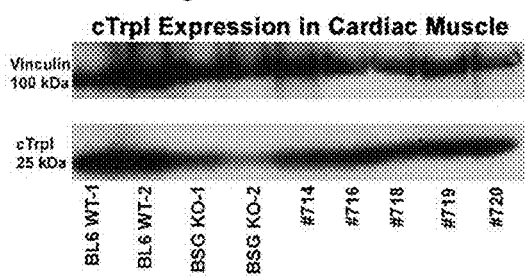
Figure 20D:
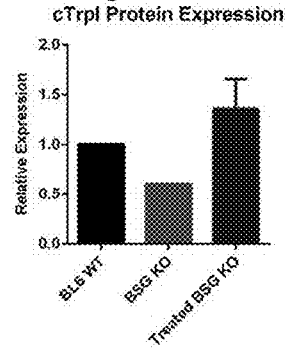

The histological destruction of limb and diaphragm muscle is also detected in the myocardium of 7 month old sgcb$^{-/-}$ mice particularly with the presence of myocardial necrosis and fibrosis as evident by H&E and picrosirius red staining (FIG. 20a). The presentation of impaired heart function often in the form of dilated cardiomyopathy with reduced cardiac output and lower ejection fraction (Semplicini et al., Neurology 84: 1772-81, 2015, Fanin et al., Neuromuscul Disorder 13:303-9, 2003). Cardiac magnetic resonance imaging (MRI), was used to evaluate several functional parameters of the heart in order to establish functional deficits in the myocardium of sgcb$^{-/-}$ mice compared to BL6 WT mice to use as a functional outcome measure. Imaging of control mice at 7 months of age showed a reduction of 29.4% in stroke volume from 0.041±0.0019 mL in sgcb$^{-/-}$ hearts to 0.029±0.0024 mL in BL6 WT hearts (p<0.01), a 31.7% lower cardiac output from 14.70±0.74 mL/min in sgcb$^{-/-}$ hearts to 12.72±0.97 mL/min in BL6 WT hearts, and finally a 14.3% lower ejection fraction, 66.21±3.83% in sgcb$^{-/-}$ hearts compared to 76.90±1.67% in BL6 WT hearts (p<0.05) (FIG. 20b). This indicates a modest decline in overall cardiac function at this age and a trend towards the development of cardiomyopathy. Restoring hSGCB expression in hearts of KO mice through systemic delivery partially corrected these deficits, improving stroke volume to 0.032±0.0027 mL, cardiac output to 14.66±0.75 mL/min, and ejection fraction to 68.16±2.31% (FIG. 19b). As a correlate to the histological and functional disruption of cardiac tissue reported here, western blotting for cardiac troponin I (cTrpI) expression, an important regulator of cardiac function and an indicator (biomarker) of cardiac damage, is reduced in diseased sgcb$^{-/-}$ hearts to 60.38% of the levels seen in BL6 WT mice (FIG. 20c). Levels of cTrpI are restored following treatment to levels of 35.80% of the expression seen in WT hearts (FIG. 20d).

Example 15

Functional Restoration in Diaphragm Muscle with Increase in Physical Activity

Figure 21A:
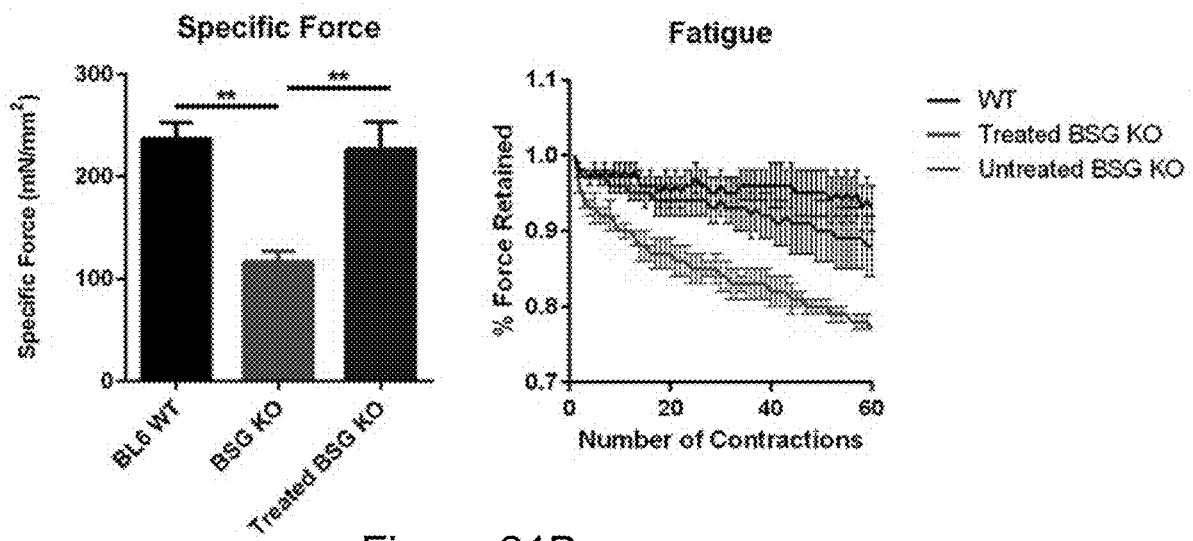
FIG. 21A-B demonstrates diaphragm function correction and increased open-field cage activity. (a) Diaphragm muscle strips were harvested to measure force and resistance to fatigue in BL6 WT mice (n=5), sgcb$^{-/-}$ mice (n=4), and AAV.MHCK7.hSGCB treated sgcb$^{-/-}$ mice (n=5) all at 7 months of age. Six months of treatment restored force to WT levels ($p<0.01$ compared to sgcb$^{-/-}$) and improved resistance to fatigue. (b) Overall ambulation in x and y planes is significantly decreased in sgcb$^{-/-}$ mice ($p<0.0001$) and slightly improved in MCHK7 treated mice ($p<0.05$). Vertical activity rearing onto hindlimbs also decreased in sgcb$^{-/-}$ mice ($p<0.01$) and significantly increased in MCHK7 treated mice ($p<0.05$) (ONE-WAY ANOVA) (n=6 per group).

The significant involvement of diaphragm dysfunction and respiratory failure in LGMD2E mandate functional benefit to the diaphragm essential for validation of clinical systemic therapy. With the use of an ex vivo experimental protocol on strips taken from diaphragm muscle, it was assessed whether restoring β-sarcoglycan provides a functional benefit to this severely compromised muscle. In accordance with the significant histopathology identified in 7 month old diaphragms from diseased mice, sgcb$^{-/-}$ diaphragms (n=4) exhibited a functional deficit with a significant (51%) reduction in specific force output compared to BL6 WT mice (n=5) (116.24±10.49 mN/mm$^2$ vs. 236.67±15.87 mN/mm$^2$, respectively, p<0.001), as well as a greater loss of force from that produced after the first contraction following a rigorous fatigue protocol (23±1.0% loss in sgcb$^{-/-}$; 7.0±3.0% loss in BL6 WT, p<0.05) (FIG. 6a). Six months following tail vein delivery of scAAVrh.74.MHCK7.hSGCB, a dramatic improvement in specific force output was observed. The specific force output increased to 226.07±27.12 mN/mm$^2$ (n=5) (p<0.05 compared to sgcb$^{-/-}$) and better protection of the muscle from repeated fatigue was observed with only a 12.0±4.0% loss of force (p<0.05 compared to sgcb$^{-/-}$) (FIG. 21a). Overall, these data support our previous findings in the TA muscle and show that restoring β-sarcoglycan provides functional recovery in diaphragm muscle.

Figure 21B:
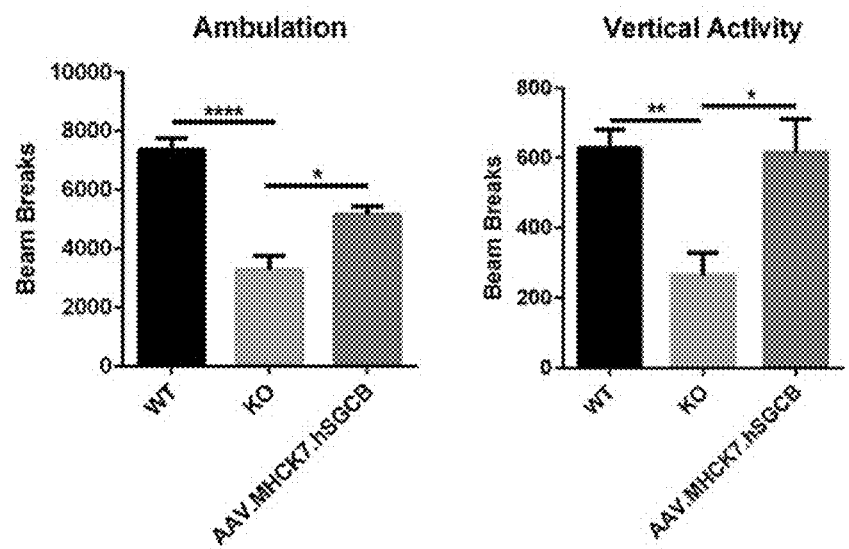

Symptoms of increased fatigue and reduced overall activity are frequently reported in many neuromuscular diseases, partially attributed to the occurrence of kyphosis. As a result and taking into account the phenotype of LGMD2E, it was hypothesized that KO mice would naturally be less active compared to healthy WT mice, and moreover systemic delivery of rAAV.MHCK7.hSGCB to sgcb$^{-/-}$ mice would result in more physically active mice. In order to test this hypothesis and additional potential functional benefits of gene transfer, a laser-monitoring of open-field cage activity protocol similar to that described in Kobayashi et al., Nature 456: 511-5, 2008 and Beastrom et al., Am. J. Pathol. 179: 2464-74, 2011, was performed on all groups of mice. The graphs in FIG. 21b depict a significant decrease (55.5%) in KO mice compared to WT, in both total ambulation (horizontal movement in the x and y planes) and hindlimb vertical rearing. The average number of horizontal ambulatory laser beam breaks over a 1 hour period in WT mice was 7355±400.8 (n=6) compared to 3271±483.8 (n=6) in KO mice (p<0.0001). Furthermore, the average number of vertical rearing beam breaks recorded in WT mice was 626.7±53.76 as opposed to 264.5 ±63.36 in KO mice (p<0.01) (FIG. 21b). In accordance with the initial hypothesis, rAAV.MHCK7.hSGCB treated mice were visibly more active compared to KO which was illustrated in the quantification of activity, where total ambulation increased by 22% to 5143±293.2 beam breaks (p<0.05) and hind limb vertical rearing increased dramatically by 77% to 615.3±95.93 beam breaks (p<0.05) in treated mice (n=6) (FIG. 21b).

Example 16

Safety and Biodistribution Analysis of rAAVrh.74.MHCK7.hSGCB

Figure 22B:
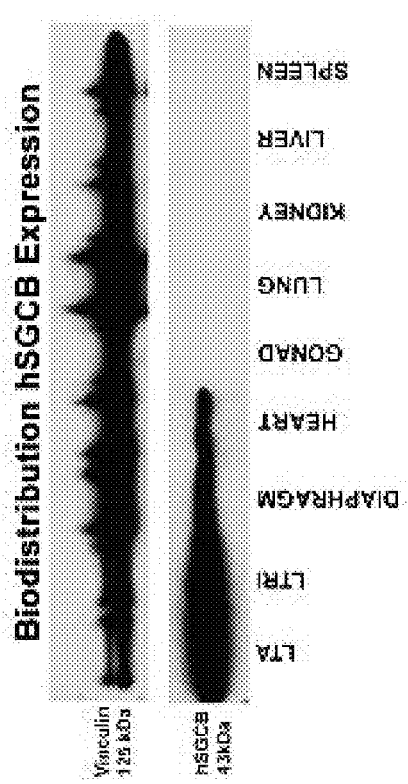
FIG. 22A-B provide biodistribution and off-target transgene expression analysis of systemic scAAVrh.74.MHCK7.hSGCB delivery. (a) Distribution histogram of average vg copies of transcript per microgram DNA added to qPCR reaction in various tissues from two sgcb$^{-/-}$ mice after IV delivery of scAAVrh.74.MHCK7.hSGCB at 1e12 vg total dose. (b) Biodistribution westerns on muscles and organs from scAAVrh.74.MHCK7.hSGCB systemically injected sgcb$^{-/-}$ mice indicating no expression of hSGCB transgene in any non-muscle samples.
Figure 22A:
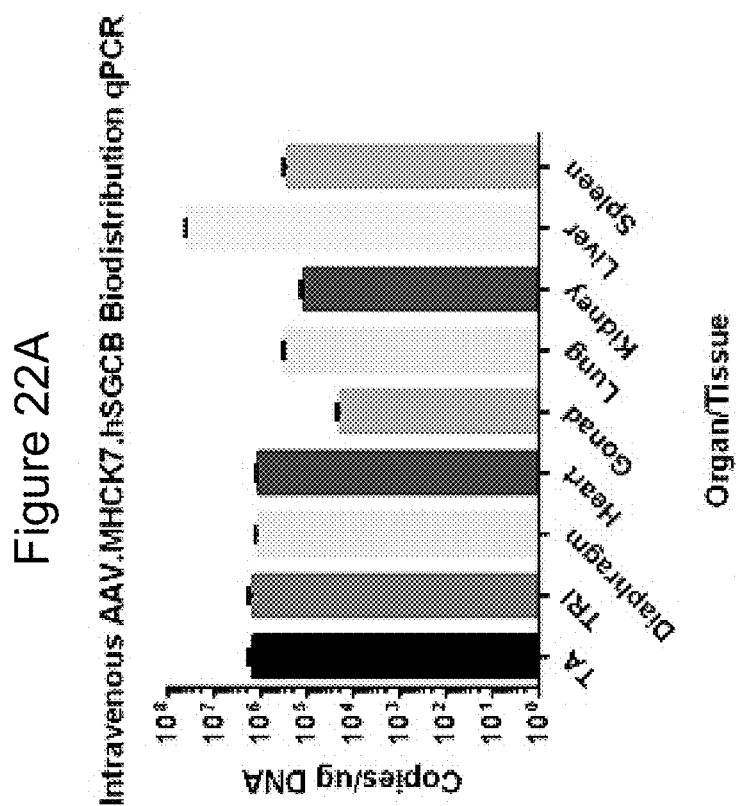

Potential toxicity or safety concerns of hSGCB gene therapy was assessed in sgcb-/- mice at 6 months following systemic delivery of scAAVrh.74.MHCK7.hSGCB at 1.0× 1012 vg total dose (5×1013 vg/kg). Vector biodistribution and off-target transgene expression were analyzed on tissue samples (TA, TRI, diaphragm, heart, gonad, lungs, kidney, liver, and spleen) from vector dosed sgcb$^{-/-}$ animals using qPCR and Western blotting, respectively. Using vector specific primer probe sets, MHCK7.hSGCB vector genomes were detected at varying levels in all collected tissues. As expected, the highest levels were seen in the liver as well as skeletal muscle and the heart, indicating that the test article was efficiently delivered into all intended muscles of vector dosed mice (FIG. 22a). Furthermore, western blotting to detect hSGCB protein expression confirmed the functionality of the muscle specific MHCK7 promoter and the expression of transgene restricted to cardiac and skeletal muscle. Beta-sarcoglycan protein expression was observed in varying amounts in all skeletal muscle samples as well as heart samples, and importantly was not detected in any non-muscle tissue (FIG. 22b), supported by the fact that beta-sarcoglycan is known to be a muscle specific protein. Finally, hematoxylin & eosin staining was performed on cryosections of muscle tissue and all offsite organs harvested from five sgcb$^{-/-}$ mice along with five C57BL6 WT mice treated systemically with our vector at the therapeutic dose used in this study. These sections were then formally reviewed for toxicity by a veterinary pathologist and no adverse effects were detected in any sample from any of the mice. Taken together, these data indicate that this test article was well tolerated by the test animals.

The fact that such high levels of transduction in all muscles throughout the body was achieved with no adverse effects using a relatively low dose (1×10$^{12}$ vg total dose; 5×10$^{13}$ vg/kg) provides great promise for translation to LGMD2E patients. From a clinical perspective, the dose used in the experiments described herein is much lower than the dose used for systemic delivery of an SMN1 expressing AAV therapy delivered to babies with SMA, which is currently in clinical trial (Mendell et al., Mol. Ther. 24: S190, 2016). The highly efficient restoration of β-sarcoglycan expression using the MHCK7 promoter accompanied with functional benefits is very encouraging at dosing levels that could be applied clinically, and given the high incidence of heart involvement in the β-sarcoglycan deficiency in the LGMD2E patients, systemic delivery provides a great benefit to these patients.

REFERENCES

1 Bonnemann C G, Modi R, Noguchi S, Mizuno Y, Yoshida M, Gussoni E et al. Beta-sarcoglycan (A3b) mutations cause autosomal recessive muscular dystrophy with loss of the sarcoglycan complex. Nat Genet 1995; 11: 266-273.
2 Moore S A, Shilling C J, Westra S, Wall C, Wicklund M P, Stolle C et al. Limb-girdle muscular dystrophy in the United States. J Neuropathol Exp Neurol 2006; 65: 995-1003.
3 Araishi K, Sasaoka T, Imamura M, Noguchi S, Hama H, Wakabayashi E et al. Loss of the sarcoglycan complex and sarcospan leads to muscular dystrophy in beta-sarcoglycan-deficient mice. Hum Mol Genet 1999; 8: 1589-1598.
4 Durbeej M, Cohn R D, Hrstka R F, Moore S A, Allamand V, Davidson B L et al. Disruption of the beta-sarcoglycan gene reveals pathogenetic complexity of limb-girdle muscular dystrophy type 2E. Mol Cell 2000; 5: 141-151.
5 Bonnemann C G, Passos-Bueno M R, McNally E M, Vainzof M, de Sa Moreira E, Marie S K et al. Genomic screening for beta-sarcoglycan gene mutations: missense mutations may cause severe limb-girdle muscular dystrophy type 2E (LGMD 2E). Hum Mol Genet 1996; 5: 1953-1961.
6 Angelini C, Fanin M, Freda M P, Duggan D J, Siciliano G, Hoffman E P. The clinical spectrum of sarcoglycanopathies. Neurology 1999; 52: 176-179.
7 Sandona D, Betto R. Sarcoglycanopathies: molecular pathogenesis and therapeutic prospects. Exp Rev Mol Med 2009; 11: e28.
8 Fanin M, Melacini P, Boito C, Pegoraro E, Angelini C. LGMD2E patients risk developing dilated cardiomyopathy. Neuromusc Disord 2003; 13: 303-309.
9 Sveen M L, Thune J J, Kober L, Vissing J. Cardiac involvement in patients with limb-girdle muscular dystrophy type 2 and Becker muscular dystrophy. Arch Neurol 2008; 65: 1196-1201.
10 Melacini P, Fanin M, Duggan D J, Freda M P, Berardinelli A, Danieli G A et al. Heart involvement in muscular dystrophies due to sarcoglycan gene mutations. Muscle Nerve 1999; 22: 473-479.
11 Narayanaswami P, Weiss M, Selcen D, David W, Raynor E, Carter G et al. Evidence-based guideline summary: diagnosis and treatment of limb-girdle and distal dystrophies: report of the guideline development subcommittee of the American Academy of Neurology and the practice issues review panel of the American Association of Neuromuscular & Electrodiagnostic Medicine. Neurology 2014; 83: 1453-1463.
12 Wong-Kisiel L C, Kuntz N L. Two siblings with limb-girdle muscular dystrophy type 2E responsive to deflazacort. Neuromusc Disord 2010; 20: 122-124.
13 Barresi R, Di Blasi C, Negri T, Brugnoni R, Vitali A, Felisari G et al. Disruption of heart sarcoglycan complex and severe cardiomyopathy caused by beta sarcoglycan mutations. J Med Genet 2000; 37: 102-107.
14 Gibertini S, Zanotti S, Savadori P, Curcio M, Saredi S, Salerno F et al. Fibrosis and inflammation are greater in muscles of beta-sarcoglycan-null mouse than mdx mouse. Cell Tissue Res 2014; 356: 427-443.
15 McCarty D M, Fu H, Monahan P E, Toulson C E, Naik P, Samulski R J. Adeno-associated virus terminal repeat (TR) mutant generates self-complementary vectors to overcome the rate-limiting step to transduction in vivo. Gene Ther 2003; 10: 2112-2118.
16 McCarty D M, Monahan P E, Samulski R J. Self-complementary recombinant adeno-associated virus (scAAV) vectors promote efficient transduction independently of DNA synthesis. Gene Ther 2001; 8: 1248-1254.
17 Chicoine L G, Rodino-Klapac L R, Shao G, Xu R, Bremer W G, Camboni M et al. Vascular delivery of rAAVrh74.MCK.GALGT2 to the gastrocnemius muscle of the rhesus macaque stimulates the expression of dystrophin and laminin alpha2 surrogates. Mol Ther 2014; 22: 713-724.
18 Rodino-Klapac L R, Montgomery C L, Bremer W G, Shontz K M, Malik V, Davis N et al. Persistent expression of FLAG-tagged micro dystrophin in nonhuman primates following intramuscular and vascular delivery. Mol Ther 2010; 18: 109-117.
19 Rodino-Klapac L R, Janssen P M, Montgomery C L, Coley B D, Chicoine L G, Clark K R et al. A translational approach for limb vascular delivery of the micro-dystrophin gene without high volume or high pressure for treatment of Duchenne muscular dystrophy. J Transl Med 2007; 5: 45.
20 Wang B, Li J, Fu F H, Chen C, Zhu X, Zhou L et al. Construction and analysis of compact muscle-specific promoters for AAV vectors. Gene Ther 2008; 15: 1489-1499.
21 Chicoine L G, Montgomery C L, Bremer W G, Shontz K M, Griffin D A, Heller K N et al. Plasmapheresis eliminates the negative impact of AAV antibodies on micro-dystrophin gene expression following vascular delivery. Mol Ther 2014; 22: 338-347.
22 Matsuda R, Nishikawa A, Tanaka H. Visualization of dystrophic muscle fibers in mdx mouse by vital staining with Evans blue: evidence of apoptosis in dystrophin-deficient muscle. J Biochem 1995; 118: 959-964.
23 Straub V, Rafael J A, Chamberlain J S, Campbell K P. Animal models for muscular dystrophy show different patterns of sarcolemmal disruption. J Cell Biol 1997; 139: 375-385.
24 Mendell J R, Sahenk Z, Malik V, Gomez A M, Flanigan K M, Lowes L P et al. A phase 1/2a follistatin gene therapy trial for becker muscular dystrophy. Mol Ther 2015; 23: 192-201.
25 Dressman D, Araishi K, Imamura M, Sasaoka T, Liu L A, Engvall E et al. Delivery of alpha- and beta-sarcoglycan by recombinant adeno-associated virus: efficient rescue of muscle, but differential toxicity. Hum Gene Ther 2002; 13: 1631-1646.
26 Rodino-Klapac L R, Lee J S, Mulligan R C, Clark K R, Mendell J R. Lack of toxicity of alpha-sarcoglycan overexpression supports clinical gene transfer trial in LGMD2D. Neurology 2008; 71: 240-247.
27 Shield M A, Haugen H S, Clegg C H, Hauschka S D. E-box sites and a proximal reg-ulatory region of the muscle creatine kinase gene differentially regulate expression in diverse skeletal muscles and cardiac muscle of transgenic mice. Mol Cell Biol 1996; 16: 5058-5068.
28 Rabinowitz J E, Rolling F, Li C, Conrath H, Xiao W, Xiao X et al. Cross-packaging of a single adeno-associated virus (AAV) type 2 vector genome into multiple AAV serotypes enables transduction with broad specificity. J Virol 2002; 76: 791-801.
29 Grieger J C, Choi V W, Samulski R J. Production and characterization of adeno-associated viral vectors. Nat Protoc 2006; 1: 1412-1428.
30 Clark K R, Liu X, McGrath J P, Johnson P R. Highly purified recombinant adeno-associated virus vectors are biologically active and free of detectable helper and wild-type viruses. Hum Gene Ther 1999; 10: 1031-1039.
31 Liu M, Yue Y, Harper S Q, Grange R W, Chamberlain J S, Duan D. Adeno-associated virus-mediated microdystrophin expression protects young mdx muscle from contraction-induced injury. Mol Ther 2005; 11: 245-256.
32 Hakim C H, Grange R W, Duan D. The passive mechanical properties of the extensor digitorum longus muscle are compromised in 2- to 20-mo-old mdx mice. J Appl Physiol 2011; 110: 1656-1663.
33 Wein N, Vulin A, Falzarano M S, Szigyarto C A, Maiti B, Findlay A et al. Translation from a DMD exon 5 IRES results in a functional dystrophin isoform that attenuates dystrophinopathy in humans and mice. Nat Med 2014; 20: 992-1000.

What is claimed is:

1. A recombinant AAV vector comprising a polynucleotide sequence encoding β-sarcoglycan, wherein the polynucleotide sequence comprises a nucleotide sequence at least 95% identical to SEQ ID NO: 1.

2. The recombinant AAV vector of claim 1, wherein the polynucleotide sequence encoding β-sarcoglycan comprises the nucleotide sequence set forth in SEQ ID NO: 1.

3. The recombinant AAV vector of claim 1, wherein the vector is of the serotype AAV1, AAV2, AAV4, AAV5, AAV6, AAV7, AAV8, AAV9, AAV10, AAV11, AAV12, AAV13 or AAV rh.74.

4. The recombinant AAV vector of claim 1, wherein the polynucleotide sequence is operably linked to a muscle-specific control element.

5. The recombinant AAV vector of claim 4, wherein the muscle-specific control element is human skeletal actin gene element, cardiac actin gene element, myocyte-specific enhancer binding factor (MEF) element, muscle creatine kinase (MCK) promoter, truncated MCK (tMCK) promoter, myosin heavy chain (MHC) control element, MHCK7 promoter, C5-12, murine creatine kinase enhancer element, skeletal fast-twitch troponin c gene element, slow-twitch cardiac troponin c gene element, slow-twitch troponin gene element, hypoxia response element (HRE), steroid-inducible element or glucocorticoid response element (GRE).

6. The recombinant AAV vector of claim 5, wherein the muscle-specific control element is the truncated MCK (tMCK) promoter.

7. The recombinant AAV vector of claim 5, wherein the muscle-specific control element is the MHCK7 promoter.

8. The recombinant AAV vector of claim 1 comprising the nucleotide sequence set forth in SEQ ID NO: 3.

9. The recombinant AAV vector of claim 1 comprising the nucleotide sequence set forth in SEQ ID NO: 5.

10. A composition comprising the recombinant AAV vector of claim 1 and a pharmaceutically acceptable carrier, diluent or adjuvant.

11. A method of treating muscular dystrophy in a subject comprising administering to the subject a therapeutically effective amount of the recombinant AAV vector of claim 1.

12. A method of increasing muscular force and/or muscle mass, reducing fibrosis or reducing contraction-induced injury in a mammalian subject suffering from muscular dystrophy comprising administering to the subject a therapeutically effective amount of the recombinant AAV vector of claim 1.

13. A method of treating β-sarcoglycanopathy in a subject comprising administering to the subject a therapeutically effective amount of the recombinant AAV vector of claim 1.

14. The method of claim 11, wherein the subject is suffering from limb-girdle muscular dystrophy.

15. The method of claim 11, wherein the recombinant AAV vector is administered by intramuscular injection or intravenous injection.

16. The method of claim 11, wherein the recombinant AAV vector or the composition is administered systemically.

17. The method of claim 16, where the recombinant AAV vector is parentally administered by injection, infusion or implantation.

18. The method of claim 11, further comprising administering a second recombinant AAV vector comprising a polynucleotide sequence encoding miR-29c.

19. The method of claim 18, wherein the second recombinant vector comprises the nucleotide sequence set forth in SEQ ID NO: 9 or the nucleotide sequence set forth in SEQ ID NO: 8.

20. The method of claim 18, wherein the second recombinant AAV vector is administered by intramuscular injection or intravenous injection.

* * * * *

SEQUENCE LISTING

```
<160> NUMBER OF SEQ ID NOS: 18

<210> SEQ ID NO 1
<211> LENGTH: 957
<212> TYPE: DNA
<213> ORGANISM: Homo sapiens
<220> FEATURE:
<221> NAME/KEY: misc_feature
<223> OTHER INFORMATION: Beta-sarcoglycan

<400> SEQUENCE: 1
atggcagcag cagccgccgc agccgccgag cagcagtcaa gcaatggacc agtgaaaaaa      60
tcaatgagag aaaaagccgt cgagaggaga tcagtgaata aggagcacaa cagcaatttc     120
aaagccggct acatccctat tgacgaagat cgcctgcata agacaggcct gaggggcgc      180 aaaggaaacc tggcaatctg cgtcatcatt ctgctgttta tcctggccgt gattaatctg     240
atcattactc tggtgatttg ggctgtcatc cgcattggcc caaacgggtg tgactctatg     300
gagttccacg aaagtggcct gctgcgattt aagcaggtgt ccgatatggg ggtcatccat     360
ccactgtaca aatctactgt cggcgggcgg agaaacgaga atctggtgat caccgggaac     420
aatcagccca ttgtgttcca gcagggaacc acaaagctgt ctgtggaaaa caataaaaca     480
tcaatcacta gcgacattgg catgcagttc tttgatcccc ggacccagaa tatcctgttc     540
agtaccgact atgagacaca cgaatttcat ctgccttccg gggtgaagtc tctgaacgtc     600
cagaaagcca gcactgagag aatcaccagt aacgctacat cagacctgaa tatcaaggtg     660
gatggacgag ctattgtccg gggaaatgag ggcgtgttca tcatgggcaa gacaattgaa     720
tttcacatgg gaggcaacat ggagctgaaa gcagaaaaca gcatcattct gaatgggagc     780
gtgatggtct ccactaccag actgcccagc tcctctagtg gagaccagct ggggtccgga     840
gattgggtca ggtataagct gtgcatgtgt gccgatggca ccctgtttaa agtgcaggtc     900
accagccaga atatgggatg tcagattagc gataacccct tgtgggaatac tcattaa      957

<210> SEQ ID NO 2
<211> LENGTH: 318
<212> TYPE: PRT
<213> ORGANISM: Homo sapiens
<220> FEATURE:
<221> NAME/KEY: MISC_FEATURE
<223> OTHER INFORMATION: Beta-sarcoglycan

<400> SEQUENCE: 2

Met Ala Ala Ala Ala Ala Ala Ala Ala Glu Gln Gln Ser Ser Asn Gly
1               5                   10                  15

Pro Val Lys Lys Ser Met Arg Glu Lys Ala Val Glu Arg Arg Ser Val
                20                  25                  30

Asn Lys Glu His Asn Ser Asn Phe Lys Ala Gly Tyr Ile Pro Ile Asp
```

|   |   |   |   | 35 |   |   |   | 40 |   |   |   | 45 |   |   |
|---|---|---|---|----|---|---|---|----|---|---|---|----|---|---|

Glu Asp Arg Leu His Lys Thr Gly Leu Arg Gly Arg Lys Gly Asn Leu
 50                  55                  60

Ala Ile Cys Val Ile Ile Leu Leu Phe Ile Leu Ala Val Ile Asn Leu
 65                  70                  75                  80

Ile Ile Thr Leu Val Ile Trp Ala Val Ile Arg Ile Gly Pro Asn Gly
                 85                  90                  95

Cys Asp Ser Met Glu Phe His Glu Ser Gly Leu Leu Arg Phe Lys Gln
             100                 105                 110

Val Ser Asp Met Gly Val Ile His Pro Leu Tyr Lys Ser Thr Val Gly
         115                 120                 125

Gly Arg Arg Asn Glu Asn Leu Val Ile Thr Gly Asn Asn Gln Pro Ile
 130                 135                 140

Val Phe Gln Gln Gly Thr Thr Lys Leu Ser Val Glu Asn Asn Lys Thr
145                 150                 155                 160

Ser Ile Thr Ser Asp Ile Gly Met Gln Phe Phe Asp Pro Arg Thr Gln
                165                 170                 175

Asn Ile Leu Phe Ser Thr Asp Tyr Glu Thr His Glu Phe His Leu Pro
            180                 185                 190

Ser Gly Val Lys Ser Leu Asn Val Gln Lys Ala Ser Thr Glu Arg Ile
        195                 200                 205

Thr Ser Asn Ala Thr Ser Asp Leu Asn Ile Lys Val Asp Gly Arg Ala
210                 215                 220

Ile Val Arg Gly Asn Glu Gly Val Phe Ile Met Gly Lys Thr Ile Glu
225                 230                 235                 240

Phe His Met Gly Gly Asn Met Glu Leu Lys Ala Glu Asn Ser Ile Ile
                245                 250                 255

Leu Asn Gly Ser Val Met Val Ser Thr Thr Arg Leu Pro Ser Ser Ser
            260                 265                 270

Ser Gly Asp Gln Leu Gly Ser Gly Asp Trp Val Arg Tyr Lys Leu Cys
        275                 280                 285

Met Cys Ala Asp Gly Thr Leu Phe Lys Val Gln Val Thr Ser Gln Asn
290                 295                 300

Met Gly Cys Gln Ile Ser Asp Asn Pro Cys Gly Asn Thr His
305                 310                 315

<210> SEQ ID NO 3
<211> LENGTH: 2306
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: pAAV.MHCK7.hSCGB

<400> SEQUENCE: 3

```
ctgcgcgctc gctcgctcac tgaggccgcc cgggcaaagc ccgggcgtcg ggcgaccttt      60
ggtcgcccgg cctcagtgag cgagcgagcg cgcagagagg gagtgggggtt aaccaattgg    120 cgcggccgca agcttgcatg tctaagctag acccttcaga ttaaaaataa ctgaggtaag    180
ggcctgggta ggggaggtgg tgtgagacgc tcctgtctct cctctatctg cccatcggcc    240
ctttggggag gaggaatgtg cccaaggact aaaaaaaggc catggagcca gaggggcgag    300
ggcaacagac ctttcatggg caaaccttgg ggccctgctg tctagcatgc cccactacgg    360
gtctaggctg cccatgtaag gaggcaaggc ctggggacac ccgagatgcc tggttataat    420
```

```
taacccagac atgtggctgc cccccccccc ccaacacctg ctgcctctaa aataacccct      480
gtccctggtg atcccctgc atgcgaagat cttcgaacaa ggctgtgggg gactgagggc      540
aggctgtaac aggcttgggg gccagggctt atacgtgcct gggactccca aagtattact      600
gttccatgtt cccggcgaag ggccagctgt cccccgccag ctagactcag cacttagttt      660
aggaaccagt gagcaagtca gcccttgggg cagcccatac aaggccatgg ggctgggcaa      720
gctgcacgcc tgggtccggg gtgggcacgg tgcccgggca acgagctgaa agctcatctg      780
ctctcagggg cccctccctg ggacagccc ctcctggcta gtcacaccct gtaggctcct       840
ctatataacc caggggcaca ggggctgccc tcattctacc accacctcca cagcacagac      900
agacactcag gagcagccag cggcgcgccc aggtaagttt agtcttttg tcttttattt       960 caggtcccgg atccggtggt ggtgcaaatc aaagaactgc tcctcagtgg atgttgcctt     1020
tacttctagg cctgtacgga agtgttactt ctgctctaaa agctgcggaa ttgtacccgg     1080
taccgccacc atggcagcag cagccgccgc agccgccgag cagcagtcaa gcaatggacc     1140
agtgaaaaaa tcaatgagag aaaaagccgt cgagaggaga tcagtgaata aggagcacaa     1200
cagcaatttc aaagccggct acatccctat tgacgaagat cgcctgcata agacaggcct     1260 gaggggcgc aaaggaaacc tggcaatctg cgtcatcatt ctgctgttta tcctggccgt      1320
gattaatctg atcattactc tggtgatttg ggctgtcatc cgcattggcc caaacgggtg     1380
tgactctatg gagttccacg aaagtggcct gctgcgattt aagcaggtgt ccgatatggg     1440
ggtcatccat ccactgtaca aatctactgt cggcgggcgg agaaacgaga atctggtgat     1500
caccgggaac aatcagccca ttgtgttcca gcagggaacc acaaagctgt ctgtggaaaa     1560
caataaaaca tcaatcacta gcgacattgg catgcagttc tttgatcccc ggacccagaa     1620
tatcctgttc agtaccgact atgagacaca cgaatttcat ctgccttccg gggtgaagtc     1680
tctgaacgtc cagaaagcca gcactgagag aatcaccagt aacgtacat cagacctgaa      1740 tatcaaggtg gatggacgag ctattgtccg gggaaatgag ggcgtgttca tcatgggcaa     1800
gacaattgaa tttcacatgg gaggcaacat ggagctgaaa gcagaaaaca gcatcattct     1860
gaatgggagc gtgatggtct ccactaccag actgcccagc tcctctagtg agaccagct     1920 ggggtccgga gattgggtca ggtataagct gtgcatgtgt gccgatggca ccctgttaa     1980 agtgcaggtc accagccaga atatgggatg tcagattagc gataaccctt gtgggaatac     2040
tcattaaaag cttggccgca ataaaagatc tttattttca ttagatctgt gtgttggttt     2100
tttgtgtgtc ctgcaggggc gcgcctctag agcatggcta cgtagataag tagcatggcg     2160
ggttaatcat taactacaag gaacccctag tgatggagtt ggccactccc tctctgcgcg     2220
ctcgctcgct cactgaggcc gggcgaccaa aggtcgcccg acgcccgggc tttgcccggg     2280
cggcctcagt gagcgagcga gcgcgc                                          2306
```

<210> SEQ ID NO 4
<211> LENGTH: 792
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: MHCK7 promoter

<400> SEQUENCE: 4

```
aagcttgcat gtctaagcta gacccttcag attaaaaata actgaggtaa gggcctgggt       60
```

| | | | | | |
|---|---|---|---|---|---|
| aggggaggtg | gtgtgagacg | ctcctgtctc | tcctctatct | gcccatcggc | cctttgggga | 120 |
| ggaggaatgt | gcccaaggac | taaaaaaagg | ccatggagcc | agaggggcga | gggcaacaga | 180 |
| cctttcatgg | gcaaaccttg | gggccctgct | gtctagcatg | ccccactacg | ggtctaggct | 240 |
| gcccatgtaa | ggaggcaagg | cctggggaca | cccgagatgc | ctggttataa | ttaacccaga | 300 |
| catgtggctg | ccccccccc | cccaacacct | gctgcctcta | aaataaccc | tgtccctggt | 360 |
| ggatccctg | catgcgaaga | tcttcgaaca | aggctgtggg | ggactgaggg | caggctgtaa | 420 |
| caggcttggg | ggccagggct | tatacgtgcc | tgggactccc | aaagtattac | tgttccatgt | 480 |
| tcccggcgaa | gggccagctg | tcccccgcca | gctagactca | gcacttagtt | taggaaccag | 540 |
| tgagcaagtc | agcccttggg | gcagcccata | caaggccatg | gggctgggca | agctgcacgc | 600 |
| ctgggtccgg | ggtgggcacg | gtgcccgggc | aacgagctga | aagctcatct | gctctcaggg | 660 |
| gcccctccct | ggggacagcc | cctcctggct | agtcacaccc | tgtaggctcc | tctatataac | 720 |
| ccaggggcac | aggggctgcc | ctcattctac | caccacctcc | acagcacaga | cagacactca | 780 |
| ggagcagcca | gc | | | | | 792 |

<210> SEQ ID NO 5
<211> LENGTH: 2244
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: pAAV.tMCK.hSGCB

<400> SEQUENCE: 5

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtgggggtt | aaccaattgg | 120 |
| cggccgcaaa | cttgcatgcc | ccactacggg | tctaggctgc | ccatgtaagg | aggcaaggcc | 180 |
| tggggacacc | cgagatgcct | ggttataatt | aaccccaaca | cctgctgccc | ccccccccc | 240 |
| aacacctgct | gcctgagcct | gagcggttac | cccaccccgg | tgcctgggtc | ttaggctctg | 300 |
| tacaccatgg | aggagaagct | cgctctaaaa | ataaccctgt | ccctggtgga | tccactacgg | 360 |
| gtctatgctg | cccatgtaag | gaggcaaggc | ctggggacac | ccgagatgcc | tggttataat | 420 |
| taaccccaac | acctgctgcc | ccccccccc | caacacctgc | tgcctgagcc | tgagcggtta | 480 |
| ccccaccccg | gtgcctgggt | cttaggctct | gtacaccatg | gaggagaagc | tcgctctaaa | 540 |
| aataaccctg | tccctggtgg | accactacgg | gtctaggctg | cccatgtaag | gaggcaaggc | 600 |
| ctggggacac | ccgagatgcc | tggttataat | taaccccaac | acctgctgcc | ccccccccc | 660 |
| aacacctgct | gcctgagcct | gagcggttac | cccaccccgg | tgcctgggtc | ttaggctctg | 720 |
| tacaccatgg | aggagaagct | cgctctaaaa | ataaccctgt | ccctggtcct | ccctggggac | 780 |
| agcccctcct | ggctagtcac | accctgtagg | ctcctctata | taacccaggg | gcacaggggc | 840 |
| tgccccgggg | tcacctgcag | aagttggtcg | tgaggcactg | ggcaggtaag | tatcaaggtt | 900 |
| acaagacagg | tttaaggaga | ccaatagaaa | ctgggcttgt | cgagacagag | aagactcttg | 960 |
| cgtttctgat | aggcacctat | tggtcttact | gacatccact | ttgcctttct | ctccacaggt | 1020 |
| gtccactccc | agttcaatta | cagcgcgtgg | taccaccatg | gcagcagcag | ccgccgcagc | 1080 |
| cgccgagcag | cagtcaagca | atggaccagt | gaaaaaatca | atgagagaaa | aagccgtcga | 1140 |
| gaggagatca | gtgaataagg | agcacaacag | caatttcaaa | gccggctaca | tccctattga | 1200 |

```
cgaagatcgc ctgcataaga caggcctgag ggggcgcaaa ggaaacctgg caatctgcgt        1260
catcattctg ctgtttatcc tggccgtgat taatctgatc attactctgg tgatttgggc        1320
tgtcatccgc attggcccaa acgggtgtga ctctatggag ttccacgaaa gtggcctgct        1380
gcgatttaag caggtgtccg atatgggggt catccatcca ctgtacaaat ctactgtcgg        1440
cgggcggaga aacgagaatc tggtgatcac cgggaacaat cagcccattg tgttccagca        1500
gggaaccaca aagctgtctg tggaaaacaa taaaacatca atcactagcg acattggcat        1560
gcagttcttt gatccccgga cccagaatat cctgttcagt accgactatg agacacacga        1620
atttcatctg ccttccgggg tgaagtctct gaacgtccag aaagccagca ctgagagaat        1680
caccagtaac gctacatcag acctgaatat caaggtggat ggacgagcta ttgtccgggg        1740
aaatgagggc gtgttcatca tgggcaagac aattgaattt cacatgggag caacatgga         1800 gctgaaagca gaaaacagca tcattctgaa tgggagcgtg atggtctcca ctaccagact        1860
gcccagctcc tctagtggag accagctggg gtccggagat tgggtcaggt ataagctgtg        1920
catgtgtgcc gatggcaccc tgtttaaagt gcaggtcacc agccagaata tgggatgtca        1980
gattagcgat aacccttgtg ggaatactca ttaaaagctt ggccgcaata aaagatcttt        2040 atttcatta gatctgtgtg ttggtttttt gtgtgtcctg caggggcgcg cctctagagc         2100
atggctacgt agataagtag catggcgggt taatcattaa ctacaaggaa ccctagtga         2160 tggagttggc cactccctct ctgcgcgctc gctcgctcac tgaggccggg cgaccaaagg        2220
tcgcccgacg cccgggcttt gccc                                               2244

<210> SEQ ID NO 6
<211> LENGTH: 714
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK promoter

<400> SEQUENCE: 6
ccactacggg tctaggctgc ccatgtaagg aggcaaggcc tggggacacc cgagatgcct          60
ggttataatt aaccccaaca cctgctgccc cccccccc aacacctgct gcctgagcct          120
gagcggttac cccaccccgg tgcctgggtc ttaggctctg tacaccatgg aggagaagct         180
cgctctaaaa ataaccctgt ccctggtgga tccactacgg gtctatgctg cccatgtaag         240
gaggcaaggc ctggggacac ccgagatgcc tggttataat taaccccaac acctgctgcc         300 ccccccccc caacacctgc tgcctgagcc tgagcggtta ccccaccccg gtgcctgggt         360
cttaggctct gtacaccatg gaggagaagc tcgctctaaa ataaccctg tccctggtgg          420 accactacgg gtctaggctg cccatgtaag gaggcaaggc ctggggacac ccgagatgcc         480
tggttataat taaccccaac acctgctgcc cccccccc aacacctgct gcctgagcct         540
gagcggttac cccaccccgg tgcctgggtc ttaggctctg tacaccatgg aggagaagct         600
cgctctaaaa ataaccctgt ccctggtcct cctgggggac agcccctcct ggctagtcac         660
accctgtagg ctcctctata taacccaggg gcacaggggc tgccccgggg tcac               714

<210> SEQ ID NO 7
<211> LENGTH: 296
<212> TYPE: DNA
<213> ORGANISM: Artificial Sequence
```

<220> FEATURE:
<223> OTHER INFORMATION: Primer
<220> FEATURE:
<221> NAME/KEY: misc_feature
<223> OTHER INFORMATION: miR29c

<400> SEQUENCE: 7

| | | | | | |
|---|---|---|---|---|---|
| ggccggcctg | tttgaatgag | gcttcagtac | tttacagaat | cgttgcctgc | acatcttgga | 60 |
| aacacttgct | gggattactt | cttcaggtta | acccaacaga | aggctcgaga | aggtatattg | 120 |
| ctgttgacag | tgagcgcaac | cgatttcaaa | tggtgctaga | gtgaagccac | agatgtctag | 180 |
| caccatttga | aatcggttat | gcctactgcc | tcggaattca | aggggctact | ttaggagcaa | 240 |
| ttatcttgtt | tactaaaact | gaatacccttg | ctatctcttt | gatacattgg | ccggcc | 296 |

<210> SEQ ID NO 8
<211> LENGTH: 3384
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: pAAV.CMV.Mir29C

<400> SEQUENCE: 8

| | | | | | |
|---|---|---|---|---|---|
| cagcagctgc | gcgctcgctc | gctcactgag | gccgcccggg | caaagcccgg | gcgtcgggcg | 60 |
| acctttggtc | gcccggcctc | agtgagcgag | cgagcgcgca | gagagggagt | ggggttaaac | 120 |
| tcgttacata | acttacggta | aatggcccgc | ctggctgacc | gcccaacgac | ccccgcccat | 180 |
| tgacgtcaat | aatgacgtat | gttcccatag | taacgccaat | agggactttc | cattgacgtc | 240 |
| aatgggtgga | gtatttacgg | taaactgccc | acttggcagt | acatcaagtg | tatcatatgc | 300 |
| caagtacgcc | ccctattgac | gtcaatgacg | gtaaatggcc | cgcctggcat | tatgcccagt | 360 |
| acatgacctt | atgggacttt | cctacttggc | agtacatcta | cgtattagtc | atcgctatta | 420 |
| ccatggtgat | gcggttttgg | cagtacatca | atgggcgtgg | atagcggttt | gactcacggg | 480 |
| gatttccaag | tctccacccc | attgacgtca | atgggagttt | gttttggcac | caaaatcaac | 540 |
| gggactttcc | aaaatgtcgt | aacaactccg | ccccattgac | gcaaatgggc | ggtaggcgtg | 600 |
| tacggtggga | ggtctatata | agcagagctc | gtttagtgaa | ccgtcagatc | gcctggagac | 660 |
| gccatccacg | ctgttttgac | ctccatagaa | gacaccggga | ccgatccagc | ctccggactc | 720 |
| tagaggatcc | ggtactcgag | gaactgaaaa | accagaaagt | taactggtaa | gtttagtctt | 780 |
| tttgtctttt | atttcaggtc | ccggatccgg | tggtggtgca | aatcaaagaa | ctgctcctca | 840 |
| gtggatgttg | cctttacttc | taggcctgta | cggaagtgtt | acttctgctc | taaaagctgc | 900 |
| ggaattgtac | ccgggggccga | tccaccggtc | tttttcgcaa | cgggtttgcc | gccagaacac | 960 |
| aggtaagtgc | cgtgtgtggt | tcccgcgggc | ggcgacgggg | cccgtgcgtc | cagcgcaca | 1020 |
| tgttcggcga | ggcggggcct | gcgagcgcgg | ccaccgagaa | tcggacgggg | gtagtctcaa | 1080 |
| gctggccggc | ctgtttgaat | gaggcttcag | tactttacag | aatcgttgcc | tgcacatctt | 1140 |
| ggaaacactt | gctgggatta | cttcttcagg | ttaacccaac | agaaggctcg | agaaggtata | 1200 |
| ttgctgttga | cagtgagcgc | aaccgatttc | aaatggtgct | agagtgaagc | cacagatgtc | 1260 |
| tagcaccatt | tgaaatcggt | tatgcctact | gcctcggaat | tcaaggggct | actttaggag | 1320 |
| caattatctt | gttactaaa | actgaatacc | ttgctatctc | tttgatacat | tggccggcct | 1380 |
| gctctggtgc | ctggcctcgc | gccgccgtgt | atcgccccgc | cctgggcggc | aaggctggcc | 1440 |

| | |
|---|---|
| cggtcggcac cagttgcgtg agcggaaaga tggccgcttc ccggccctgc tgcagggagc | 1500 |
| tcaaaatgga ggacgcggcg ctcgggagag cgggcgggtg agtcacccac acaaaggaaa | 1560 |
| agggcctttc cgtcctcagc cgtcgcttca tgtgactcca cggagtaccg ggcgccgtcc | 1620 |
| aggcacctcg attagttctc gagcttttgg agtacgtcgt ctttaggttg ggggagggg | 1680 |
| ttttatgcga tggagtttcc ccacactgag tgggtggaga ctgaagttag gccagcttgg | 1740 |
| cacttgatgt aattctcctt ggaatttgcc cttttttgagt ttggatcttg gttcattctc | 1800 |
| aagcctcaga cagtggttca agttttttt cttccatttc aggtgtcgtg aaaagctagc | 1860 |
| gctaccggac tcagatctcg agctcaagct gcggggatcc agacatgata agatacattg | 1920 |
| atgagtttgg acaaaccaca actagaatgc agtgaaaaaa atgctttatt tgtgaaattt | 1980 |
| gtgatgctat tgctttattt gtaaccatta taagctgcaa taaacaagtt aacaacaaca | 2040 |
| attgcattca ttttatgttt caggttcagg gggaggtgtg ggaggttttt tcactagtag | 2100 |
| catggctacg tagataagta gcatggcggg ttaatcatta actacaagga acccctagtg | 2160 |
| atggagttgg ccactccctc tctgcgcgct cgctcgctca ctgaggccgg gcgaccaaag | 2220 |
| gtcgcccgac gcccgggctt tgcccgggcg gcctcagtga gcgagcgagc gcgccagctg | 2280 |
| gcgtaatagc gaagaggccc gcaccgatcg cccttcccaa cagttgcgca gcctgaatgg | 2340 |
| cgaatggaat tccagacgat tgagcgtcaa aatgtaggta tttccatgag cgttttcct | 2400 |
| gttgcaatgg ctggcggtaa tattgttctg gatattacca gcaaggccga tagtttgagt | 2460 |
| tcttctactc aggcaagtga tgttattact aatcaaagaa gtattgcgac aacggttaat | 2520 |
| ttgcgtgatg gacagactct tttactcggt ggcctcactg attataaaaa cacttctcag | 2580 |
| gattctggcg taccgttcct gtctaaaatc cctttaatcg gcctcctgtt tagctcccgc | 2640 |
| tctgattcta acgaggaaag cacgttatac gtgctcgtca aagcaaccat agtacgcgcc | 2700 |
| ctgtagcggc gcattaagcg cggcgggtgt ggtggttacg cgcagcgtga ccgctacact | 2760 |
| tgccagcgcc ctagcgcccg ctcctttcgc tttcttccct tcctttctcg ccacgttcgc | 2820 |
| cggctttccc cgtcaagctc taaatcgggg gctcccttta gggttccgat ttagtgcttt | 2880 |
| acggcacctc gaccccaaaa aacttgatta gggtgatggt tcacgtagtg ggccatcgcc | 2940 |
| ctgatagacg ttttttcgcc ctttgacgtt ggagtccacg ttctttaata gtggactctt | 3000 |
| gttccaaact ggaacaacac tcaaccctat ctcggtctat tcttttgatt tataagggat | 3060 |
| tttgccgatt tcggcctatt ggttaaaaaa tgagctgatt taacaaaaat ttaacgcgaa | 3120 |
| ttttaacaaa atattaacgt ttacaattta aatatttgct tatacaatct tcctgttttt | 3180 |
| ggggcttttc tgattatcaa ccggggtaca tatgattgac atgctagttt tacgattacc | 3240 |
| gttcatcgat tctcttgttt gctccagact ctcaggcaat gacctgatag cctttgtaga | 3300 |
| gacctctcaa aaatagctac cctctccggc atgaatttat cagctagaac ggttgaatat | 3360 |
| catattgatg gtgatttgac tgtc | 3384 |

<210> SEQ ID NO 9
<211> LENGTH: 296
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: miR29c

<400> SEQUENCE: 9

-continued

```
ggccggcctg tttgaatgag gcttcagtac tttacagaat cgttgcctgc acatcttgga      60
aacacttgct gggattactt cttcaggtta acccaacaga aggctcgaga aggtatattg     120
ctgttgacag tgagcgcaac cgatttcaaa tggtgctaga gtgaagccac agatgtctag    180
caccatttga aatcggttat gcctactgcc tcggaattca aggggctact ttaggagcaa    240
ttatcttgtt tactaaaact gaataccttg ctatctcttt gatacattgg ccggcc        296
```

```
<210> SEQ ID NO 10
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK forward primer

<400> SEQUENCE: 10
acccgagatg cctggttata att                                             23
```

```
<210> SEQ ID NO 11
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK reverse primer

<400> SEQUENCE: 11
tccatggtgt acagagccta agac                                            24
```

```
<210> SEQ ID NO 12
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK probe
<220> FEATURE:
<221> NAME/KEY: misc_feature
<222> LOCATION: (1)..(1)
<223> OTHER INFORMATION: 5' FAM
<220> FEATURE:
<221> NAME/KEY: misc_feature
<222> LOCATION: (25)..(25)
<223> OTHER INFORMATION: 3' TAMRA

<400> SEQUENCE: 12
ctgctgcctg agcctgagcg gttac                                           25
```

```
<210> SEQ ID NO 13
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK intron Forward Primer

<400> SEQUENCE: 13
gtgaggcact gggcaggtaa                                                 20
```

```
<210> SEQ ID NO 14
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK intron Reverse Primer

<400> SEQUENCE: 14
acctgtggag agaaaggcaa ag                                              22

<210> SEQ ID NO 15
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK intron Probe
<220> FEATURE:
<221> NAME/KEY: misc_feature
<222> LOCATION: (1)..(1)
<223> OTHER INFORMATION: 5' 6FAM
<220> FEATURE:
<221> NAME/KEY: misc_feature
<222> LOCATION: (39)..(39)
<223> OTHER INFORMATION: 3' TAMRA

<400> SEQUENCE: 15
atcaaggtta caagacaggt ttaaggagac caatagaaa                            39

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
ccaacacctg ctgcctctaa a                                               21

<210> SEQ ID NO 17
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: MHCK7 reverse primer

<400> SEQUENCE: 17
gtcccccaca gccttgttc                                                  19

<210> SEQ ID NO 18
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: MHCK7 probe
<220> FEATURE:
<221> NAME/KEY: misc_feature
<222> LOCATION: (1)..(1)
<223> OTHER INFORMATION: 5' FAM
<220> FEATURE:
```

```
<221> NAME/KEY: misc_feature
<222> LOCATION: (9)..(9)
<223> OTHER INFORMATION: Zen
<220> FEATURE:
<221> NAME/KEY: misc_feature
<222> LOCATION: (23)..(23)
<223> OTHER INFORMATION: 3IABKFQ

<400> SEQUENCE: 18
tggatcccct gcatgcgaag atc                                          23
```